(12) United States Patent
Blackaby et al.

(10) Patent No.: US 7,851,638 B2
(45) Date of Patent: Dec. 14, 2010

(54) CYCLOHEXANESULFONYL DERIVATIVES AS GLYT1 INHIBITORS TO TREAT SCHIZOPHRENIA

(75) Inventors: Wesley Peter Blackaby, Buckhurst Hill (GB); Jose Luis Castro Pineiro, Bishops Stortford (GB); Richard Thomas Lewis, Bishops Stortford (GB); Elizabeth Mary Naylor, Saffron Walden (GB); Leslie Joseph Street, Little Hallingbury (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 0 days.

(21) Appl. No.: 12/571,904

(22) Filed: Oct. 1, 2009

(65) Prior Publication Data

US 2010/0029726 A1     Feb. 4, 2010

Related U.S. Application Data

(62) Division of application No. 11/446,735, filed on Jun. 5, 2006, now Pat. No. 7,626,056.

(30) Foreign Application Priority Data

| Jun. 6, 2005 | (GB) | .................................. 0511452.5 |
| Aug. 17, 2005 | (GB) | .................................. 0516787.9 |
| Dec. 8, 2005 | (GB) | .................................. 0524968.5 |

(51) Int. Cl.
C07D 249/02    (2006.01)
A61K 31/4192   (2006.01)

(52) U.S. Cl. ........................ 548/255; 548/136; 548/186; 548/356.1; 514/359; 514/362; 514/403

(58) Field of Classification Search ................. 514/356, 514/362, 403, 616; 548/136, 255, 356.1, 548/186
See application file for complete search history.

(56) References Cited

U.S. PATENT DOCUMENTS

| 6,127,191 | A | 10/2000 | Graybill et al. |
| 6,201,024 | B1 | 3/2001 | Baxter et al. |
| 6,953,806 | B2 | 10/2005 | Ackermann et al. |
| 7,335,670 | B2 | 2/2008 | Dargazanli et al. |
| 7,626,056 | B2 * | 12/2009 | Blackaby et al. ............ 564/186 |
| 2005/0272774 | A1 | 12/2005 | Ackermann et al. |
| 2007/0105902 | A1 | 5/2007 | Lindsley et al. |
| 2007/0249606 | A1 | 10/2007 | Lindsley et al. |
| 2007/0254880 | A1 | 11/2007 | Blackaby et al. |
| 2008/0021010 | A1 | 1/2008 | Lindsley et al. |
| 2008/0090796 | A1 | 4/2008 | Blackaby et al. |
| 2008/0108663 | A1 | 5/2008 | Lindsley et al. |

FOREIGN PATENT DOCUMENTS

| FR | 2 861 073 | 10/2003 |
| WO | WO 2003/053919 | 7/2003 |
| WO | WO 2005/046601 | 5/2005 |
| WO | WO 2006/131711 | 12/2006 |
| WO | WO 20061131713 | 12/2006 |

OTHER PUBLICATIONS

Foster, et al., "Glutamate- and GABA-based CNS therapeutics", Current Opinion in Pharmacology, 2006, vol. 6: pp. 7-17.
International Preliminary Report on Patentability for PCT/GB2006/002035.
International Preliminary Report on Patentability for PCT/GB2006/0022052.
Copending U.S. Appl. No. 11/922,074, filed Jun. 13, 2006, U.S National Stage Entry of PCT/GB06/002156, published as WO 2006/134341.
Copending U.S. Appl. No. 11/991,727, filed Sep. 25, 2006, U.S. National Stage Entry of PCT/GB06/036989, published as WO 2007/041025.
Copending U.S. Appl. No. 12/084,027, filed Oct. 27, 2006, U.S. National Stage Entry of PCT/GB06/041699, published as WO 2007/053400.
Copending U.S. Appl. No. 12/085,340, filed Nov. 23, 2006, U.S. National Stage Entry of PCT/GB06/050411, published as WO 2007/060484.

* cited by examiner

*Primary Examiner*—Shailendra Kumar
(74) *Attorney, Agent, or Firm*—Berard Devlin; Raynard Yuro

(57) ABSTRACT

The present invention provides compounds of formula I:

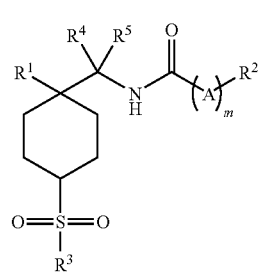

wherein $R^1$ is an alkyl, phenyl, heterocyclyl, cycloalkyl, alkoxy, ester, amino or amide group;
$R^2$ is a phenyl, heterocyclyl, alkyl, cycloalkyl or cycloalkylalkyl group;
$R^3$ is an alkyl, cycloalkyl, cycloalkylalkyl, amino or heterocyclyl group;
$R^4$ and $R^5$ are hydrogen or alkyl or form a cycloalkyl ring;
A is O or N; and
m is zero or one;
as inhibitors of GlyT1 and thus as useful for treating or preventing diseases such as schizophrenia; with the provision of pharmaceutical compositions, first and second medical uses and methods of treatment.

9 Claims, No Drawings

CYCLOHEXANESULFONYL DERIVATIVES AS GLYT1 INHIBITORS TO TREAT SCHIZOPHRENIA

RELATED APPLICATION DATA

This is a divisional application of U.S. application Ser. No. 11/446,735, filed Jun. 5, 2006, now U.S. Pat. No. 7,626,056 which claims priority under 35 U.S.C. 119 to GB Application No. 0511452.5, filed Jun. 6, 2005, GB Application No. 0516787.9, filed Aug. 17, 2005 and GB Application No. 0524968.5, filed Dec. 8, 2005.

BACKGROUND OF THE INVENTION

Schizophrenia is a debilitating psychiatric disorder characterized by a combination of negative (blunted affect, withdrawal, anhedonia) and positive (paranoia, hallucinations, delusions) symptoms as well as marked cognitive deficits. While the etiology of schizophrenia is currently unknown, the disease appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia (Jentsch J D and Roth R H, 1999 Neuropsychopharmacology, 20:201).

Fast glutamatergic transmission in the mammalian central nervous system is primarily mediated by the excitatory amino acid glutamate acting on ionotropic glutamate receptors (iGluRs). The iGluRs are comprised of three major subclasses, including the α-amino-3-hydroxy-5-methyl-4-isoxazolepropionic acid (AMPA), kainate, and NMDA receptor subtypes (Hollmann M and Heinemann S, 1994, Annu. Rev. Neurosci. 17:31). These three subclasses are multimeric ligand-gated cation channels which open in response to glutamate binding to induce a depolarizing excitatory post synaptic current. Molecular cloning has revealed that the NMDA receptor family is composed of two primary subunits, NR1 and NR2. In addition a novel inhibitory subunit which is developmentally regulated termed NR3 has been recently described. A high degree of molecular diversity exists within each set of subunits. To date, only one NR1 subunit gene has been cloned; however, alternative splicing of the NR1 gene can produce eight different subunits. In contrast, 4 genes have been cloned for the NR2 subunit (NR2A, NR2B, NR2C, and NR2D), some of which exhibit alternative splicing (Hollmann M and Heinemann S, 1994, Annu. Rev. Neurosci. 17:31). These multiple subunits form heteromeric glutamate-gated ion channels. While the precise subunit stoichiometry of the naturally occurring receptor remains unknown, both the NR1 and NR2 subunits are required for the expression of functionally active receptor-channel complexes in mammalian expression systems. Activation of the NMDA receptor requires the binding of both glutamate and glycine (Johnson J W and Ascher P, 1987, Nature 325:529). Interestingly, the binding sites for these two co-agonists exist on separate subunits as determined by site-directed mutagenesis studies (Laube B, Hirai H, Sturgess M, Betz H and Kuhse J, 1997, Neuron 18:493). On the NR2A and NR2B subunits, a binding pocket for glutamate is formed by interactions between the N-terminus of the receptor and the extracellular loops. Analogous experiments have placed the glycine binding site in a homologous region of the NR1 subunit (Kuryatov A, Laube B, Betz H and Kuhse J, 1994, Neuron 12:1291). Depending on the actual subunit composition, glutamate and glycine activate the NMDA receptor with EC50 values in the high nanomolar to low micromolar range. In addition, the pore of the NMDA receptor is impermeable to magnesium. Under normal resting conditions, extracellular magnesium can bind to a site within the pore and produce a magnesium block of the channel. This magnesium block imparts a strong voltage dependence to the channel which allows the NMDA receptor to act as a coincidence detector requiring the binding of glutamate, glycine, and the occurrence of postsynaptic depolarization before conducting current. Of particular interest is the finding that the psychotomimetic drugs MK-801, PCP, and ketamine all act as open channel blockers of the NMDA receptor-channel by binding to a site that overlaps with the magnesium binding site. It is apparent that the rich diversity of NMDA receptor subunits and regulatory sites provides for a complex assortment of physiologically and pharmacologically distinct heteromeric receptors making the NMDA receptor an ideal target for the design of novel therapeutic compounds.

The NMDA receptor plays a critical role in a variety of neurophysiological phenomena, including but not limited to synaptic plasticity, cognition, attention and memory (Bliss T and Collingridge W, 1993, Nature 361:31; Morris R G M et al., 1986, Nature 319:774). Psychotomimetic drugs constitute a wide class of drugs including psychomotor stimulants (cocaine, amphetamine), hallucinogens (LSD), and NMDA receptor antagonists (PCP, ketamine). Of these, only the NMDA receptor antagonists appear to elicit a robust induction of the positive, negative, and cognitive symptoms of schizophrenia. Controlled studies of ketamine-induced psychosis in human subjects, as well as observations of symptoms from patients abusing PCP as a recreational drug, have produced a convincing list of similarities between NMDA receptor antagonist-induced psychosis and schizophrenia (Jentsch J D and Roth R H, 1999 Neuropsychopharmacology, 20:201). NMDA-receptor antagonists faithfully mimic the symptoms of schizophrenia to the extent that it is difficult to differentiate the two in the clinic. In addition, NMDA receptor antagonists can exacerbate the symptoms in schizophrenics, and can trigger the re-emergence of symptoms in stable patients. Finally, the finding that NMDA receptor co-agonists such as glycine, D-cycloserine, and D-serine produce benefits in schizophrenic patients implicates NMDA receptor hypofunction in this disorder, and indicate that increasing NMDA receptor activation may provide a therapeutic benefit (Leiderman E et al., 1996, Biol. Psychiatry 39:213, Javitt D C et al., 1994, Am. J. Psychiatry 151:1234, Heresco-Levy U, 2000, Int. J. Neuropsychopharmacol. 3:243, Tsai G et al., 1998, Biol. Psychiatry 44:1081). A large number of studies in animal models lend support to the NMDA hypofunction hypothesis of schizophrenia. Recent generation of a mutant mouse expressing only 5% of normal levels of the NMDA NR1 subunit have shown that this decrease in functional NMDA receptors induces a state very similar to that observed in other animal models of schizophrenia (Mohn A R et al., 1999, Cell 98:427). Besides schizophrenia, dysfunction of glutamatergic pathways has been implicated in a number of disease states in the human central nervous system (CNS) including but not limited to cognitive deficits, dementia, Parkinson disease, Alzheimer disease and bipolar disorder.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses. Clinical trials in which high doses of glycine were administered orally as an add-on to standard neuroleptic therapy showed an improvement of the symptoms of schizophrenia patients (Javitt et al. Int. J. Neuropsychopharmacol. (2001) 4: 385-391). One way to increase synaptic glycine levels without administering exogenous glycine is to inhibit its removal from the synapse. Evidence that this approach would be useful in treating schizophrenia comes from a double-blind placebo controlled study in which sarcosine was administered to patients suffering from schizophrenia, but who were poorly responsive to antipsychotic drugs. A beneficial effect was observed on positive, negative and cognitive symptoms, indicating that inhibition of glycine re-uptake is a reasonable approach to the treatment of schizophrenia.

Two specific glycine transporters, GlyT1 and GlyT2 have been identified and shown to belong to the Na$^+$/Cl$^-$ dependent family of neurotransmitter transporters which includes taurine, γ-aminobutyric acid (GABA), proline, monoamines and orphan transporters (Smith K E et al., 1992, Neuron 8:927; Borowsky B et al., 1993, Neuron 10:851; Liu Q R et al., 1993, J. Biol. Chem. 268:22802; Kim K M et al., 1994, Mol. Pharmacol. 45:608; Morrow J A et al., 1998, FEBS Lett. 439:334; Nelson N, 1998, J. Neurochem. 71:1785). GlyT1 and GlyT2 have been isolated from different species and shown to have only 50% identity at the amino acid level. They also have a different pattern of expression in mammalian central nervous system with GlyT2 being expressed in spinal cord, brainstem and cerebellum and GlyT1 present in these regions as well as forebrain areas such as cortex, hippocampus, septum and thalamus (Smith K E et al., 1992, Neuron 8:927; Borowsky B et al., 1993, Neuron 10:851; Liu Q R et al., 1993, J. Biol. Chem. 268:22802). At the cellular level, GlyT2 has been reported to be expressed by glycinergic nerve endings in rat spinal cord whereas GlyT1 appears to be preferentially expressed by glial cells (Zafra F et al., 1995, J. Neurosci. 15:3952). These expression studies have led to the conclusion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat (Bergeron R et al., 1998, PNAS USA 95:15730; Kinney G et al., 2003, J. Neurosci. 23:7586). Furthermore, NFPS has been reported to enhance pre-pulse inhibition in mice, a measure of sensory gating that is known to be deficient in schizophrenia patients (Kinney G et al., 2003, J. Neurosci. 23:7586). These physiological effects of GlyT1 in forebrain regions together with clinical reports showing the beneficial effects of GlyT1 inhibitor sarcosine in improving symptoms in schizophrenia patients (Tsai and Coyle WO99/52519) indicate that selective GlyT1 uptake inhibitors represent a new class of antipsychotic drugs.

SUMMARY OF THE INVENTION

The present invention is directed to compounds that inhibit the glycine transporter GlyT1 and which are useful in the treatment of neurological and psychiatric disorders associated with glutamatergic neurotransmission dysfunction and diseases in which the glycine transporter GlyT1 is involved.

DETAILED DESCRIPTION OF THE INVENTION

The present invention is directed to compounds of the formula I:

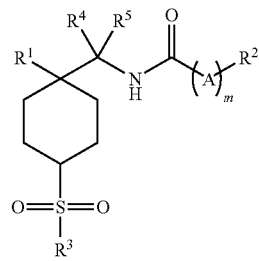

wherein:

$R^1$ is —(CH$_2$)$_n$—R$^{1a}$, wherein n is independently 0-6, and R$^{1a}$ is selected from the group consisting of:
(1) C$_{1-6}$alkyl, which is unsubstituted or substituted with 1-6 halogen, hydroxy,
(2) phenyl substituted with R$^{2a}$, R$^{2b}$ and R$^{2c}$,
(3) heterocycle substituted with R$^{2a}$, R$^{2b}$ and R$^{2c}$,
(4) C$_{3-6}$cycloalkyl, which is unsubstituted or substituted with C$_{1-6}$alkyl, 1-6 halogen, hydroxy or —NR$^{10}$R$^{11}$,
(5) —O—C$_{1-6}$alkyl, which is unsubstituted or substituted with 1-6 halogen, hydroxy or —NR$^{10}$R$^{11}$,
(6) —CO$_2$R$^9$,
  wherein R$^9$ is independently selected from:
  (a) hydrogen,
  (b) —C$_{1-6}$alkyl, which is unsubstituted or substituted with 1-6 fluoro,
  (c) benzyl, and
  (d) phenyl,
(7) —NR$^{10}$R$^{11}$,
  wherein R$^{10}$ and R$^{11}$ are independently selected from:
  (a) hydrogen,
  (b) —C$_{1-6}$alkyl, which is unsubstituted or substituted with hydroxy, 1-6 fluoro or —NR$^{12}$R$^{13}$, where R$^{12}$ and R$^{13}$ are independently selected from hydrogen and —C$_{1-6}$alkyl,
  (c) —C$_{3-6}$cycloalkyl, which is unsubstituted or substituted with hydroxy, 1-6 fluoro or —NR$^{12}$R$^{13}$,
  (d) benzyl,
  (e) phenyl, and
(8) —CONR$^{10}$R$^{11}$;

$R^2$ is selected from the group consisting of:
(1) phenyl, which is substituted with R$^{2a}$, R$^{2b}$ and R$^{2c}$
(2) heterocycle, which is substituted with R$^{2a}$, R$^{2b}$ and R$^{2c}$,
(3) C$_{1-8}$alkyl, which is unsubstituted or substituted with 1-6 halogen, hydroxy, —NR$^{10}$R$^{11}$, phenyl or heterocycle, where the phenyl or heterocycle is substituted with R$^{2a}$, R$^{2b}$ and R$^{2c}$,
(4) C$_{3-6}$cycloalkyl, which is unsubstituted or substituted with 1-6 halogen, hydroxy or —NR$^{10}$R$^{11}$, and
(5) —C$_{1-6}$alkyl-(C$_{3-6}$cycloalkyl), which is unsubstituted or substituted with 1-6 halogen, hydroxy or —NR$^{10}$R$^{11}$;

$R^{2a}$, $R^{2b}$ and $R^{2c}$ are independently selected from the group consisting of:
(1) hydrogen,
(2) halogen,
(3) —$C_{1-6}$alkyl, which is unsubstituted or substituted with:
  (a) 1-6 halogen,
  (b) phenyl,
  (c) $C_{3-6}$cycloalkyl, or
  (d) —$NR^{10}R^{11}$,
(4) —O—$C_{1-6}$alkyl, which is unsubstituted or substituted with 1-6 halogen,
(5) hydroxy,
(6) —$SCF_3$,
(7) —$SCHF_2$,
(8) —$SCH_3$,
(9) —$CO_2R^9$,
(10) —CN,
(11) —$SO_2R^9$,
(12) —$SO_2$—$NR^{10}R^{11}$,
(13) —$NR^{10}R^{11}$,
(14) —$CONR^{10}R^{11}$, and
(15) —$NO_2$,
or two of $R^{2a}$, $R^{2b}$ and $R^{2c}$ are linked to form a

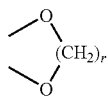

group wherein r is 1 to 3;
$R^3$ is selected from the group consisting of:
(1) $C_{1-6}$alkyl, which is unsubstituted or substituted with 1-6 halogen, hydroxyl, —$NR^{10}R^{11}$, or heterocycle, which is substituted with $R^{2a}$, $R^{2b}$ and $R^{2c}$,
(2) $C_{3-6}$cycloalkyl, which is unsubstituted or substituted with 1-6 halogen, hydroxyl or —$NR^{10}R^{11}$,
(3) —$C_{1-6}$alkyl-($C_{3-6}$cycloalkyl), which is unsubstituted or substituted with 1-6 halogen, hydroxy or —$NR^{10}R^{11}$, and
(4) —$NR^{10}R^{11}$, and
(5) heterocycle, which is substituted with $R^{2a}$, $R^{2b}$ and $R^{2c}$;
$R^4$ and $R^5$ are independently selected from the group consisting of:
(1) hydrogen, and
(2) $C_{1-6}$alkyl, which is unsubstituted or substituted with halogen or hydroxyl, or $R^4$ and $R^5$ taken together form a $C_{3-6}$cycloalkyl ring;
A is selected from the group consisting of:
(1) —O—, and
(2) —$NR^{10}$—;
m is zero or one, whereby when m is zero $R^2$ is attached directly to the carbonyl;

and pharmaceutically acceptable salts thereof and individual enantiomers and diastereomers thereof.
Suitably a and b are each 1 or 2, and preferably a and b are each 2.
In an embodiment, the present invention includes compounds wherein $R^1$ is selected from the group consisting of $(CH_2)_nR^{1a}$ wherein $R^{1a}$ is $C_{3-6}$cycloalkyl, which is unsubstituted or substituted with $R^{2a}$, $R^{2b}$ and $R^{2c}$. In one embodiment, suitably n is 1 and $R^{1a}$ is unsubstituted $C_{3-6}$ cycloalkyl, preferably cyclopropyl. In a further embodiment, suitably n is 0 and $R^{1a}$ is unsubstituted $C_{3-6}$ cycloalkyl, preferably cyclohexyl.

An embodiment of the present invention includes compounds of the formula Ia:

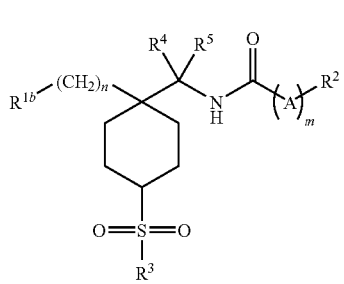

Ia wherein $R^{1b}$ is a $C_{3-6}$ cycloalkyl, which is unsubstituted or substituted with $R^{2a}$, $R^{2b}$ and $R^{2c}$ and $R^2$, $R^{2a}$, $R^{2b}$, $R^{2c}$, $R^3$, $R^4$, $R^5$, A, n and m are defined herein or a pharmaceutically acceptable salt thereof or individual enantiomer or diastereoisomer therefore. Suitably n is 1 and $R^{1b}$ is unsubstituted $C_{3-6}$ cycloalkyl, preferably cyclopropyl.

Further embodiments of the present invention include compounds wherein $R^1$ is heterocycle substituted with $R^{2a}$, $R^{2b}$ and $R^{2c}$. The heterocycle is preferably an unsaturated heterocyclic moiety, for example a nitrogen containing unsaturated heterocycle such as pyridyl and $R^{21}$ and $R^{2b}$ are hydrogen and $R^{2c}$ is hydrogen or fluorine or a saturated heterocyclic moiety, for example a nitrogen containing saturated heterocycle such as piperidyl, optionally substituted by $C_{1-6}$ alkyl.

Thus, a further embodiment of the present invention includes compounds of the formula Ia':

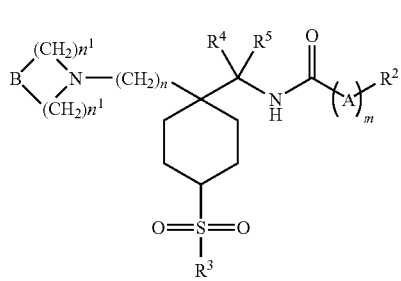

Ia' wherein:
$n^1$ is 0, 1 or 2 and $n^2$ is 1 or 2, the sum of $n^1$ and $n^2$ being 2, 3 or 4
B is oxygen, $NR^{2d}$, $CHR^{2d}$ or a group

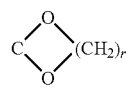

wherein r is 1, 2 or 3 and $R^{2d}$ is selected from the group consisting of:
(1) hydrogen, and
(2) $C_{1-6}$alkyl; preferably methyl, optionally substituted by 1-6 halogen, preferably three fluorine atoms, or
(3) —$SO_2R^9$ wherein $R^9$ is as hereinbefore defined, preferably $C_{1-6}$alkyl such as methyl;
and $R^2$, $R^3$, $R^4$, $R^5$, A n and m are defined herein or a pharmaceutically acceptable salt thereof or an individual enantiomer or diastereomer thereof.

An embodiment of the present invention includes compounds of the formula Ib:

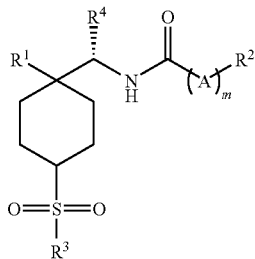

wherein $R^4$ is $C_{1-6}$alkyl, and $R^1$, $R^2$, $R^3$, A and m are defined herein;

or a pharmaceutically acceptable salt thereof or an individual enantiomer or diastereomer thereof.

An embodiment of the present invention includes compounds wherein $R^4$ is $C_{1-3}$alkyl and $R^5$ is hydrogen or $C_{1-3}$alkyl.

Within this embodiment, the present invention includes compounds wherein $R^4$ is $C_{1-3}$alkyl in the (S) configuration and $R^5$ is hydrogen.

Also within this embodiment, the present invention includes compounds wherein $R^4$ is methyl and $R^5$ is hydrogen.

Also within this embodiment, the present invention includes compounds wherein $R^4$ is methyl and $R^5$ is methyl.

Also within this embodiment, the present invention includes compounds wherein $R^4$ is hydrogen and $R^5$ is hydrogen.

An embodiment of the present invention includes compounds wherein m is zero.

Within this embodiment, the present invention includes compounds of the formula Ic:

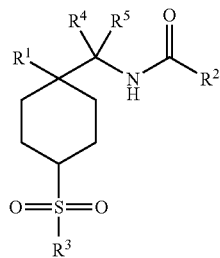

wherein $R^1$, $R^2$, $R^3$, $R^4$ and $R^5$ are defined herein;

or a pharmaceutically acceptable salt thereof or an individual enantiomer or diastereomer thereof.

Further within this embodiment, the present invention includes compounds wherein $R^2$ is selected from the group consisting of:

(1) phenyl, which is substituted with $R^{2a}$, $R^{2b}$ and $R^{2c}$,
(2) heterocycle, such as thienyl, pyridyl or pyrimidinyl, which is substituted with $R^{2a}$, $R^{2b}$ and $R^{2c}$,
(3) $C_{1-8}$alkyl, which is unsubstituted or substituted with 1-6 halogen, phenyl or —$NR^{10}R^{11}$, where the phenyl is substituted with $R^{2a}$, $R^{2b}$ and $R^{2c}$,
(4) $C_{3-6}$cycloalkyl, which is unsubstituted or substituted with 1-6 halogen, hydroxy or —$NR^{10}R^{11}$, and $R^{2a}$, $R^{2b}$ and $R^{2c}$ are independently selected from the group consisting of:

(1) hydrogen,
(2) halogen,
(3) —$C_{1-6}$alkyl,
(4) —O—$C_{1-6}$alkyl,
(5) —$CF_3$,
(6) —$OCF_3$,
(7) —$OCHF_2$,
(8) —$SCF_3$,
(9) —$SCHF_2$,
(10) —$NH_2$, and
(11) —$NMe_2$.

Also further within this embodiment, the present invention includes compounds wherein $R^2$ is phenyl, pyridyl, pyrimidinyl or thienyl substituted by $R^{2a}$, $R^{2b}$ and $R^{2c}$ as hereinbefore defined:

Within this embodiment the present invention includes compounds of the formula Id:

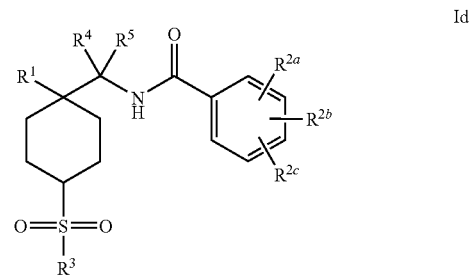

wherein $R^1$, $R^3$, $R^4$ and $R^5$ are defined herein and $R^{2a}$, $R^{2b}$ and $R^{2c}$ are selected from hydrogen, fluoro, chloro, bromo, $OCH_3$, $CF_3$, $OCF_3$ and $NH_2$, and preferably selected from hydrogen, fluoro, chloro, bromo and $CF_3$; and pharmaceutically acceptable salts thereof and individual enantiomers and diastereomers thereof.

Within this embodiment, the present invention includes compounds of the formula Id'

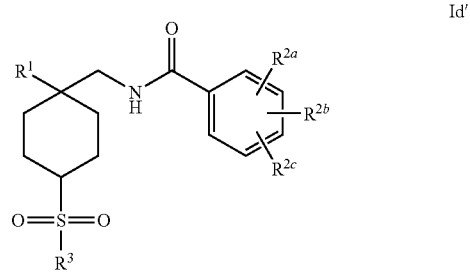

wherein $R^1$, $R^{2a}$, $R^{2b}$, $R^{2c}$ and $R^3$ are defined herein; and pharmaceutically acceptable salts thereof and individual enantiomers and diastereomers thereof.

Also within this embodiment, the present invention includes compounds of the formula Id":

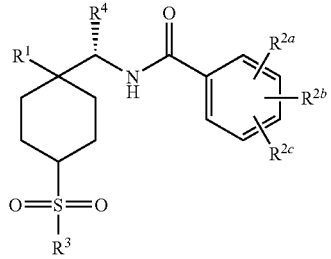

wherein $R^1$, $R^{2a}$, $R^{2b}$, $R^{2c}$, $R^3$ and $R^4$ are defined herein;

and pharmaceutically acceptable salts thereof and individual enantiomers and diastereomers thereof.

Also within this embodiment, the present invention includes compounds of the formula Id''':

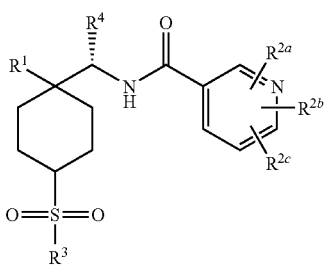

wherein $R^1$, $R^{2a}$, $R^{2b}$, $R^{2c}$, $R^3$ and $R^4$ are defined herein;

and pharmaceutically acceptable salts thereof and individual enantiomers and diastereomers thereof.

An embodiment of the present invention includes compounds wherein $R^3$ is a group $R^{3a}$ and $R^{3a}$ is a heterocycle as defined herein which is substituted with $R^{2a}$, $R^{2b}$ and $R^{2c}$. Preferred heterocyclic groups $R^{3a}$ include unsaturated heterocycles. Preferably the unsaturated heterocyle will be a six-membered ring containing one or more nitrogen atoms, for example pyridine, or a five-membered ring containing a sulphur or oxygen atom or one to three nitrogen atoms.

Most suitably $R^{3a}$ is a five-membered unsaturated heterocycle having one, two or three hetero atoms selected from one, two or three nitrogen atoms and additionally optionally an oxygen or sulphur atom that is linked to the sulphonyl group through one of the heterocycle's carbon atoms.

Preferably $R^{3a}$ is a group

wherein at least one of X, Y and Z is nitrogen and one of the other groups is nitrogen, the third position being carbon; and $R^{3b}$ is hydrogen or $C_{1-6}$alkyl, preferably methyl or $R^{3a}$ is pyridine.

Most preferably $R^{3a}$ is a group:

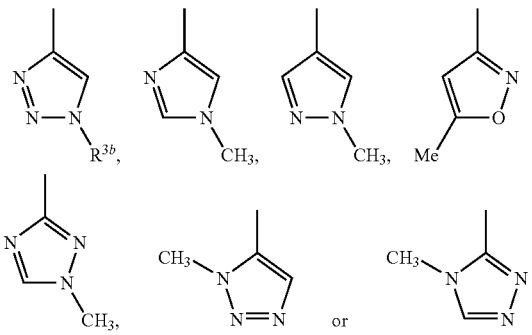

and $R^{3b}$ is hydrogen or methyl.

The unsaturated heterocycle may be unsubstituted or substituted by one or two halogen atoms or $C_{1-6}$ alkyl or $C_{1-6}$ haloalkyl groups. Preferably the unsaturated heterocycle is unsubstituted or substituted with one or two methyl or ethyl groups.

In another embodiment, $R^3$ is a $C_{1-4}$ alkyl group optionally substituted by a cyclopropyl group or a group $NR^{14}R^{15}$ wherein $R^{14}$ is hydrogen or a $C_{1-6}$ alkyl group and $R^{15}$ is a $C_{1-6}$ alkyl group or $R^{14}$ and $R^{15}$ together with the nitrogen atom to which they are attached form a four to six membered heterocyclic ring.

A preferred group of compounds of the formula (I) is that of the formula Ie:

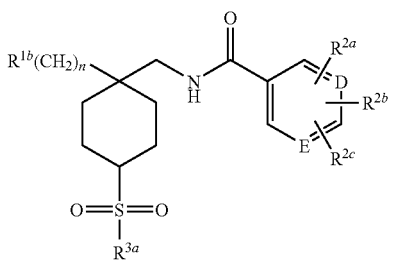

Wherein n, $R^{1b}$ and $R^{2a}$, $R^{2b}$ and $R^{2c}$ are as hereinbefore defined, D and E are each independently CH or N and $R^{3a}$ is an unsaturated heterocyle optionally substituted by a halogen or a $C_{1-6}$ alkyl or $C_{1-6}$ haloalkyl group.

n is preferably 0 or 1.

Preferred values of $R^{1b}$ are as hereinbefore defined.

$R^{2a}$, $R^{2b}$, $R^{2c}$ are preferably hydrogen, $CF_3$ or halogen, suitably chlorine or fluorine.

Preferably only one of $R^{2a}$, $R^{2b}$, $R^{2c}$ is hydrogen.

In one preferred embodiment D and E are both CH. In a further preferred embodiment, one of D and E is CH and the other is N.

$R^{3a}$ is preferably a six-membered heterocyle containing one or more nitrogen atoms for example pyridine, or a five-membered heterocycle containing a sulphur atom and/or one to three nitrogen atoms and preferably two to three nitrogen atoms, wherein the heterocyclic ring is optionally substituted by one or two halogen atoms or $C_{1-6}$ alkyl or $C_{1-6}$ haloalkyl groups, such as methyl or ethyl.

The heterocycle will preferably be connected to the sulphonyl group through a ring carbon atom.

Preferred heterocycles include five-membered unsaturated heterocycles such as triazolyl, pyrazolyl and imidazolyl.

The substituents on the heterocycle ring may be attached to ring carbon and or ring nitrogen atoms (in the case of nitrogen containing heterocycles).

A further preferred group of compounds of the formula (I) is that of the formula If:

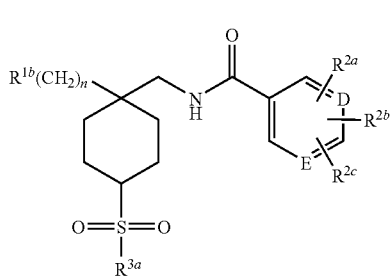

If

Wherein n, $R^{1b}$ and $R^{2a}$, $R^{2b}$ and $R^{2c}$ are as hereinbefore defined, D and E are each independently CH or N, and $R^{3a}$ is a group $CH_2R^{3b}$ wherein $R^{3b}$ is methyl, ethyl or cyclopropyl:

n is preferably 0 or 1.

Preferred values of $R^{1b}$ are as hereinbefore defined.

$R^{2a}$, $R^{2b}$, $R^{2c}$ are preferably hydrogen, $C_{1-6}$alkyl, such as methyl, ethyl and isopropyl and preferably methyl, cyclopropyl, O—$C_{1-6}$alkyl, preferably methoxy, di-$C_{1-6}$alkylamino, preferably dimethylamino, $CF_3$, $OCF_2$ or halogen, suitably chlorine or fluorine. Preferably only one of $R^2$, $R^{2b}$, $R^{2c}$ is hydrogen.

In one preferred embodiment D and E are both CH. In a further preferred embodiment, one of D and E is CH and the other is N.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more chiral centers and can thus occur as racemates and racemic mixtures, single enantiomers, diastereomeric mixtures and individual diastereomers. In the case of those compounds wherein $R^3$ is an alkyl or substituted alkyl group, the $R^1$ group is preferably transequatorial in relation to the group —$SO_2R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyranyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of inhibiting the glycine transporter GlyT1 activity in a patient such as a mammal in need of such inhibition comprising the administration of an effective amount of the compound. The present invention is directed to the use of the compounds disclosed herein as inhibitors of the glycine transporter GlyT1 activity. In addition to primates, especially humans, a variety of other mammals can be treated according to the method of the present invention.

The present invention is further directed to a method for the manufacture of a medicament for inhibiting glycine transporter GlyT1 activity in humans and animals comprising combining a compound of the present invention with a pharmaceutical carrier or diluent.

The subject treated in the present methods is generally a mammal, preferably a human being, male or female, in whom inhibition of glycine transporter GlyT1 activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibiting the glycine transporter activity, in particular GlyT1 activity, may be demonstrated by methodology known in the art. Human placental choriocarcinoma cells (JAR cells (ATCC No. HTB-144)) endogenously expressing GlyT1 were cultured in 96-well Cytostar scintillating microplates (Amersham Biosciences) in RPMI 1640 medium containing 10% fetal calf serum in the presence of penicillin (100 micrograms/milliliter) and streptomycin (100 micrograms/milliliter). Cells were grown at 37° C. in a humidified atmosphere of 5% CO2 for 40-48 hours before the assay. Culture medium was removed from the Cytostar plate, and JAR cells were incubated with 30 microliters of TB1A buffer (120 mM NaCl, 2 mM KCl, 1 mM $CaCl_2$, 1 mM $MgCl_2$, 10 mM HEPES, 5 mM L-alanine, pH 7.5 adjusted with Tris base) with or without the compounds of the present invention for 1 minute. Then 30 microliters of $[^{14}C]$-glycine diluted with TB1A was added to each well to give a final concentration of 10 micromolar. After incubation at room temperature for 3 hours, the Cytostar scintillating microplates were sealed and counted on a Top Count scintillation counter (Packard). Non-specific uptake of $[^{14}C]$-glycine was determined in the presence of 10 mM unlabeled glycine. $[^{14}C]$ taurine uptake experiments were performed according to the same protocol except that 10 mM unlabeled taurine was used to determine non-specific uptake. To determine potencies, a range of concentrations of the compounds of the present invention was added to the cells, followed by the fixed concentration of $[^{14}C]$glycine. The concentration of the present compound that inhibited half of the specific uptake of $[^{14}C]$ glycine ($IC_{50}$ value) was determined from the assay data by non-linear curve fitting.

In particular, the compounds of the following examples had activity in inhibiting specific uptake of $[^{14}C]$glycine in the aforementioned assay, generally with an $IC_{50}$ value of less than about 10 micromolar. Preferred compounds within the present invention had activity in inhibiting specific uptake of $[^{14}C]$glycine in the aforementioned assay with an $IC_{50}$ value of less than about 1 micromolar. These compounds were selective for $[^{14}C]$glycine uptake (by GlyT1 in the JAR cells) compared to $[^{14}C]$taurine uptake (by the taurine transporter TauT in the JAR cells). Such a result is indicative of the intrinsic activity of the compounds in use as inhibitors of GlyT1 transporter activity.

The NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

The compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In a specific embodiment, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In another specific embodiment, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In another specific embodiment, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In another specific embodiment, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-IV-TR. The skilled artisan will recognize that there are alternative nomenclatures, nosologies and classification systems for general medical conditions, and that these systems evolve with medical and scientific progress. Thus the term "obesity or eating disorders associated with excessive food intake" is intended to include like conditions and disorders that are described in other diagnostic sources.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an inhibitor of glycine transporter GlyT1 activity.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art.

In the treatment of conditions which require inhibition of glycine transporter GlyT1 activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. Abbreviations used in the description of the chemistry and in the Examples that follow are:

$CH_2Cl_2$ dichloromethane
DIEA diisopropylethylamine
PS-DIEA polystyrene diisopropylethylamine
PS-DMAP polystyrene 4-N,N-dimethylaminopyridine
DCC polystyrene dicyclohexylcarbodiimide
Ra—Ni Raney Nickel
HOBt hydroxybenzotriazole
THF tetrahydrofuran
TFA trifluoroacteic acid
MeOH methanol
LAH lithium aluminium hydride
KHMDS potassium bis(trimethylsilyl)amide
MsCl methane sulphonyl chloride
WSCDI 1-(3-dimethylaminopropyl)-3-ethylcarbodiimide methiodide Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing methods well known to those skilled in the art for preparing analogous compounds, for example using the reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The compounds of the formula (I) may be prepared by oxidation of the corresponding sulphanyl compound. This oxidation may be carried out with oxone, which is conveniently used as an aqueous solution, in a water miscible inert solvent, for example a ketone such as acetone, at a non-extreme temperature, for example 0 to 150° C. and preferably 50 to 100° C. The sulphanyl compounds may be prepared by the method of Scheme I:

REACTION SCHEME I

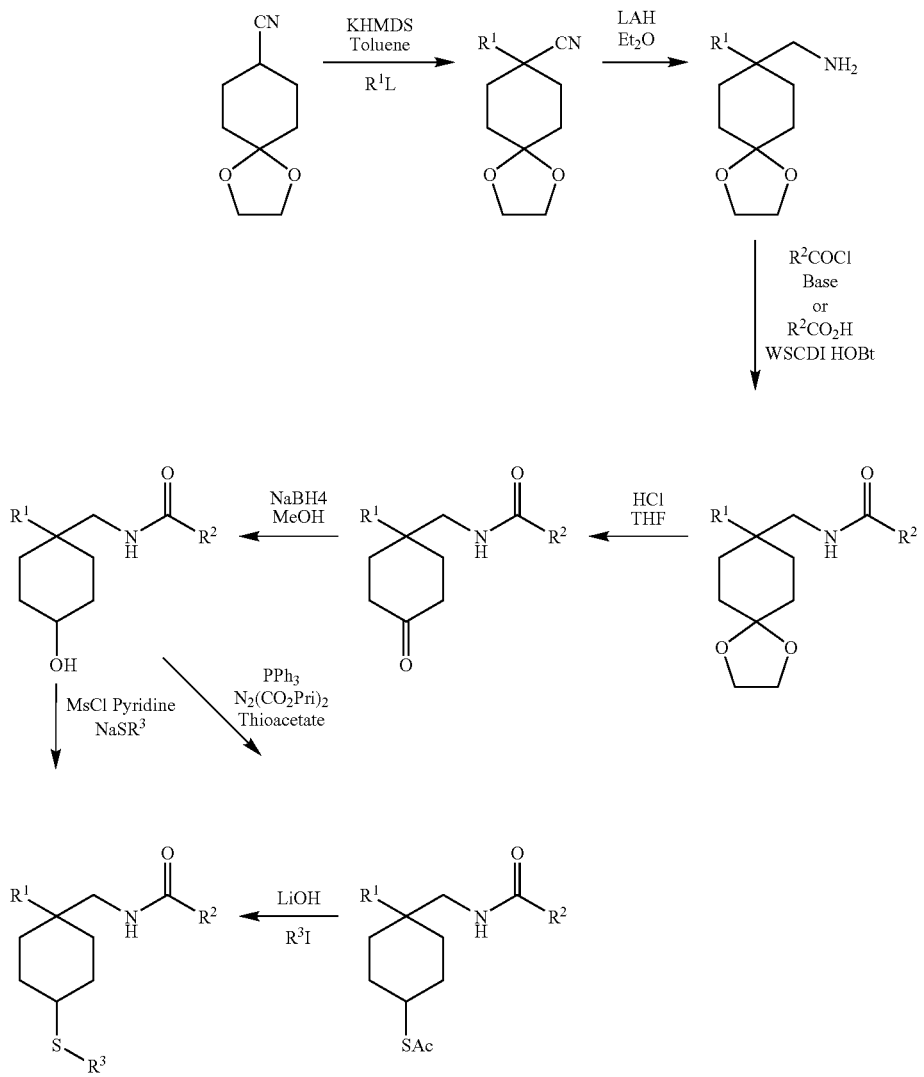

As illustrated in general Reaction Scheme I, dioxaspiro[4.5]decane-8-carbonitrile is reacted with $R^1$ L, where L is a leaving group such as halogen, for example bromine, in the presence of KHDMS, followed by reduction of the nitrile, for example with LAH, to give {[1,4-dioxaspiro[4.4]dec-8-yl]methyl}amine suitably substituted by $R^1$ at the 8-position. This compound is then acylated by reaction with $R^2$ substituted with a reactive carboxylic acid derivative, e.g. an acid chloride, followed by ring opening of dioxa-ring by dilute acid and reduction of the resulting ketone, for example with sodium borohydride. The resulting hydroxyl group is then displaced by a sulhur containing group to give the desired sulphanyl compound, either by reaction with thioacetic acid in the presence of triphenylphosphine and diisopropylazocarboxylate followed by reaction with $R^3I$ in the presence of lithium hydroxide or by reaction with $NaSR^3$ in the presence of mesyl chloride and pyridine.

The compounds of the formula (I) may also be prepared by the reaction of a compound of the formula (II):

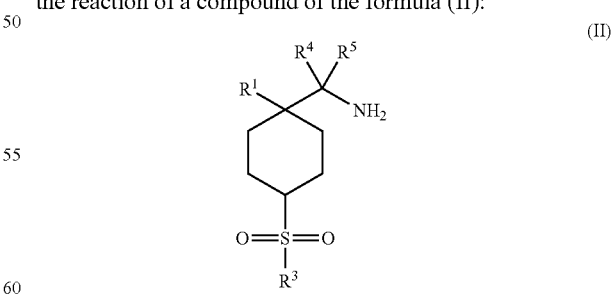

(II)

with the appropriate acid halide of the formula $R^2COhal$, and preferably the appropriate acid chloride. The reaction is suitably carried out in the presence of a weak base such as a trialkylamine, for example ethyldiisopropylamine, in a non polar solvent, for example a halogenated hydrocarbon such as dichloromethane, at a non-extreme temperature, for example −20 to 100° C. and conveniently 0 to 50° C.

The compounds of the formula (II) may be prepared by the method of reaction Scheme II:

REACTION SCHEME II

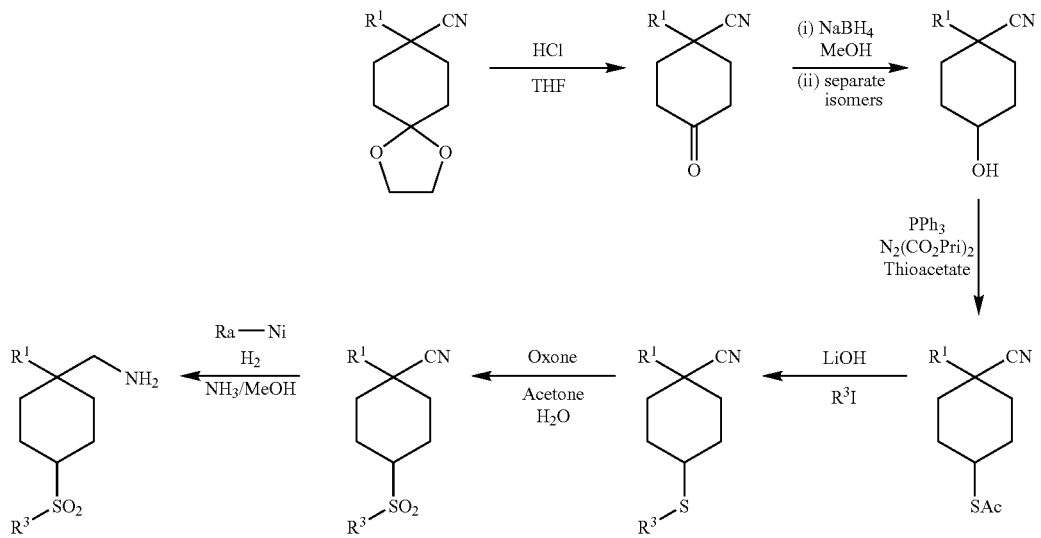

As illustrated in general Reaction Scheme II, a suitably substituted dioxaspiro[4,5]decane-8-carbonitrile is acidified to convert the dioxialane ring to an oxo group followed by reduction of the oxo group with sodium borohydride to give the corresponding hydroxy compound. The hydroxy group is converted to a thioacetate group by reaction with triphenylphosphine/thioacetic acid and the thioacetate group in turn alkylated by a compound $R^3I$ in the presence of lithium hydroxide. Oxygenation by oxone gives the corresponding sulfanoylcyclohexanecarbonitrile. To prepare compounds of the formula (II) wherein $R^4$ and $R^5$ are hydrogen, the nitrile group is reduced, for example by hydrogenation in the presence of a suitable catalyst such as Raney nickel.

The compounds of the formula (II) may also be prepared by the method of reaction Scheme III:

REACTION SCHEME III

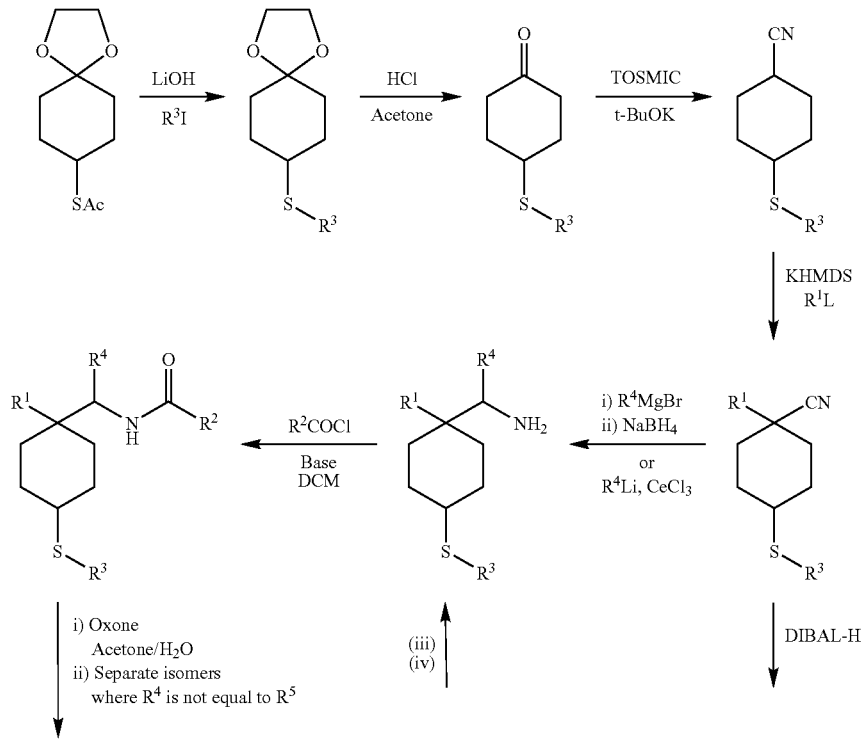

-continued

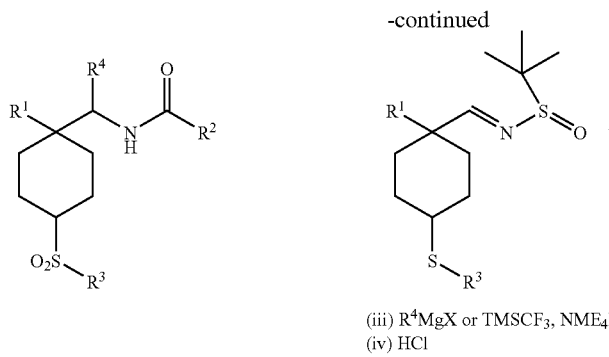

(iii) R⁴MgX or TMSCF₃, NME₄F
(iv) HCl

Compounds of the formula (II) wherein $R^4$ is $C_{1-6}$alkyl and $R^5$ is hydrogen or $C_{1-6}$alkyl may be prepared by general Reaction Scheme III, nucleophilic addition to the suitably substituted cyclohexane thioether carbonitrile is carried out using a Grignard reagent or double nucleophilic addition to the nitrile using an alkyl cerium reagent furnishes the corresponding amine which is acylated as described previously. Chromatographic resolution of the racemate can be carried out under standard conditions.

The following examples serve to illustrate the preparation of compounds of the invention:

EXAMPLE 1

2,4-Dichloro-N-({1-cyclopropylmethyl-4-[(1-methyl-1H-1,2,3-triazol-4-yl)sulfonyl]cyclohexyl}methyl)benzamide (compound 1)

8-(Cyclopropylmethyl)-1,4-dioxaspiro[4.5]decane-8-carbonitrile

To a stirred solution of 1,4-dioxaspiro[4.5]decane-8-carbonitrile (20 g; 119.6136 mmol) and (bromomethyl)cyclopropane (17.76 g 12.6 ml; 131.57 mmol) in THF (100 ml) at −10° C. was added KHMDS (0.5M solution in toluene; 263.15 ml; 131.57 mmol) dropwise and the solution allowed to warm to ambient temperature with stirring for 18 hours. The reaction was cooled in an ice bath and quenched with sat. ammonium chloride solution and the solvent evaporated. The residue was partitioned between EtOAc (300 ml) and water (100 ml adjusted to pH 4 with 1 N HCl). The organic phase was separated, dried over MgSO₄, filtered and evaporated to give an orange oil. (21.0 g) $^1$H NMR δ (ppm) (CDCl₃): 3.99-3.89 (4H, m), 2.08 (2H, d, J=13.5 Hz), 1.96-1.72 (9H, m), 0.96-0.82 (1H, m), 0.59-0.53 (2H, m), 0.17 (2H, q, J=5.1 Hz).

{[8-(Cyclopropylmethyl)-1,4-dioxaspiro[4.5]dec-8-yl]methyl}amine

To a stirred suspension of lithium aluminium hydride (1M solution in ether; 94.9 ml; 94.9 mmol) at −78° C. was added a solution of 8-(cyclopropylmethyl)-1,4-dioxaspiro[4.5]decane-8-carbonitrile (14 g; 63.264 mmol) in ether (40 ml) over 30 minutes and the mixture stirred cold for 1 hour, then allowed to warm to ambient temperature and stirred for 3 hours. The resultant mixture was cooled in an ice bath and to the mixture was added in turn water (2 ml), 15% NaOH solution (2 ml) and water (2 ml). The resultant white granular solid was collected on a filter and rinsed twice with diethyl ether. The filtrate was evaporated to give the crude product as a colourless oil (12 g). $^1$H NMR δ (ppm) (CDCl₃): 3.93 (4H, s), 2.68 (2H, s), 1.63-1.57 (4H, m), 1.54-1.48 (4H, m), 1.25 (2H, d, J=6.6 Hz), 0.65-0.50 (1H, m), 0.46-0.40 (2H, m), 0.02 (2H, q, J=4.9 Hz). MS (m/e)=226.

2,4-Dichloro-N-[(8-cyclopropylmethyl-1,4-dioxaspiro[4.5]dec-8-yl)methyl]benzamide To a solution of {[8-(cyclopropylmethyl)-1,4-dioxaspiro[4.5]dec-8-yl]methyl}amine (7 g; 31.0 mmol) and n-ethyldiisopropylamine (6.45 ml; 37.2 mmol) in DCM (60 ml) at 0° C. was added 2,4-dichlorobenzoyl chloride (4.781 ml; 34.17 mmol) dropwise and the solution stirred for 4 hours warming to ambient temperature. The reaction was partitioned between DCM (50 ml) and water (20 ml). The aqueous phase was extracted with DCM (20 ml) and the combined organics dried over MgSO₄, filtered and evaporated to give a colourless oil which was used in the next step without further purification. (11.5 g) $^1$H NMR δ (ppm) (CDCl₃): 7.67 (1H, d, J=8.3 Hz), 7.43 (1H, d, J=2.0 Hz), 7.32 (1H, dd, J=2.0, 8.4 Hz), 6.25 (1H, s), 3.93 (4H, s), 3.56 (2H, d, J=6.2 Hz), 1.67 (8H, m), 1.33 (2H, d, J=6.7 Hz), 0.75-0.65 (1H, m), 0.51-0.47 (2H, m), 0.05 (2H, q, J=5.0 Hz). MS (m/e)=398

2,4-Dichloro-N-{[1-(cyclopropylmethyl)-4-oxocyclohexyl]methyl}benzamide 2,4-Dichloro-N-[(8-cyclopropylmethyl-1,4-dioxaspiro[4.5]dec-8-yl)methyl]benzamide (11 g; 27.6158 mmol) was dissolved in THF (80 ml) and HCl (2M; 80 ml) and the solution stirred at ambient temperature for 18 hours. The solution was adjusted to pH 9 with 10N NaOH solution and extracted with DCM (2×75 ml). The combined organics were dried (MgSO4) filtered and evaporated to give an oil which was crystallised from EtOAc isohexane as a white solid (8.0 g) $^1$H NMR δ (ppm) (CDCl₃): 7.67 (1 H, d, J=8.3 Hz), 7.44 (1 H, d, J=2.0 Hz), 7.34 (1 H, dd, J=2.0, 8.3 Hz), 6.37 (1 H, s), 3.72 (2 H, d, J=6.4 Hz), 2.57-2.49 (2 H, m), 2.39-2.31 (2 H, m), 1.92-1.80 (4 H, m), 1.43 (2 H, s), 0.77-0.69 (1 H, m), 0.58-0.54 (2 H, m), 0.11 (2 H, q, J=5.0 Hz). MS (m/e)=354.

2,4-Dichloro-N-{[1-(cyclopropylmethyl)-4-hydroxycyclohexyl]methyl}benzamide

To a stirred solution of 2,4-dichloro-N-{[1-(cyclopropylmethyl)-4-oxocyclohexyl]methyl}benzamide (1 g; 2.82 mmol) in ethanol (20 ml) was added in 4 portions over 30 minutes sodium borohydride (0.1495 g; 3.95 mmol) and the solution stirred at ambient temperature for 2 hours. Water (1 ml) was added and the methanol evaporated. The residue was partioned between DCM (50 ml) and water (20 ml). The aqueous phase was extracted with DCM (20 ml) and the combined organics dried over MgSO$_4$, filtered and evaporated to give an oil. The crude product was chromatographed on silica eluted with 20% EtOAc in DCM to give the two isomeric alcohols in approx 1:1 ratio, 350 mg of each isomer as white foamy solids, plus approx 150 mg of mixed fractions.

Less polar alcohol: $^1$H NMR δ (ppm) (CDCl$_3$): 7.67 (1 H, d, J=8.3 Hz), 7.43 (1 H, d, J=2.0 Hz), 7.33 (1 H, dd, J=2.0, 8.3 Hz), 6.27 (1 H, s), 3.71 (1 H, d, J=4.0 Hz), 3.50 (2 H, d, J=6.3 Hz), 1.83 (2 H, dd, J=4.0, 13.1 Hz), 1.72 (2 H, d, J=13.8 Hz), 1.46-1.32 (6 H, m), 0.72-0.66 (1 H, m), 0.52-0.48 (2 H, m), 0.07 (2 H, q, J=5.0 Hz). MS (m/e)=354.

More polar alcohol: $^1$H NMR δ (ppm) (CDCl$_3$): 7.66 (1 H, d, J=8.4 Hz), 7.42 (1 H, d, J=2.0 Hz), 7.32 (1 H, dd, J=2.0, 8.3 Hz), 6.26 (1 H, s), 3.69-3.65 (1 H, m), 3.59 (2 H, d, J=6.1 Hz), 1.83-1.77 (2 H, m), 1.72-1.68 (2 H, m), 1.63-1.59 (2 H, m), 1.39-1.33 (2 H, m), 1.25 (2 H, d, J=6.7 Hz), 0.72-0.64 (1 H, m), 0.51-0.47 (2H, m), 0.04 (2H, m). MS (m/e)=354

2,4-Dichloro-N-({1-cyclopropylmethyl-4-[(1-methyl-1H-1,2,3-triazol-4-yl)thio]cyclohexyl}methyl)benzamide To a solution of 2,4-dichloro-N-{[1-(cyclopropylmethyl)-4-hydroxycyclohexyl]methyl}benzamide (0.1 g; 0.28 mmol; less polar alcohol isomer) in pyridine (5 ml) at 0° C. was added methanesulphonyl chloride (0.035 g 0.024 ml; 0.31 mmol) dropwise and the solution stirred at ambient temperature for 1 hour.

LC/MS indicates complete formation of the mesylate. In a separate flask 4,4'-dithiobis(1-methyl-1H-1,2,3-triazole) (100 mg; 0.44 mmol) in dry ethanol (2 ml) was treated with sodium borohydride (0.017 g; 0.44 mmol) and the mixture stirred for 30 minutes. LC/MS indicates absence of disulfide to give the thiol. The thiol solution was added to the mesylate and the reaction heated at 50° C. for 18 hours. The pyridine was evaporated and the residue co-evaporated with toluene. The solid was partitioned between water (5 ml) and DCM (20 ml) and the organic phase separated, dried over MgSO$_4$, filtered and evaporated to give an oil. The crude product was chromatographed on silica eluting with 10% EtOAc in DCM to give a colourless oil (100 mg) $^1$H NMR δ (ppm) (CDCl$_3$): 7.63 (1H, d, J=8.3 Hz), 7.55 (1H, s), 7.41 (1H, d, J=1.8 Hz), 7.31 (1H, dd, J=1.9, 8.3 Hz), 6.23 (1H, s), 4.09 (3H, s), 3.53 (2H, d, J=6.2 Hz), 3.16-3.10 (1H, m), 1.90-1.86 (2H, m), 1.69 (4H, dd, J=12.2, 20.5 Hz), 1.36 (2H, t, J=12.7 Hz), 1.20 (2H, d, J=6.6 Hz), 0.69-0.61 (1H, m), 0.46 (2H, q, J=5.9 Hz), 0.01 (2H, t, J=4.9 Hz). MS (m/e)=453.

2,4-Dichloro-N-({1-cyclopropylmethyl-4-[(1-methyl-1H-1,2,3-triazol-4-yl)sulfonyl]cyclohexyl}methyl)benzamide To a solution of 2,4-dichloro-N-({1-cyclopropylmethyl-4-[(1-methyl-1H-1,2,3-triazol-4-yl)thio]cyclohexyl}methyl)benzamide (0.1 g; 0.22 mmol) in acetone (5 ml) was added a solution of oxone (0.5 g; 0.66 mmol) in water (1 ml) and the solution heated at reflux for 2 hours. The reaction was diluted with water (5 ml) and adjusted to pH 7 with Na$_2$CO$_3$ solution (2M). The aqueous mixture was extracted with DCM (10 ml) and the organics separated, washed with brine (30 ml), dried over MgSO$_4$ filtered and evaporated to give a white foam (85 mg). $^1$H NMR δ (ppm) (CDCl$_3$): 8.12 (1H, s), 7.57 (1H, d, J=8.3 Hz), 7.40 (1H, d, J=1.9 Hz), 7.30 (1H, dd, J=1.8, 8.3 Hz), 6.24 (1H, d, J=5.9 Hz), 4.21 (3H, s), 3.45 (2H, d, J=6.3 Hz), 3.19-3.13 (1H, m), 2.02 (2H, d, J=11.2 Hz), 1.89-1.79 (4H, m), 1.37-1.30 (2H, m), 1.20 (2H, d, J=6.6 Hz), 0.69-0.61 (1H, m), 0.48 (2H, q, J=5.9 Hz), 0.01 (2H, t, J=4.9 Hz). MS (m/e)=485.

| NAME | MS data |
|---|---|
| 2-Chloro-N-({1-(cyclopropylmethyl)-4-[(1-methyl-1H-pyrazol-4-yl)sulfonyl]cyclohexyl}methyl)-4-(trifluoromethyl)benzamide | 518 |
| 2,4-Dichloro-N-({1-(1-hydroxy-1-methylethyl)-4-[(1-methyl-1H-1,2,3-triazol-4-yl)sulfonyl]cyclohexyl}methyl)benzamide | 489 |
| 2,4-Dichloro-N-({1-(cyclopropylmethyl)-4-[(5-methyl-1,3,4-thiadiazol-2-yl)sulfonyl]cyclohexyl}methyl)benzamide | 502 |

EXAMPLE 2

2,4-Dichloro-N-(4-cyclopropylmethanesulfonyl-1-cyclopropylmethylcyclohexyl-methyl)benzamide (compound 2)

Thioacetic acid 4-cyclopropylmethyl-4-[(2,4-dichlorobenzoylamino)methyl]-cyclohexyl ester To a stirred solution of triphenylphosphine (0.44 g; 1.68 mmol) in THF (20 ml) at 0° C. was added diisopropylazodicarboxylate (0.34 g; 1.68 mmol) and the solution stirred at 0° C. for 90 minutes. To a stirred solution of 2,4-dichloro-N-{[1-(cyclopropylmethyl)-4-hydroxycyclohexyl]methyl}benzamide (0.30 g; 0.84 mmol; less polar alcohol isomer) in THF (10 ml) was added thioacetic acid (0.12 ml; 1.68 mmol). The resulting solution was added dropwise to the triphenylphosphine solution at 0° C. On complete addition, the solution was stirred at 0° C. for 1 hour then allowed to warm to ambient temperature and stirred for 18 hours. The reaction mixture was partitioned between EtOAc (200 ml) and water (100 ml). The organic phase was washed with brine (100 ml), dried over anhydrous sodium sulfate, filtered and evaporated to give a yellow oily solid. The crude product was chromatographed on silica eluted with 10-30% EtOAc in isohexane to give the product contaminated with triphenylphosphine oxide. The contaminated product was chromatographed on silica eluted with 1% EtOAc in dichloromethane to give the desired product as an oil (220 mg). 1H NMR δ (ppm) (CDCl3): 7.66 (1H, d, J=8.4 Hz), 7.43 (1H, d, J=2.1 Hz), 7.34 (1H, dd, J=2.1, 8.4 Hz), 6.26 (1H, s), 3.58 (2H, d, J=6.0 Hz), 3.45-3.52 (1H, m), 2.30 (3H, s), 1.83-1.88 (2H, m), 1.65-1.74 (4H, m), 1.44-1.52 (2H, m), 1.26 (2H, d, J=7.0 Hz), 0.64-0.71 (1H, m), 0.47-0.52 (2H, m), 0.00-0.06 (2H, m).

2,4-Dichloro-N-(1-cyclopropylmethyl-4-cyclopropylmethylsulfanylcyclohexyl-methylbenzamide To a stirred solution of thioacetic acid 4-cyclopropylmethyl-4-[(2,4-dichlorobenzoylamino)methyl]cyclohexyl ester (220 mg; 0.53 mmol) in degassed IPA (3 ml) was added a solution of lithium hydroxide (51 mg; 2.12 mmol) in water (1 ml) and the mixture stirred at ambient temperature for 2 hours. (Bromomethyl)cyclopropane (0.10 ml; 1.06 mmol) was added and the reaction mixture was stirred at ambient temperature for 18 hours. The reaction mixture was evaporated and the residue diluted with EtOAc (50 ml). The organic phase was washed with water (50 ml) and brine (20 ml), dried over anhydrous sodium sulphate, filtered and evaporated to give a yellow oil. The crude product was purified by preparative-plate chromatography on silica eluting with 15% EtOAc in isohexane to give the desired product as a yellow oil (65 mg). 1H NMR δ (ppm) (CDCl3): 7.68 (1H, d, J=8.4 Hz), 7.42 (1H, d, J=2.1 Hz), 7.33 (1H, dd, J=2.1, 8.4 Hz), 6.21-6.23 (1H, m), 3.59 (2H, d, J=6.0 Hz), 2.67-2.79 (1H, m), 2.48 (2H, d, J=7.0 Hz), 1.87-1.92 (2H, m), 1.59-1.76 (4H, m), 1.32-1.41 (2H, m), 1.25 (2H, d, J=6.8 Hz), 0.91-1.02 (1H, m), 0.64-0.75 (1H, m), 0.57 (2H, dd, J=1.2, 7.9 Hz), 0.46-0.49 (2H, m), 0.18-0.28 (2H, m), 0.03-0.04 (2H, m).

2,4-Dichloro-N-(4-cyclopropylmethanesulfonyl-1-cyclopropylmethylcyclohexyl-methyl)benzamide To a stirred solution of 2,4-dichloro-N-(1-cyclopropylmethyl-4-cyclopropylmethylsulfanylcyclohexyl methylbenzamide (65 mg; 0.152 mmol) in acetone (2 ml) was added a solution of oxone (281 mg; 0.457 mmol) in water (2 ml) and the solution heated at reflux for 1 hour. The reaction was diluted with water (8 ml) and adjusted to pH 7 with saturated NaHCO₃ solution. The aqueous mixture was extracted with EtOAc (2×50 ml). The organic layer was dried over anhydrous sodium sulfate, filtered and evaporated to give a colourless oil. The oil was purified by preparative plate chromatography eluting with 10% EtOAc in dichloromethane which give the title compound as a white foam (37 mg). 1H NMR δ (ppm) (CDCl3): 7.66 (1H, d, J=8.3 Hz), 7.43 (1H, d, J=2.0 Hz), 7.34 (1H, dd, J=2.0, 8.3 Hz), 6.21-6.29 (1H, m), 3.62 (2H, d, J=6.4 Hz), 2.84-2.95 (3H, m), 2.04-2.07 (2H, m), 1.87-1.95 (4H, m), 1.35-1.41 (2H, m), 1.13-1.27 (3H, m), 0.66-0.80 (3H, m), 0.48-0.52 (2H, m), 0.40-0.43 (2H, m), 0.04-0.08 (2H, m). MS (m/e)=459.

The following compounds can be prepared by the method of example 2 using the appropriate carboxylic acid/acid chloride:

| Name | MS data |
| --- | --- |
| N-({1-(Cyclopropylmethyl)-4-[(cyclopropylmethyl)sulfonyl]cyclohexyl}methyl)-2,4-bis(trifluoromethyl)pyrimidine-5-carboxamide | 528 |
| N-({1-(Cyclopropylmethyl)-4-[(cyclopropylmethyl)sulfonyl]cyclohexyl}methyl)-4-methyl-2-(trifluoromethyl)pyrimidine-5-carboxamide | 474 |
| 2-Chloro-N-({1-(cyclopropylmethyl)-4-[(cyclopropylmethyl)sulfonyl]cyclohexyl}methyl)-4-fluorobenzamide | 442 |
| 2,6-Dichloro-N-({1-(cyclopropylmethyl)-4-[(cyclopropylmethyl)sulfonyl]cyclohexyl}methyl)nicotinamide | 459 |
| 2,4,6-Trichloro-N-({1-(cyclopropylmethyl)-4-[(cyclopropylmethyl)sulfonyl]cyclohexyl}methyl)benzamide | 492 |
| 2-Chloro-N-({1-(cyclopropylmethyl)-4-[(cyclopropylmethyl)sulfonyl]cyclohexyl}methyl)-4-(trifluoromethyl)benzamide | 492 |
| N-({1-(Cyclopropylmethyl)-4-[(cyclopropylmethyl)sulfonyl]cyclohexyl}methyl)-4-(methylsulfonyl)benzamide | 468 |
| N-({1-(Cyclopropylmethyl)-4-[(cyclopropylmethyl)sulfonyl]cyclohexyl}methyl)-2-(trifluoromethoxy)benzamide | 474 |
| 4-Bromo-2-chloro-N-({1-(cyclopropylmethyl)-4-[(cyclopropylmethyl)sulfonyl]cyclohexyl}methyl)benzamide | 502 |
| 4-Chloro-N-({1-(cyclopropylmethyl)-4-[(cyclopropylmethyl)sulfonyl]cyclohexyl}methyl)-2-methylbenzamide | 438 |
| 2-Chloro-N-({1-(cyclopropylmethyl)-4-[(cyclopropylmethyl)sulfonyl]cyclohexyl}methyl)-4-(methylsulfonyl)benzamide | 502 |
| N-({1-(Cyclopropylmethyl)-4-[(cyclopropylmethyl)sulfonyl]cyclohexyl}methyl)-2,4,6-trimethylbenzamide | 432 |
| N-({1-(Cyclopropylmethyl)-4-[(cyclopropylmethyl)sulfonyl]cyclohexyl}methyl)-2,6-dimethylbenzamide | 418 |
| 2-Chloro-N-({1-(cyclopropylmethyl)-4-[(cyclopropylmethyl)sulfonyl]cyclohexyl}methyl)-6-methylbenzamide | 438 |
| N-({1-(Cyclopropylmethyl)-4-[(cyclopropylmethyl)sulfonyl]cyclohexyl}methyl)-5-(trifluoromethyl)thieno[3,2-b]pyridine-6-carboxamide | 515 |
| 2-Chloro-N-{[1-(cyclopropylmethyl)-4-(propylsulfonyl)cyclohexyl]methyl}-4-(trifluoromethyl)benzamide | 478 |
| N-({1-(Cyclopropylmethyl)-4-[(cyclopropylmethyl)sulfonyl]cyclohexyl}methyl)-2-nitro-4-(trifluoromethyl)benzamide | 503 |
| 2,4-Dichloro-N-({1-(cyclopropylmethyl)-4-[(cyclopropylmethyl)sulfonyl]cyclohexyl}methyl)benzamide | 458 |
| 2,6-Dichloro-N-({1-(cyclopropylmethyl)-4-[(cyclopropylmethyl)sulfonyl]cyclohexyl}methyl)-5-fluoronicotinamide | 477 |
| 2,4-Dichloro-N-{[1-(cyclopropylmethyl)-4-(propylsulfonyl)cyclohexyl]methyl}benzamide | 446 |
| 2,6-Dichloro-N-({1-(cyclopropylmethyl)-4-[(cyclopropylmethyl)sulfonyl]cyclohexyl}methyl)benzamide | 458 |
| 2,4-Dichloro-N-({1-(cyclopropylmethyl)-4-[(cyclopropylmethyl)sulfonyl]cyclohexyl}methyl)-3-fluorobenzamide | 476 |
| N-({1-(Cyclopropylmethyl)-4-[(cyclopropylmethyl)sulfonyl]cyclohexyl}methyl)-2-(methylthio)nicotinamide | 437 |
| N-({1-(Cyclopropylmethyl)-4-[(cyclopropylmethyl)sulfonyl]cyclohexyl}methyl)-4-methyl-6-(trifluoromethyl)nicotinamide | 473 |
| 4-Chloro-N-({1-(cyclopropylmethyl)-4-[(cyclopropylmethyl)sulfonyl]cyclohexyl}methyl)-2-(trifluoromethyl)benzamide | 492 |
| 2,4,6-Trichloro-N-{[1-(cyclopropylmethyl)-4-(propylsulfonyl)cyclohexyl]methyl}benzamide | 480 |

-continued

| Name | MS data |
|---|---|
| 2,4-Dichloro-N-({1-(cyclopropylmethyl)-4-[(cyclopropylmethyl)sulfonyl]cyclohexyl}methyl)-5-fluorobenzamide | 476 |
| 2-Chloro-N-({1-(cyclopropylmethyl)-4-[(cyclopropylmethyl)sulfonyl]cyclohexyl}methyl)-4-nitrobenzamide | 469 |
| 2-Chloro-N-{[1-(cyclopropylmethyl)-4-(ethylsulfonyl)cyclohexyl]methyl}-4-(trifluoromethyl)benzamide | 465 |
| 2-Chloro-N-({1-(cyclopropylmethyl)-4-[(cyclopropylmethyl)sulfonyl]cyclohexyl}methyl)-3-(trifluoromethyl)benzamide | 492 |
| 2-Chloro-N-({1-(cyclopropylmethyl)-4-[(cyclopropylmethyl)sulfonyl]cyclohexyl}methyl)-6-fluorobenzamide | 442 |
| 4-Chloro-N-{[1-(cyclopropylmethyl)-4-(propylsulfonyl)cyclohexyl]methyl}-2-(trifluoromethyl)benzamide | 479 |
| 2-Chloro-N-({1-(cyclopropylmethyl)-4-[(cyclopropylmethyl)sulfonyl]cyclohexyl}methyl)-3,6-difluorobenzamide | 459 |
| N-({1-(Cyclopropylmethyl)-4-[(cyclopropylmethyl)sulfonyl]cyclohexyl}methyl)-2,4-dimethylbenzamide | 418 |
| 2-Chloro-N-({1-(cyclopropylmethyl)-4-[(cyclopropylmethyl)sulfonyl]cyclohexyl}methyl)-6-methylnicotinamide | 439 |
| N-({1-(Cyclopropylmethyl)-4-[(cyclopropylmethyl)sulfonyl]cyclohexyl}methyl)-2-(trifluoromethyl)-1,6-naphthyridine-3-carboxamide | 510 |
| N-({1-(Cyclopropylmethyl)-4-[(cyclopropylmethyl)sulfonyl]cyclohexyl}methyl)-4-methyl-2-oxo-6-(trifluoromethyl)-1,2-dihydropyridine-3-carboxamide | 489 |
| N-({1-(Cyclopropylmethyl)-4-[(cyclopropylmethyl)sulfonyl]cyclohexyl}methyl)-5-methyl-2-(trifluoromethyl)-3-furamide | 462 |
| N-({1-(Cyclopropylmethyl)-4-[(cyclopropylmethyl)sulfonyl]cyclohexyl}methyl)-2-methylbenzamide | 404 |
| 4-Chloro-N-({1-(cyclopropylmethyl)-4-[(cyclopropylmethyl)sulfonyl]cyclohexyl}methyl)-2,5-difluorobenzamide | 459 |
| 2-Chloro-N-({1-(cyclopropylmethyl)-4-[(cyclopropylmethyl)sulfonyl]cyclohexyl}methyl)-6-fluoro-3-methylbenzamide | 456 |
| 4-Chloro-N-({1-(cyclopropylmethyl)-4-[(cyclopropylmethyl)sulfonyl]cyclohexyl}methyl)-2-fluorobenzamide | 442 |
| 2,4-Dichloro-N-{[1-(cyclopropylmethyl)-4-(ethylsulfonyl)cyclohexyl]methyl}benzamide | 432 |
| 4-Bromo-N-({1-(cyclopropylmethyl)-4-[(cyclopropylmethyl)sulfonyl]cyclohexyl}methyl)thiophene-3-carboxamide | 474 |
| 2,5-Dichloro-N-({1-(cyclopropylmethyl)-4-[(cyclopropylmethyl)sulfonyl]cyclohexyl}methyl)thiophene-3-carboxamide | 464 |
| N-({1-(Cyclopropylmethyl)-4-[(cyclopropylmethyl)sulfonyl]cyclohexyl}methyl)-2-(1,1,2,2-tetrafluoroethoxy)benzamide | 506 |
| 2-Chloro-N-({1-(cyclopropylmethyl)-4-[(cyclopropylmethyl)sulfonyl]cyclohexyl}methyl)nicotinamide | 425 |
| 3,5-Dichloro-N-({1-(cyclopropylmethyl)-4-[(cyclopropylmethyl)sulfonyl]cyclohexyl}methyl)pyridine-2-carboxamide | 459 |
| N-({1-(Cyclopropylmethyl)-4-[(cyclopropylmethyl)sulfonyl]cyclohexyl}methyl)-4,6-dimethyl-2-(trifluoromethyl)pyrimidine-5-carboxamide | 488 |
| N-({4-[(cyclopropylmethyl)sulfonyl]-1-ethylcyclohexyl}methyl)-2-methoxy-4-methyl-6-(trifluoromethyl)nicotinamide | 477 |
| N-{[1-(cyclopropylmethyl)-4-(propylsulfonyl)cyclohexyl]methyl}-2-methoxy-4-methyl-6-(trifluoromethyl)nicotinamide | 491 |
| N-{[1-(cyclopropylmethyl)-4-(ethylsulfonyl)cyclohexyl]methyl}-2-methoxy-4-methyl-6-(trifluoromethyl)nicotinamide | 477 |
| 6-chloro-N-({1-(cyclopropylmethyl)-4-[(cyclopropylmethyl)sulfonyl]cyclohexyl}methyl)-2-(trifluoromethyl)nicotinamide | 493 |
| N-{[1-(cyclopropylmethyl)-4-(propylsulfonyl)cyclohexyl]methyl}-2-methyl-6-(trifluoromethyl)nicotinamide | 461 |
| N-{[1-(cyclopropylmethyl)-4-(ethylsulfonyl)cyclohexyl]methyl}-2-methyl-6-(trifluoromethyl)nicotinamide | 447 |
| N-({1-(cyclopropylmethyl)-4-[(cyclopropylmethyl)sulfonyl]cyclohexyl}methyl)-6-methyl-2-(trifluoromethyl)nicotinamide | 473 |
| 2,6-dimethyl-2-methylsulfanyl-pyrimidine-5-carboxylic acid (4-cyclopropylmethanesulfonyl-1-cyclopropylmethyl-cyclohexylmethyl)-amide | 466 |
| 2-chloro-4,6,dimethyl-pyrimidine-5-carboxylic acid (4-cyclopropylmethanesulfonyl-1-cyclopropylmethyl-cyclohexylmethyl)-amide | 454 |
| 2-cyclopropyl-4,6,dimethyl-pyrimidine-5-carboxylic acid (4-cyclopropylmethanesulfonyl-1-cyclopropylmethyl-cyclohexylmethyl)-amide | 460 |
| 2-chloro-N-(4-cyclopropylmethanesulfonyl-1-cyclopropylmethyl-cyclohexylmethyl)-4-pyrazol-1-yl-benzamide | 490 |
| 3-chloro-biphenyl-4-carboxylic acid (4-cyclopropylmethanesulfonyl-1-cyclopropylmethyl-cyclohexylmethyl)-amide | 500 |

EXAMPLE 3

N-(4-Cyclopropylmethanesulfonyl-1-cyclopropylm-ethyl-cyclohexylmethyl)-2-methyl-6-trifluoromethyl-nicotinamide

1,1,2,2,3,3,4,4,4-Nonafluorobutane-1-sulfonic acid 4-cyano-4-cyclopropylmethylcyclohex-1-enyl ester n-Butyllithium (2.5 M in hexanes 33.9 ml, 84.6 mmol) was added dropwise over 15 min to a cooled (0° C.) solution of diisopropylamine (11.9 ml, 84.6 mmol) in tetrahydrofuran (80 ml). On complete addition the pale yellow solution was stirred for 15 minutes then cooled to −78° C. A solution of 1-cyclopropylmethyl-4-oxo-cyclohexanecarbonitrile (15.0 g, 84.6 mmol) in tetrahydrofuran (50 ml) was added dropwise over 30 minutes via a cannula to the cooled solution and the resulting orange solution was stirred for 30 minutes. Neat nonabutylsulfonyl fluoride (25.6 g, 84.6 mmol) was added dropwise over 20 minutes with stirring and the resulting solution was allowed to warm slowly to ambient temperature overnight. The reaction mixture was poured onto ice (200 g) and ethyl acetate (200 ml) was added. The mixture was filtered through celite and the layers separated. The aqueous phase was extracted with ethyl acetate (200 ml) and the organic layers were combined. The organic layer was washed with brine (200 ml), dried over anhydrous sodium sulphate, filtered and evaporated to give an orange oil. The oil was purified by dry flash column chromatography on silica eluting with isohexane on a gradient of dichloromethane (10-30%). Collecting the appropriate fractions gave a pale yellow oil (24.6 g, 79%). 1H NMR δ (ppm) (CDCl$_3$): 5.75 (1H, s), 2.78-2.61 (2H, m), 2.49-2.16 (3H, m), 1.83-1.75 (1H, m), 1.64-1.46 (2H, m), 0.93-0.83 (1H, m), 0.63-0.55 (2H, m), 0.20 (2H, m).

1-Cyclopropylmethyl-4-triisopropylsilanylsulfanyl-cyclohex-3-enecarbonitrile To a degassed, cooled (0° C.) solution of triisopropylsilyl-sulfide (11.1 g, 58.6 mmol) in tetrahydrofuran (60 ml) was added portionwise over 10 minutes sodium hydride (2.34 g, 60% dispersion in oil) and the mixture stirred until a clear solution formed. 1,1,2,2,3,3,4,4,4-Nonafluorobutane-1-sulfonic acid 4-cyano-4-cyclopropylmethylcyclohex-1-enyl ester (26.9 g, 58.6 mmol) was dissolved in anhydrous toluene (170 ml) and degassed for 30 minutes before addition of TIPS sodium sulfide solution and tetrakis triphenylphosphine palladium (0) (3.38 g, 2.93 mmol). On complete addition the mixture was plunged into an oil bath preheated to 90° C. After 15 min the mixture becomes dark brown in colour. After a further 15 min the mixture was allowed to cool to ambient temperature. The mixture was poured on to ice (200 g) and extracted with diethyl ether (2×200 ml). The combined organic layer was washed with water (200 ml), dried over anhydrous sodium sulphate, filtered and evaporated to give a brown oil. The oil was purified by dry flash column chromatography on silica eluting with isohexane on a gradient of dichloromethane (5-30%). Collecting appropriate fractions followed by evaporation gave a brown oil (20.5 g, 100%). 1H NMR δ (ppm) (CDCl$_3$): 5.92 (1H, s), 2.61-2.54 (2H, m), 2.38-2.28 (1H, m), 2.21-2.10 (3H, m), 1.67-1.44 (2H, m), 1.33-1.23 (3H, m), 1.14 (18H, d, J=7.2 Hz), 0.95-0.85 (1H, m), 0.58-0.55 (2H, m), 0.20-0.18 (2H, m).

1-Cyclopropylmethyl-4-cyclopropylmethylsulfanyl-cyclohex-3-enecarbonitrile

To a solution of 1-cyclopropylmethyl-4-triisopropylsila-nylsulfanylcyclohex-3-enecarbonitrile (20.5 g, 58.5 mmol) and (bromomethyl)cyclopropane (15.8 g, 117 mmol) in anhydrous N,N-dimethylformamide (65 ml) was added cesium fluoride (17.8 g, 117 mmol) and the mixture left to stir at ambient temperature for 15 hours. The mixture was diluted with water (500 ml) and extracted with diethyl ether (3×200 ml). The combined organic layer was washed with water (2×300 ml) and brine (200 ml), dried over anhydrous magnesium sulphate, filtered and evaporated to give an orange oil. The oil was purified by dry flash column chromatography on silica eluting with isohexane on a gradient of dichloromethane (10-40%). Collecting appropriate fractions gave a colourless oil (10.7 g, 74%). 1H NMR δ (ppm) (CDCl$_3$): 5.53 (1H, t, J=1.6 Hz), 2.69-2.51 (4H, m), 2.30-2.11 (3H, m), 1.71-1.67 (1H, m), 1.60-1.45 (2H, m), 1.05-0.99 (1H, m), 0.92-0.88 (1H, m), 0.60-0.56 (4H, m), 0.26-0.18 (4H, m).

4-Cyclopropylmethanesulfonyl-1-cyclopropylmeth-ylcyclohex-3-enecarbonitrile A solution of 1-cyclopropylmethyl-4-cyclopropylmethyl-sulfanylcyclohex-3-enecarbonitrile (10.7 g, 43.1 mmol) in acetone (200 ml) was treated with a solution of oxone (79.4 g, 129 mmol) in water (300 ml) and the mixture heated under reflux for 1 h. The mixture was allowed to cool to ambient temperature and the pH of the mixture adjusted to 7 by the addition of saturated sodium hydrogen carbonate solution. The mixture was diluted with water (200 ml) and extracted with ethyl acetate (2×400 ml). The combined organic layer was washed with water (250 ml) and brine (200 ml), dried over anhydrous sodium sulphate, filtered and evaporated to give a white solid (11.2 g, 93%). 1H NMR δ (ppm) (CDCl$_3$): 6.91 (1H, s), 2.98-2.74 (4H, m), 2.66-2.53 (1H, m), 2.42-2.25 (2H, m), 1.71-1.67 (3H, m), 1.13-1.05 (1H, m), 0.97-0.87 (1H, m), 0.73-0.59 (4H, m), 0.45-0.35 (2H, m), 0.23-0.18 (2H, m).

4-Cyclopropylmethanesulfonyl-1-cyclopropylmeth-ylcyclohex-3-enecarbonitrile 4-Cyclopropylmethanesulfonyl-1-cyclopropylmethylcy-clohex-3-enecarbonitrile (11.2 g, 40.1 mmol) was dissolved in methanol (100 ml) and degassed with nitrogen before addition of ammonium formate (25.3 g, 401 mmol) and palladium on carbon (10% w/w, 2.8 g) and the mixture heated under reflux for 80 minutes. The mixture was allowed to cool to ambient temperature then filtered through a glass fibre filter paper. The filtrate was evaporated and the residue was partitioned between ethyl acetate (200 ml) and water (200 ml). The aqueous phase was extracted with ethyl acetate (200 ml). The combined organic layer was washed with brine (100 ml), dried over anhydrous sodium sulfate, filtered and evaporated to give a colourless oil which solidified on standing. The solid obtained was a 9:1 mixture of isomers. The solid was recrystallised from ethyl acetate/isohexane which gave the desired product as a white solid (7.0 g, 62%). 1H NMR δ (ppm) (CDCl$_3$): 2.91-2.85 (3H, m), 2.34-2.23 (4H, m), 2.04-1.94 (2H, m), 1.48 (2H, d, J=6.9 Hz), 1.40-1.32 (2H, m), 1.23-1.13 (1H, m), 0.91-0.85 (1H, m), 0.78-0.74 (2H, m), 0.61-0.57 (2H, m), 0.42 (2H, q, J=5.3 Hz), 0.18 (2H, q, J=5.3 Hz).

C-(4-Cyclopropylmethanesulfonyl-1-cyclopropylmethylcyclohexyl)methylamine

A cooled (0° C.) solution of 4-cyclopropylmethanesulfonyl-1-cyclopropylmethylcyclohex-3-enecarbonitrile (3.5 g, 12.4 mmol) in tetrahydrofuran (10 ml) was treated with borane tetrahydrofuran complex (1M in tetrahydrofuran, 62 ml) dropwise over 20 min. On complete addition the mixture was allowed to warm to ambient temperature and stirred for 4 hours. The solution was cooled to 0° C. and quenched by the slow addition onto cooled (0° C.) methanol (30 ml). On complete addition concentrated hydrochloric acid (3.5 ml) was added and the mixture was allowed to warm to ambient temperature and stirred for 1 hour. The solvent was evaporated and the residue azeotroped with toluene to give a white solid. The solid was dissolved in methanol:dichloromethane (1:1) and purified using an SCX cartridge. The product was washed with methanol then eluted with 2M ammonia in methanol and evaporated to give the desired product as a colourless oil (2.87 g, 81%). 1H NMR δ (ppm) ($d^6$-DMSO): 3.21 (2H, s), 3.05-2.98 (3H, m), 2.62 (2H, s), 1.88-1.84 (2H, m), 1.80-1.74 (2H, m), 1.60-1.53 (2H, m), 1.28-1.22 (2H, m), 1.15 (2H, d, J=6.7 Hz), 1.10-1.02 (1H, m), 0.64-0.62 (3H, m), 0.43-0.36 (4H, m), 0.13-0.06 (2H, m).

N-(4-Cyclopropylmethanesulfonyl-1-cyclopropylmethyl-cyclohexylmethyl)-2-methyl-6-trifluoromethyl-nicotinamide To a stirred solution of C-(4-cyclopropylmethanesulfonyl-1-cyclopropylmethyl-cyclohexyl)-methylamine (200 mg; 0.701 mmol) and N-ethyldiisopropylamine (0.15 ml; 0.841 mmol) in DCM (5 ml) was added 2-methyl-6-(trifluoromethyl)nicotinoyl chloride (172 mg; 0.771 mmol). The mixture was stirred for 90 minutes. Water (4 ml) and DCM (4 ml) were added and the mixture was stirred vigorously for 5 minutes then passed through a PTFE separation frit. The organic phase was collected and evaporated in vacuo to give an oil. The crude product was chromatographed on silica eluted with 15% EtOAc in DCM to give a yellow oil, which still contained impurities. The oil was rechromatographed on silica eluted with 20% EtOAc in DCM to give a yellow oil. The oil was crystallised from EtOAC using hexane to give a white solid (170 mg). 1H NMR (500 MHz, CDCl3): δ 7.82 (1H, d, J 7.8), 7.55 (1H, d, J 7.9), 5.90 (1H, t, J 6.0), 3.61 (2H, d, J 6.4), 2.98-2.88 (3H, m), 2.72 (3H, s), 2.07-1.85 (6H, m), 1.43-1.37 (2H, m), 1.24 (2H, d, J 6.6), 1.20-1.12 (1H, m), 0.77-0.69 (3H, m), 0.54-0.50 (2H, m), 0.42-0.40 (2H, m), 0.06-0.04 (2H, m). MS (m/e)=473. MPt=148-151° C.

EXAMPLE 4

3-Chloro-5-trifluoromethyl-pyridine-2-carboxylic acid (4-cyclopropylmethanesulfonyl-1-cyclopropylmethyl-cyclohexylmethyl)-amide To a stirred solution of C-(4-cyclopropylmethanesulfonyl1-1-cyclopropylmethyl-cyclohexyl)-methylamine (64 mg; 0.224 mmol) in DCM (1 ml) were added 1-(3-dimethylaminopropyl)-3-ethylcarbodiimide methiodide (100 mg; 0.336 mmol), 1-hydroxybenzotriazole hydrate (5 mg; 0.0336 mmol), and 3-chloro-5-trifluoromethyl)pyridine-2-carboxylic acid (65 mg; 0.288 mmol). The mixture was stirred for 20 hours. Water (5 ml) and DCM (5 ml) were added and the mixture was stirred vigorously for 5 minutes then passed through a PTFE separation frit. The organic phase was collected and evaporated in vacuo. The residue was dissolved in MeOH and passed through a Si-carbonate cartridge, eluting with MeOH. The filtrate was evaporated in vacuo to give an oil. The crude product was purified by prep. TLC eluted with 50% EtOAc in hexane to give a colourless oil. The oil was crystallised from EtOAC using hexane to give a white solid (57 mg). 1H NMR (400 MHz, CDCl3): δ 8.72 (1H, s), 8.07 (1H, s), 7.80 (1H, t, J 6.5), 3.60 (2H, d, J 6.6), 2.94-2.88 (3H, m), 2.09-2.05 (2H, m), 2.00-1.86 (4H, m), 1.41-1.35 (2H, m), 1.26-1.16 (3H, m), 0.78-0.70 (3H, m), 0.56-0.52 (2H, m), 0.44-0.40 (2H, m), 0.09-0.07 (2H, m). MS (n/e)=493.

EXAMPLE 5

2-Chloro-N-(4-cyclopropylmethanesulfonyl-1-cyclopropylmethylcyclohexylmethyl)-6-trifluoromethylnicotinamide 2-Chloro-4-(trifluoromethyl)nicotinic acid (348 mg, 1.54 mmol) was suspended in thionyl chloride (2 ml) and heated under reflux for 30 minutes. The solution was allowed to cool to ambient temperature then evaporated. The residue was azeotroped with toluene (2×5 ml) and the residue dissolved in dichloromethane (5 ml). The pale yellow solution was added slowly to a solution of N,N-diisopropylethylamine (226 mg, 1.75 mmol) and C-(4-cyclopropylmethanesulfonyl-1-cyclopropylmethylcyclohexyl)methylamine (400 mg, 1.4 mmol) in dichloromethane (30 ml) and the mixture left to stir at ambient temperature for 30 minutes. Water (50 ml) and dichloromethane (50 ml) were added and the layers separated. The aqueous phase was further extracted with dichloromethane (50 ml) and the organic layers combined, dried over anhydrous sodium sulfate, filtered and the filtrate evaporated to give a pale yellow oil. The oil was purified by flash column chromatography on silica eluting with dichloromethane on a gradient of ethyl acetate (5-10%). Collecting the appropriate fractions followed by evaporation gave a white foam (567 mg, 82%). 1H NMR δ (ppm) (CDCl$_3$): 8.29 (1H, d, J=7.8 Hz), 7.73 (1H, d, J=7.8 Hz), 6.49 (1H, s), 3.66 (2H, d, J=6.2 Hz), 2.98-2.89 (3H, m), 2.07-1.88 (6H, m), 1.43-1.37 (2H, m), 1.28 (2H, d, J=6.6 Hz), 1.22-1.14 (1H, m), 0.77-0.69 (3H, m), 0.53 (2H, q, J=5.9 Hz), 0.42 (2H, q, J=5.2 Hz), 0.06 (2H, q, J=4.8 Hz). MS (m/e)=493.

EXAMPLE 6

N-(4-Cyclopropylmethanesulfonyl-1-cyclopropylmethylcyclohexylmethyl)-2-methoxy-6-trifluoromethylnicotinamide A solution of 2-chloro-N-(4-cyclopropylmethanesulfonyl-1-cyclopropylmethylcyclohexylmethyl)-6-trifluoromethylnicotinamide (50 mg, 0.10 mmol) in methanol (5 ml) was treated with sodium methoxide (11 mg, 0.20 mmol) and the mixture was allowed to stir at ambient temperature for 1 hour then heated under reflux for 4 hours. Water (1 ml) was added and the solvent evaporated. The residue was partitioned between dichloromethane (5 ml) and water (5 ml) and the layers separated using a 5 micron PTFE frit and the filtrate was evaporated. The residue was purified by preparative plate chromatography on silica eluting with 10% ethyl acetate in dichloromethane. Collecting the appropriate band followed by trituration of the silica with ethyl acetate, filtration and evaporation gave a colourless oil (47 mg, 95%). 1H NMR δ (ppm) (CDCl$_3$): 8.67 (1H, d, J=7.6 Hz), 7.92 (1H, s), 7.44 (1H, d, J=7.6 Hz), 4.15 (3H, s), 3.65 (2H, d, J=6.1 Hz), 2.94-2.89 (3H, m), 2.07-1.84 (6H, m), 1.40-1.32 (2H, m), 1.25-1.15 (3H, m), 0.78-0.70 (3H, m), 0.57-0.53 (2H, m), 0.42 (2H, q, J=5.3 Hz), 0.07 (2H, q, J=5.0 Hz). MS (m/e)=489.

The following compounds can be prepared by the method of example 6 using the appropriate carboxylic acid/acid chloride:

| Name | MS data |
| --- | --- |
| N-({1-(cyclopropylmethyl)-4-[(cyclopropylmethyl)sulfonyl]cyclohexyl}methyl)-6-methoxy-2-(trifluoromethyl)nicotinamide | 489 |
| N-{[1-(cyclopropylmethyl)-4-(propylsulfonyl)cyclohexyl]methyl}-2-methoxy-6-(trifluoromethyl)nicotinamide | 477 |

EXAMPLE 7

N-(4-Cyclopropylmethanesulfonyl-1-cyclopropylmethylcyclohexylmethyl)-2-methylsulfanyl-6-trifluoromethylnicotinamide A solution of 2-chloro-N-(4-cyclopropylmethanesulfonyl-1-cyclopropylmethylcyclohexylmethyl)-6-trifluoromethylnicotinamide (75 mg, 0.15 mmol) in propan-2-ol (5 ml) was treated with sodium thiomethoxide (21 mg, 0.30 mmol) and the mixture was heated under reflux for 4 hours. Water (1 ml) was added and the solvent was evaporated. The residue was partitioned between dichloromethane (5 ml) and water (5 ml) and the layers were separated using a 5 micron PTFE frit and the filtrate was evaporated. The residue was purified by preparative plate chromatography eluting with 10% ethyl acetate in dichloromethane. Collecting the appropriate band followed by trituration of the silica with ethyl acetate, filtration and evaporation gave a pale yellow foam (74 mg, 97%). 1H NMR δ (ppm) (CDCl$_3$): 8.00 (1H, d, J=7.8 Hz), 7.41 (1H, d, J=7.8 Hz), 6.40 (1H, s), 3.64 (2H, d, J=6.3 Hz), 2.98-2.89 (3H, m), 2.63 (3H, s), 2.09-1.90 (6H, m), 1.46-1.16 (5H, m), 0.79-0.69 (3H, m), 0.55-0.51 (2H, m), 0.45-0.40 (2H, m), 0.09-0.06 (2H, m). MS (m/e)=505.

EXAMPLE 8

N-(4-Cyclopropylmethanesulfonyl-1-cyclopropylmethylcyclohexylmethyl)-2-methylsulfonyl-6-trifluoromethylnicotinamide A solution of N-(4-cyclopropylmethanesulfonyl-1-cyclopropylmethylcyclohexylmethyl)-2-methylsulfanyl-6-trifluoromethylnicotinamide (44 mg, 0.087 mmol) in acetone (2 ml) was treated with a solution of oxone (161 mg, 0.26 mmol) in water (2 ml) and the mixture heated under reflux for 2 hours. The mixture was allowed to cool to ambient temperature and the pH of the mixture adjusted to 7 by the addition of saturated sodium hydrogen carbonate solution. The mixture was diluted with water (5 ml) and extracted with dichloromethane (5 ml). The mixture was separated using a 5 micron PTFE frit and the filtrate was evaporated. The colourless oil was purified by preparative plate chromatography on silica eluting with 10% ethyl acetate in dichloromethane. Collecting the appropriate band, trituration of the silica with ethyl acetate, filtration and evaporation gave a white foam (36 mg, 80%). 1H NMR δ (ppm) (CDCl$_3$): 8.47 (1H, d, J=8.0 Hz), 7.98 (1H, d, J=8.0 Hz), 7.06 (1H, s), 3.65 (2H, d, J=6.0 Hz), 3.48 (3H, s), 2.94-2.89 (3H, m), 2.06-1.91 (6H, m), 1.41-1.35 (2H, m), 1.30 (2H, d, J=6.7 Hz), 1.22-1.15 (1H, m), 0.76-0.66 (3H, m), 0.49-0.41 (4H, m), 0.07 (2H, q, J=4.9 Hz). MS (m/e)=537.

EXAMPLE 9

N-(4-Cyclopropylmethanesulfonyl-1-cyclopropylmethylcyclohexylmethyl)-2-dimethylamino-6-trifluoromethylnicotinamide 2-Chloro-N-(4-cyclopropylmethanesulfonyl-1-cyclopropylmethylcyclohexylmethyl)-6-trifluoromethylnicotinamide (50 mg, 0.10 mmol) was dissolved in 2M dimethylamine in tetrahydrofuran (2 ml, 4 mmol) and heated in a sealed tube at 70° C. for 2 hours. The mixture was allowed to cool to ambient temperature then evaporated. The residue was purified by preparative plate chromatography eluting with 10% ethyl acetate in dichloromethane. Collecting the appropriate band, followed by trituration of the silica with ethyl acetate, filtration and evaporation gave a white foam (49 mg, 96%). 1H NMR δ (ppm) (CDCl$_3$): 8.18 (1H, d, J=7.7 Hz), 7.65 (1H, s), 7.26 (1H, d, J=7.7 Hz), 3.63 (2H, d, J=6.2 Hz), 2.94-2.89 (9H, m), 2.07-1.81 (6H, m), 1.39-1.31 (2H, m), 1.28-1.14 (3H, m), 0.79-0.67 (3H, m), 0.55-0.49 (2H, m), 0.42 (2H, q, J=5.3 Hz), 0.06 (2H, t, J=4.2 Hz). MS (m/e)=503.

EXAMPLE 10

2-Cyclopropyl-N-(4-cyclopropylmethanesulfonyl-1-cyclopropylmethylcyclohexylmethyl)-6-trifluoromethylnicotinamide 2-Chloro-N-(4-cyclopropylmethanesulfonyl-1-cyclopropylmethylcyclohexylmethyl)-6-trifluoromethylnicotinamide (50 mg, 0.10 mmol), cyclopropylboronic acid (44 mg, 0.51 mmol), tricyclohexylphosphine (5.7 mg, 0.02 mmol) and potassium phosphate (75 mg, 0.35 mmol) were dissolved in toluene (1 ml) and water (0.05 ml) and degassed with nitrogen for 5 minutes. Palladium acetate (2.3 mg, 0.01 mmol) was added and the mixture was heated at 100° C. for 5 hours. Palladium acetate (2.3 mg, 0.01 mmol) and tricyclohexylphosphine (5.7 mg, 0.02 mmol) were added and the reaction heated for a further 3 hours. The crude reaction mixture was diluted with dichloromethane (3 ml) and passed through a Phenomonex abw cartridge. The compound was eluted with dichloromethane (10 ml) and the filtrate was evaporated. The residue was purified by preparative plate chromatography on silica eluting with 10% ethyl acetate in dichloromethane. Collecting the appropriate band, trituration of the silica with ethyl acetate, filtration and evaporation gave a colourless oil (15 mg, 30%). 1H NMR δ (ppm) (CDCl$_3$): 7.79 (1H, d, J=7.8 Hz), 7.43 (1H, d, J=7.8 Hz), 6.00 (1H, s), 3.64 (2H, d, J=6.3 Hz), 2.97-2.89 (3H, m), 2.38-2.32 (1H, m), 2.07-1.86 (6H, m), 1.43-1.36 (2H, m), 1.28-1.14 (5H, m), 1.07-1.05 (2H, m), 0.78-0.68 (3H, m), 0.52 (2H, q, J=5.9 Hz), 0.42 (2H, q, J=5.3 Hz), 0.05 (2H, dd, J=0.0, 4.8 Hz). MS (n/e)=499.

The following compounds can be prepared by the method of example 10 using the appropriate carboxylic acid/acid chloride:

| Name | MS data |
| --- | --- |
| 6-cyclopropyl-N-({1-(cyclopropylmethyl)-4-[(cyclopropylmethyl)sulfonyl]cyclohexyl}methyl)-2-(trifluoromethyl)nicotinamide | 499 |

EXAMPLE 11

N-({cis-1-(cyclopropylmethyl)-4-[(cyclopropylmethyl)sulfonyl]cyclohexyl}methyl)-2-methoxy-4-methyl-6-(trifluoromethyl)nicotinamide Methyl 2-methoxy-4-methyl-6-(trifluoromethyl)nicotinate A solution of ethyl 2-chloro-4-methyl-6-(trifluoromethyl)nicotinate (1 g, 3.7 mmol) was formed in methanol (20 mL). Sodium methoxide (808 mg, 17 mmol) was added and the mixture heated at reflux for 6 hours. The solution was cooled to room temperature then poured into water (50 mL) and extracted with ethyl acetate (3×50 mL). Combined organics were dried over magnesium sulphate, filtered and evaporated to a brown oil. Purification by flash column chromatography over silica using a 10% ethyl acetate:90% iso-hexane mixture gave methyl 2-methoxy-4-methyl-6-(trifluoromethyl)nicotinate as a yellow oil: $^1$H NMR (500 MHz, CDCl3): δ 7.13 (1H, s), 4.00 (3H, s), 3.94 (3H, s), 2.36 (3H, s); m/z=250 (M+H$^+$).

2-Methoxy-4-methyl-6-(trifluoromethyl)nicotinic acid

A solution of methyl 2-methoxy-4-methyl-6-(trifluoromethyl)nicotinate (400 mg, 1.6 mmol) was formed in ethanol (10 mL). A solution of potassium hydroxide (400 mg, 7 mmol) in water (10 mL) was added and the mixture heated at 60° C. for 3 hours. The mixture was cooled in an ice-bath and acidified with aqueous hydrochloric acid (2 N) to approximately pH 3 then extracted with ethyl acetate (3×50 mL). Combined organics were dried over magnesium sulphate, filtered and evaporated to give 2-methoxy-4-methyl-6-(trifluoromethyl)nicotinic acid as a brown solid: $^1$H NMR (400 MHz, CDCl3): δ 7.20 (1H, s), 4.09 (3H, s), 2.55 (3H, s); m/z=236 (M+H$^+$).

N-({cis-1-(cyclopropylmethyl)-4-[(cyclopropylmethyl)sulfonyl]cyclohexyl}methyl)-2-methoxy-4-methyl-6-(trifluoromethyl)nicotinamide Thionyl chloride (2 mL) was added to 2-methoxy-4-methyl-6-(trifluoromethyl)nicotinic acid (68 mg, 0.29 mmol) and then the mixture was heated at 60° C. for 1 hour. The mixture was evaporated to dryness, then re-dissolved in dichloromethane (3 mL) and added to a solution of ({cis-1-(cyclopropylmethyl)-4-[(cyclopropylmethyl)sulfonyl]cyclohexyl}methyl)amine (70 mg, 0.25 mmol) and triethylamine (0.1 mL) in dichloromethane (3 mL). This mixture was stirred at room temperature for 1 hour, then purified directly by flash column chromatography over silica using a 15% ethyl acetate:85% dichloromethane mixture to give N-({cis-1-(cyclopropylmethyl)-4-[(cyclopropylmethyl)sulfonyl]cyclohexyl}methyl)-2-methoxy-4-methyl-6-(trifluoromethyl)nicotinamide as a white foam: 1H NMR (500 MHz, CDCl3): δ 7.16 (1H, s), 6.02 (1H, t, J 6.4), 3.99 (3H, s), 3.62 (2H, d, J 6.4), 2.94-2.87 (3H, m), 2.44 (3H, s), 2.09-2.03 (2H, m), 1.99-1.89 (4H, m), 1.40-1.33 (2H, m), 1.24 (2H, d, J 6.7), 1.20-1.13 (1H, m), 0.78-0.68 (3H, m), 0.52-0.50 (2H, m), 0.42 (2H, q, J 5.3), 0.05 (2H, q, J 5.0); m/z=503 (M+H$^+$).

EXAMPLE 12

2,4-dichloro-N-(1-{1-(cyclopropylmethyl)-4-[(cyclopropylmethyl)thio]cyclohexyl}ethyl)benzamide 1,4-dioxaspiro[4.5]dec-8-yl ethanethioate Potassium thioacetate (21.39 g, 187 mmol) was added to a stirred mixture of 1,4-dioxaspiro[4.5]dec-8-yl methanesulfonate (29.5 g, 125 mmol) in DMSO (31.2 ml) and the mixture was heated at 40° C. for 24 h. The mixture was cooled, brine was added and the mixture was extracted with ethyl acetate. The combined organic fractions were washed with brine, dried, and evaporated. The residue was purified by column chromatography on silica gel using a Biotage 65i cartridge, eluting with EtOAc/isohexane to give 1,4-dioxaspiro[4.5]dec-8-yl ethanethioate (17.5 g, 81 mmol, 64.8% yield) as a red oil. 1H NMR (500 MHz, CDCl3): δ 3.92 (4H, s), 3.53 (1H, s), 2.29 (3H, s), 2.00-1.93 (2H, m), 1.77-1.63 (6H, m).

8-[(cyclopropylmethyl)thio]-1,4-dioxaspiro[4.5]decane 1,4-Dioxaspiro[4.5]dec-8-yl ethanethioate (16.3 g, 75 mmol) was added to a stirred mixture of cyclopropylmethyl bromide (20.35 g, 151 mmol) and lithium hydroxide (7.22 g, 301 mmol) in water (15 ml) and 2-Propanol (75 ml) and stirred at room temperature overnight. Brine was added and the mixture was extracted with ethyl acetate. The combined organic fractions were washed with brine, dried, filtered and the solvent was evaporated under reduced pressure to yield crude product which was purified by column chromatography on silica gel using a Biotage 65i cartridge, eluting with EtOAc/isohexane to give 8-[(cyclopropylmethyl)thio]-1,4-dioxaspiro[4.5]decane as a orange oil. (14.1 g, 61.7 mmol, 82% yield).

1H NMR (400 MHz, CDCl3): δ 3.92 (4H, s), 2.82-2.76 (1H, m), 2.47 (2H, d, J 7.0), 2.01-1.97 (2H, m), 1.84-1.80 (2H, m), 1.69 (4H, m), 1.00-0.82 (1H, m), 0.57-0.53 (2H, m), 0.19 (2H, q, J 5.1).

4-[(cyclopropylmethyl)thio]cyclohexanone

8-[(Cyclopropylmethyl)thio]-1,4-dioxaspiro[4.5]decane (14.1 g, 61.7 mmol) was added to a stirred mixture of 1M hydrochloric acid (120 ml, 120 mmol) and acetone (300 ml) and the mixture was stirred at room temperature overnight. The acetone was removed by evaporation and the residue was extracted with ethyl acetate and washed with water, dried and evaporated to yield an oil used unpurified in the next step. 4-[(cyclopropylmethyl)thio]cyclohexanone (11.5 g, 62.4 mmol, 100% yield)

1H NMR (500 MHz, CDCl3): δ 3.13 (1H, s), 2.49-2.43 (4H, m), 2.28-2.22 (2H, m), 2.14 (2H, s), 1.83 (2H, m), 0.95-0.87 (1H, m), 0.51 (2H, m), 0.14 (2H, m).

4-[(cyclopropylmethyl)thio]cyclohexanecarbonitrile

Potassium-t-butoxide (16.10 g, 144 mmol) was added to a stirred, cooled (0° C.) mixture of TOSMIC (15.84 g, 81 mmol) and 4-[(cyclopropylmethyl)thio]cyclohexanone (11.5 g, 62.4 mmol) in DME (125 ml) and the mixture was stirred at room temperature for 3 h. The mixture was cooled, diluted with ethyl acetate, washed with brine, dried, filtered and the solvent was evaporated under reduced pressure. The residue was purified by column chromatography on silica gel using a Biotage 65i cartridge, eluting with EtOAc/isohexane to give two separated isomers. Combined yield of 4-[(cyclopropylmethyl)thio]cyclohexanecarbonitrile (7.1 g, 36.3 mmol, 58.3% yield)

Less polar isomer: 1H NMR (500 MHz, CDCl3): δ 2.77 (1H, m), 2.54-2.46 (3H, m), 2.16-2.08 (4H, m), 1.67 (2H, m), 1.42-1.35 (2H, m), 0.98-0.90 (1H, m), 0.56 (2H, m), 0.19 (2H, m).

More polar isomer: 1H NMR (500 MHz, CDCl3): δ 2.73 (2H, m), 2.41 (2H, d, J 6.9), 1.97 (2H, m), 1.87 (2H, m), 1.70 (4H, m), 0.92-0.84 (1H, m), 0.49 (2H, m), 0.13 (2H, m).

1-(cyclopropylmethyl)-4-[(cyclopropylmethyl)thio]cyclohexanecarbonitrile

4-[(cyclopropylmethyl)thio]cyclohexanecarbonitrile (either isomer) (1.95 g; 10 mmol) was dissolved in THF (10 mL) and cyclopropyl methyl bromide (2.7 g; 20 mmol) was added followed by the dropwise addition of sodium hexamethyldisilazide (2M, 10 mL, 20 mmol). The reaction was stirred for half an hour and then was quenched with brine and extracted into ethyl acetate. The organic layer was dried and product was purified rigorously from its less polar isomer on silica using a Biotage 65i cartridge eluting with EtOAc/isohexane to yield 1-(cyclopropylmethyl)-4-[(cyclopropylmethyl)thio]cyclohexanecarbonitrile as an oil. (2 g, 80%)

1H NMR (360 MHz, CDCl3): δ 2.57-2.41 (3H, m), 2.09 (2H, m), 1.98 (2H, m), 1.70 (2H, m), 1.40 (2H, d, J 6.9), 1.29-1.21 (2H, m), 0.93-0.75 (2H, m), 0.51-0.45 (4H, m), 0.15-0.07 (4H, m).

(1-{1-(cyclopropylmethyl)-4-[(cyclopropylmethyl)thio]cyclohexyl}ethyl)amine 1-(cyclopropylmethyl)-4-[(cyclopropylmethyl)thio]cyclohexanecarbonitrile (2 g; 8.0321 mmol) was dissolved in toluene (30 mL) and methylmagnesium bromide (8.6 ml; 12 mL of a 1.4M solution in 3:1 toluene/hexane) was added and the reaction mixture was heated to reflux for 16 hours. The reaction was cooled to 0C and methanol (12 mL) was added and the mixture was stirred for 15 minutes before adding sodium borohydride (0.315 g; 8.514026 mmol) and stirring for 0.5 hours at room temperature. The reaction was carefully quenched with 1 M hydrochloric acid (24 mL) and then extracted into ethyl acetate and purified using a 40M Biotage cartridge using 5% (2M ammonia in methanol)/DCM to yield (1-{1-(cyclopropylmethyl)-4-[(cyclopropylmethyl)thio]cyclohexyl}ethyl)amine. (1.6 g, 75%)

1H NMR (400 MHz, CDCl3): δ 0.06 (2H, m), 0.18 (2H, m), 0.44 (2H, m), 0.51-0.65 (3H, m), 0.92-0.96 (1H, m), 1.04 (3H, d, J 6.6), 1.17-1.25 (2H, m), 1.43 (4H, m), 1.80-1.86 (3H, m), 2.44 (2H, m), 2.77 (1H), 3.29 (1H, q, J 6.6).

EXAMPLE 13

2,4-dichloro-N-(1-{1-(cyclopropylmethyl)-4-[(cyclopropylmethyl)sulfonyl]cyclohexyl}ethyl)benzamide 2,4-dichloro-N-(1-{1-(cyclopropylmethyl)-4-[(cyclopropylmethyl)thio]cyclohexyl}ethyl)benzamide (1-{1-(cyclopropylmethyl)-4-[(cyclopropylmethyl)thio]cyclohexyl}ethyl)amine (0.1 g; 0.3745 mmol), 2,4-dichlorobenzoyl chloride (0.1174 g; 0.56175 mmol) and triethylamine (0.0567 g; 0.56175 mmol) were dissolved in dichloromethane and stirred for one hour at room temperature. The reaction was evaporated and partitioned between ethyl acetate and saturated bicarbonate solution. The organic layer was dried and evaporated and the residue was purified by silica chromatography using ethyl acetate hexanes to yield 2,4-dichloro-N-(1-{1-(cyclopropylmethyl)-4-[(cyclopropylmethyl)thio]cyclohexyl}ethyl)benzamide. (130 mg, 79%)

2,4-dichloro-N-(1-{1-(cyclopropylmethyl)-4-[(cyclopropylmethyl)sulfonyl]cyclohexyl}ethyl)benzamide 2,4-dichloro-N-(1-{1-(cyclopropylmethyl)-4-[(cyclopropylmethyl)thio]cyclohexyl}ethyl)benzamide (0.12 g; 0.2733 mmol) was dissolved in acetone (2 ml) and a solution of potassium peroxymonosulfate (oxone) (0.504 g; 0.8199 mmol) in water (1 mL) was added. The reaction was heated to reflux for four hours before cooling and extracting with ethyl acetate. The organic layer was washed with brine, dried and evaporated. The residue was purified by column chromatography to yield 2,4-dichloro-N-(1-{1-(cyclopropylmethyl)-4[(cyclopropylmethyl)sulfonyl]cyclohexyl}ethyl)benzamide (45 mg, 35%)

1H NMR (400 MHz, CDCl3): δ 7.59 (1H, d. J 8.3), 7.42 (1H, d, J 1.8), 7.31 (1H, dd, J 1.8, 8.3), 6.26 (1H, d, J 9.7), 4.76-4.70 (1H, m), 2.96-2.86 (3H, m), 2.23-2.16 (1H, m), 2.09 (1H, d, J 9.8), 2.01 (2H, m), 1.82 (2H, m), 1.42 (1H, m), 1.31 (1H, m), 1.21 (5H, m), 0.77-0.67 (3H, m), 0.57-0.53 (1H, m), 0.47 (3H, m), 0.41 (1H, m), 0.1-0.04 (2H, m)

EXAMPLE 14

2-chloro-N-(1-{1-(cyclopropylmethyl)-4-[(cyclopropylmethyl)sulfonyl]cyclohexyl}ethyl)-4-(trifluoromethyl)benzamide (1-{1-(cyclopropylmethyl)-4-[(cyclopropylmethyl)thio]cyclohexyl}ethyl)amine (0.534 g; 2 mmol) was dissolved in dichloromethane (5 mL) and 2-chloro-4-trifluoromethylbenzoyl chloride (0.621 g; 3 mmol) and were added. The reaction was stirred for an hour and the solvent was evaporated to give a residue that was taken up into ethyl acetate and washed with saturated sodium bicarbonate solution. The organic layer was dried and purified by chromatography to give the amide. This was taken up into dichloromethane and treated with chloroperoxybenzoic acid (1.0572 g 1.373 g of 77%; 6 mmol) for one hour before quenching with calcium hydroxide (0.6669 g; 9 mmol). The filtered solution was purified by column chromatography on silica to give 2-chloro-N-(1-{1-(cyclopropylmethyl)-4-[(cyclopropylmethyl)sulfonyl]cyclohexyl}ethyl)-4-(trifluoromethyl)benzamide (0.65 g, 64%).

1H NMR (500 MHz, CDCl3): δ 7.72 (1H, d, J 8.0), 7.68 (1H, s), 7.59 (1H, d, J 8.0), 6.23 (1H, d, J 9.8), 4.78-4.72 (1H, m), 2.97-2.87 (3H, m), 2.26-2.18 (1H, m), 2.09 (1H, m), 2.03 (2H, m), 1.88-1.80 (2H, m), 1.57-1.51 (1H, m), 1.48-1.42 (1H, m), 1.32 (1H, dd, J 5.9, 14.3), 1.24-1.18 (5H, m), 0.79-0.75 (2H, m), 0.72-0.65 (1H, m), 0.58-0.54 (1H, m), 0.48-0.40 (3H, m), 0.11-0.04 (2H, m).

150 mg of this was separated by chiral HPLC into the pure enantiomers.

Enantiomer A: (51 mg)

Enantiomer B: (47 mg)

The following compounds can be prepared by the method of example 14 using the appropriate carboxylic acid/acid chloride:

| Name | MS data |
|---|---|
| N-(1-{1-(Cyclopropylmethyl)-4-[(cyclopropylmethyl)sulfonyl]cyclohexyl}ethyl)-2-methoxy-4-methyl-6-(trifluoromethyl)nicotinamide | 517 |
| N-(1-{1-(Cyclopropylmethyl)-4-[(cyclopropylmethyl)sulfonyl]cyclohexyl}ethyl)-2-methyl-6-(trifluoromethyl)nicotinamide | 487 |
| N-(1-{1-(Cyclopropylmethyl)-4-[(cyclopropylmethyl)sulfonyl]cyclohexyl}ethyl)-2-methoxy-6-(trifluoromethyl)nicotinamide | 503 |

EXAMPLE 15

4-Chloro-N-({cis-1-(cyclopropylmethyl)-4-[(cyclopropylmethyl)sulfonyl]cyclohexyl}methyl)-2-methoxy-6-(trifluoromethyl)nicotinamide 2-Methoxy-6-(trifluoromethyl)nicotinic acid A mixture of 2-chloro-6-(trifluoromethyl)nicotinic acid (2 g, 8.9 mmol) and sodium methoxide (1.9 g, 36 mmol) in methanol (20 mL) was heated at reflux for 48 hours. The mixture was allowed to cool to room temperature then poured into water (50 mL). This was cooled in an ice-bath and acidified with hydrochloric acid (2 N, aq). The resulting precipitate was filtered and dried to give 2-methoxy-6-(trifluoromethyl)nicotinic acid as a white solid (1.1 g): 1H NMR (400 MHz, CDCl3): δ 8.61 (1H, d, J 7.7), 7.48 (1H, d, J 7.7), 4.25 (3H, s).

4-Chloro-2-methoxy-6-(trifluoromethyl)nicotinic acid

A solution of LiTMP was formed by cooling a solution of 2,2,6,6-tetramethylpiperidine (862 mg, 6.1 mmol) in THF (5 mL) to −50° C. then adding a solution of n-butyllithium (2.4 mL of 2.5 M in hexanes, 6.1 mmol) dropwise and stirring the mixture for 10 minutes at −50° C. This solution was then cooled to −78° C. and a solution of 2-methoxy-6-(trifluoromethyl)nicotinic acid (300 mg, 1.35 mmol) in THF (5 mL) was added dropwise. This mixture was stirred at −78° C. for 2 hours then added via cannula to a pre-cooled solution of hexachloroethane (1.44 g, 6.1 mmol) in THF (5 mL) at −50° C. This mixture was allowed to warm to room temperature over 1 hour then poured into water (20 mL), ethyl acetate (100 mL) added, then washed with hydrochloric acid (2 N, aq, 100 mL). The organic phase was dried over magnesium sulphate, filtered and evaporated to give 4-chloro-2-methoxy-6-(trifluoromethyl)nicotinic acid (312 mg) as an orange solid: 1H NMR (360 MHz, CDCl3): δ 7.36 (1H, s), 4.08 (3H, s).

4-Chloro-N-({cis-1-(cyclopropylmethyl)-4-[(cyclopropylmethyl)sulfonyl]cyclohexyl}methyl)-2-methoxy-6-(trifluoromethyl)nicotinamide 4-Chloro-2-methoxy-6-(trifluoromethyl)nicotinic acid (312 mg, 1.2 mmol) was coupled to ({cis-1-(cyclopropylmethyl)-4-[(cyclopropylmethyl)sulfonyl]cyclohexyl}methyl) amine (232 mg, 0.8 mmol) using the method in example 11 to give 4-chloro-N-({cis-1-(cyclopropylmethyl)-4-[(cyclopropylmethyl)sulfonyl]cyclohexyl}methyl)-2-methoxy-6-(trifluoromethyl)nicotinamide (100 mg) as a white solid: 1H NMR (500 MHz, CDCl3): δ 7.33 (1H, s), 5.87 (1H, t, J 6.2), 4.02 (3H, s), 3.62 (2H, d, J 6.4), 2.94-2.88 (3H, m), 2.07-2.05 (2H, m), 1.97-1.89 (4H, m), 1.42-1.35 (2H, m), 1.24 (2H, d, J 7.2), 1.21-1.13 (1H, m), 0.75 (2H, q, J 6.4), 0.72-0.66 (1H, m), 0.53-0.49 (2H, m), 0.42 (2H, q, J 5.3), 0.04 (2H, q, J 4.9); m/z=523 (M+H+).

EXAMPLE 16

N-({cis-1-(Cyclopropylmethyl)-4-[(cyclopropylmethyl)sulfonyl]cyclohexyl}methyl)-2,4-dimethoxy-6-(trifluoromethyl)nicotinamide A solution of 4-chloro-N-({cis-1-(cyclopropylmethyl)-4-[(cyclopropylmethyl)sulfonyl]cyclohexyl}methyl)-2-methoxy-6-(trifluoromethyl)nicotinamide (50 mg, 0.1 mmol) was formed in methanol (5 mL). Sodium methoxide (54 mg, 1 mmol) was added and the mixture heated at reflux for 2 hours. After cooling to room temperature, the mixture was poured into water (20 mL) and extracted with ethyl acetate (2×20 mL). The combined organics were dried over magnesium sulphate, filtered and evaporated to give an oil. Purification by flash column chromatography on silica gel using 15% ethyl acetate in DCM as eluent then recrystallisation from ethyl acetate with hexane gave N-({cis-1-(cyclopropylmethyl)-4-[(cyclopropylmethyl)sulfonyl]cyclohexyl}methyl)-2,4-dimethoxy-6-(trifluoromethyl)nicotinamide (30 mg) as a white solid: 1H NMR (500 MHz, CDCl3): δ 6.93 (1H, s), 5.84 (1H, t, J 6.4), 3.98 (3H, s), 3.93 (3H, s), 3.59 (2H, d, J 6.4), 2.91-2.86 (3H, m), 2.07-2.04 (2H, m), 1.97-1.89 (4H, m), 1.39-1.33 (2H, m), 1.23 (2H, d, J 6.6), 1.20-1.14 (1H, m), 0.75 (2H, q, J 6.4), 0.72-0.66 (1H, m), 0.50 (2H, q, J 5.9), 0.42 (2H, q, J 5.3), 0.04 (2H, q, J 4.9); m/z=519 (M+H+).

EXAMPLE 17

N-({cis-1-(Cyclopropylmethyl)-4-[(cyclopropylmethyl)sulfonyl]cyclohexyl}methyl)-4-(dimethylamino)-2-methoxy-6-(trifluoromethyl)nicotinamide A solution of dimethylamine (2 mL of 2 M in THF) was added to 4-chloro-N-({cis-1-(cyclopropylmethyl)-4-[(cyclopropylmethyl)sulfonyl]cyclohexyl}methyl)-2-methoxy-6-(trifluoromethyl)nicotinamide (50 mg, 0.1 mmol). The mixture was stirred in a sealed tube for 2 hours at room temperature. The solvent was evaporated and the residue was purified flash column chromatography on silica gel using 10% ethyl acetate in DCM as eluent to give N-({cis-1-(cyclopropylmethyl)-4-[(cyclopropylmethyl)sulfonyl] cyclohexyl}methyl)-4-(dimethylamino)-2-methoxy-6-(trifluoromethyl)nicotinamide (40 mg) as a white solid: 1H NMR (500 MHz, CDCl$_3$): δ 6.71 (1H, s), 6.04 (1H, t, J 6.2), 3.92 (3H, s), 3.59 (2H, d, J 6.2), 3.03 (6H, s), 2.93-2.89 (3H, m), 2.05-2.03 (2H, m), 1.97-1.89 (4H, m), 1.37-1.30 (2H, m), 1.25 (2H, d, J 6.6), 1.20-1.12 (1H, m), 0.77-0.69 (3H, m), 0.51 (2H, q, J 5.9), 0.42 (2H, q, J 5.3), 0.05 (2H, q, J 5.3); m/z=532 (M+H+).

EXAMPLE 18

N-({cis-1-(Cyclopropylmethyl)-4-[(cyclopropylmethyl)sulfonyl]cyclohexyl}methyl)-2-ethoxy-4-methyl-6-(trifluoromethyl)nicotinamide Ethyl 2-ethoxy-4-methyl-6-(trifluoromethyl)nicotinate A solution of ethyl 4-methyl-2-oxo-6-(trifluoromethyl)-1,2-dihydropyridine-3-carboxylate (500 mg, 2 mmol) was formed in acetone (20 mL). Iodoethane (0.8 mL, 10 mmol)

and potassium carbonate (277 mg, 2 mmol) were added and the mixture heated at reflux for 18 hours. The mixture was concentrated and partitioned between water (30 mL) and ethyl acetate (30 mL). The organic phase was dried over magnesium sulphate, filtered and evaporated to give an oil. Purification by flash column chromatography on silica gel using 60% ethyl acetate:40% DCM as eluent gave ethyl 2-ethoxy-4-methyl-6-(trifluoromethyl)nicotinate as a colourless oil (450 mg): 1H NMR δ (ppm) (CDCl3): 7.09 (1H, s), 4.46-4.40 (4H, m), 2.36 (3H, s), 1.38 (6H, q, J=7.6 Hz).

N-({cis-1-(Cyclopropylmethyl)-4-[(cyclopropylmethyl)sulfonyl]cyclohexyl}methyl)-2-ethoxy-4-methyl-6-(trifluoromethyl)nicotinamide Ethyl 2-ethoxy-4-methyl-6-(trifluoromethyl)nicotinate was hydrolysed and coupled to ({cis-1-(cyclopropylmethyl)-4-[(cyclopropylmethyl)sulfonyl]cyclohexyl}methyl)amine using the method in example 11 to give N-({cis-1-(cyclopropylmethyl)-4-[(cyclopropylmethyl)sulfonyl]cyclohexyl}methyl)-2-ethoxy-4-methyl-6-(trifluoromethyl)nicotinamide as a white solid: 1H NMR (500 MHz, CDCl3): δ 7.14 (1H, s), 6.05 (1H, br s), 4.46 (2H, q, J 7.0), 3.62 (2H, d, J 6.3), 2.94-2.89 (3H, m), 2.44 (3H, s), 2.07-2.04 (2H, m), 1.98-1.90 (4H, m), 1.39-1.35 (5H, m), 1.25 (2H, d, J 6.7), 1.21-1.16 (1H, m), 0.78-0.70 (3H, m), 0.50 (2H, q, J 6.2), 0.42 (2H, q, J 5.2), 0.04 (2H, d, J 4.7); m/z=517 (M+H$^+$).

EXAMPLE 19

N-({cis-1-(Cyclopropylmethyl)-4-[(cyclopropylmethyl)sulfonyl]cyclohexyl}methyl)-2-isopropoxy-4-methyl-6-(trifluoromethyl)nicotinamide The method in example 18 was repeated using 2-iodopropane instead of iodoethane to give N-({cis-1-(cyclopropylmethyl)-4-[(cyclopropylmethyl)sulfonyl]cyclohexyl}methyl)-2-isopropoxy-4-methyl-6-(trifluoromethyl)nicotinamide as a white solid: 1H NMR (500 MHz, CDCl3): δ 7.11 (1H, s), 6.02 (1H, br s), 5.46-5.40 (1H, m), 3.61 (2H, d, J 6.3), 2.93-2.89 (3H, m), 2.43 (3H, s), 2.07-2.04 (2H, m), 1.99-1.91 (4H, m), 1.40-1.33 (8H, m), 1.27-1.25 (2H, m), 1.23-1.15 (1H, m), 0.76 (2H, q, J 6.4), 0.72-0.66 (1H, m), 0.53-0.49 (2H, m), 0.42 (2H, q, J 5.3), 0.04 (2H, q, J 4.9); m/z=531 (M+H$^+$).

EXAMPLE 20

N-({cis-1-(Cyclopropylmethyl)-4-[(cyclopropylmethyl)sulfonyl]cyclohexyl}methyl)-2-(difluoromethoxy)-4-methyl-6-(trifluoromethyl)nicotinamide Ethyl 2-(difluoromethoxy)-4-methyl-6-(trifluoromethyl)nicotinate A solution of ethyl 4-methyl-2-oxo-6-(trifluoromethyl)-1,2-dihydropyridine-3-carboxylate (500 mg, 2 mmol) was formed in N,N-dimethylformamide (10 mL). Water (0.5 mL), caesium carbonate (977 mg, 3 mmol) and sodium chlorodifluoroacetate (762 mg, 5 mmol) were added and the mixture heated at 100° C. for 2 hours. The mixture was allowed to cool to room temperature then poured into brine (70 mL) and extracted with ethyl acetate (3×70 mL). The combined organics were dried over magnesium sulphate, filtered and evaporated to give an oil. Purification by flash column chromatography on silica gel using 40% ethyl acetate:60% DCM as eluent gave ethyl 2-(difluoromethoxy)-4-methyl-6-(trifluoromethyl)nicotinate as a colourless oil (280 mg): 1H NMR (500 MHz, CDCl3): δ 7.49 (1H, t, J 71.7), 7.36 (1H, s), 4.46 (2H, q, J 7.1), 2.46 (3H, s), 1.41 (3H, t, J 7.1).

N-({cis-1-(Cyclopropylmethyl)-4-[(cyclopropylmethyl)sulfonyl]cyclohexyl}methyl)-2-(difluoromethoxy)-4-methyl-6-(trifluoromethyl)nicotinamide Ethyl 2-(difluoromethoxy)-4-methyl-6-(trifluoromethyl)nicotinate was hydrolysed and coupled to ({cis-1-(cyclopropylmethyl)-4-[(cyclopropylmethyl)sulfonyl]cyclohexyl}methyl)amine using the method in example 111 to give N-({cis-1-(Cyclopropylmethyl)-4-[(cyclopropylmethyl)sulfonyl]cyclohexyl}methyl)-2-(difluoromethoxy)-4-methyl-6-(trifluoromethyl)nicotinamide as a white solid: 1H NMR (500 MHz, CDCl3): δ 7.53 (1H, t, J 71.7), 7.38 (1H, s), 5.99 (1H, br s), 3.64 (2H, d, J 6.3), 2.96-2.89 (3H, m), 2.51 (3H, s), 2.07-2.04 (2H, m), 1.98-1.90 (4H, m), 1.44-1.37 (2H, m), 1.27 (2H, d, J 6.9), 1.22-1.14 (1H, m), 0.76 (2H, q, J 6.4), 0.72-0.66 (1H, m), 0.51 (2H, q, J 5.9), 0.42 (2H, q, J 5.3), 0.06 (2H, q, J 4.9); m/z=539 (M+H$^+$).

EXAMPLE 21

N-({cis-1-(Cyclopropylmethyl)-4-[(cyclopropylmethyl)sulfonyl]cyclohexyl}methyl)-2-(dimethylamino)-4-methyl-6-(trifluoromethyl)nicotinamide Ethyl 2-(dimethylamino)-4-methyl-6-(trifluoromethyl)nicotinate A solution of dimethylamine (5 mL of 2M in THF) was added to ethyl 2-chloro-4-methyl-6-(trifluoromethyl)nicotinate (500 mg, 1.9 mmol) and stirred in a sealed tube for 24 hours. The mixture was partitioned between ethyl acetate (30 mL) and water (30 mL). The organic phase was dried over magnesium sulphate, filtered and evaporated to give ethyl 2-(dimethylamino)-4-methyl-6-(trifluoromethyl)nicotinate as a colourless oil (450 mg): 1H NMR (500 MHz, CDCl3): δ 6.79 (1H, s), 4.39 (2H, q, J 7.1), 3.05 (6H, s), 2.32 (3H, s), 1.39 (3H, t, J 7.1).

N-({cis-1-(Cyclopropylmethyl)-4-[(cyclopropylmethyl)sulfonyl]cyclohexyl}methyl)-2-(dimethylamino)-4-methyl-6-(trifluoromethyl)nicotinamide Ethyl 2-(dimethylamino)-4-methyl-6-(trifluoromethyl)nicotinate was hydrolysed and coupled to ({cis-1-(cyclopropylmethyl)-4-[(cyclopropylmethyl)sulfonyl]cyclohexyl}methyl)amine using the method in example 11 to give N-({cis-1-(cyclopropylmethyl)-4-[(cyclopropylmethyl)sulfonyl]cyclohexyl}methyl)-2-(dimethylamino)-4-methyl-6-(trifluoromethyl)nicotinamide as a white solid: 1H NMR (400 MHz, CDCl3): δ 6.92 (1H, s), 5.88 (1H, br s), 3.60 (2H, d, J 6.3), 3.01 (6H, s), 2.94-2.90 (3H, m), 2.35 (3H, s), 2.07-2.02 (2H, m), 1.97-1.81 (4H, m), 1.42-1.34 (2H, m), 1.20-1.16 (3H, m), 0.76 (2H, q, J 6.4), 0.70-0.66 (1H, m), 0.52-0.40 (4H, m), 0.05-0.00 (2H, m); m/z=516 (M+H$^+$).

EXAMPLE 22

N-({cis-1-(Cyclopropylmethyl)-4-[(cyclopropylmethyl)sulfonyl]cyclohexyl}methyl)-2,4-dimethyl-6-(trifluoromethyl)nicotinamide Ethyl 2,4-dimethyl-6-(trifluoromethyl)nicotinate A solution of ethyl 2-chloro-4-methyl-6-(trifluoromethyl) nicotinate (500 mg, 1.9 mmol) was formed in N,N-dimethylformamide (5 mL) and degassed. Lithium chloride (237 mg, 5.6 mmol), tetramethyltin (0.28 mL, 2 mmol) and bis(triphenylphosphine)palladium(II) dichloride (133 mg, 0.2 mmol) were added and the mixture heated in a sealed tube at 100° C. for 16 hours. The tube was cooled in an ice bath and the internal pressure released in a controlled manner. The mixture was poured into ammonium hydroxide solution (10% aq, 30 mL) and extracted with ethyl acetate (2×30 mL). The combined organic phases were dried over magnesium sulphate, filtered and evaporated to give an oil. Purification by flash column chromatography on silica gel using 10% hexane in DCM as eluent gave ethyl 2,4-dimethyl-6-(trifluoromethyl) nicotinate as a colourless oil (380 mg): 1H NMR (500 MHz, CDCl3): δ 7.38 (1H, s), 4.45 (2H, q, J 7.1), 2.61 (3H, s), 2.41 (3H, s), 1.42 (3H, t, J 7.1).

N-({cis-1-(Cyclopropylmethyl)-4-[(cyclopropylmethyl)sulfonyl]cyclohexyl}methyl)-2,4-dimethyl-6-(trifluoromethyl)nicotinamide Ethyl 2,4-dimethyl-6-(trifluoromethyl)nicotinate was hydrolysed and coupled to ({cis-1-(cyclopropylmethyl)-4-[(cyclopropylmethyl)sulfonyl]cyclohexyl}methyl)amine using the method in example 11 to give N-({cis-1-(cyclopropylmethyl)-4-[(cyclopropylmethyl)sulfonyl]cyclohexyl}methyl)-2,4-dimethyl-6-(trifluoromethyl)nicotinamide as a white solid: 1H NMR (500 MHz, CDCl3): δ 7.38 (1H, s), 5.76 (1H, t, J 6.0), 3.64 (2H, d, J 6.3), 2.98-2.92 (1H, m), 2.88 (2H, d, J 7.1), 2.61 (3H, s), 2.41 (3H, s), 2.07-2.04 (2H, m), 1.99-1.85 (4H, m), 1.44-1.38 (2H, m), 1.24 (2H, d, J 6.3), 1.20-1.12 (1H, m), 0.76 (2H, q, J 6.4), 0.72-0.65 (1H, m), 0.53-0.51 (2H, m), 0.41 (2H, q, J 5.3), 0.04 (2H, q, J 4.9); m/z=487 (M+H+).

The following compounds can be prepared by the method of example 22 using the appropriate amine:

| Name | MS data |
| --- | --- |
| N-{[1-(cyclopropylmethyl)-4-(ethylsulfonyl)cyclohexyl]methyl}-2,4-dimethyl-6-(trifluoromethyl)nicotinamide | 461 |

EXAMPLE 23

N-({cis-1-(Cyclopropylmethyl)-4-[(cyclopropylmethyl)sulfonyl]cyclohexyl}methyl)-4-methyl-2-(2,2,2-trifluoroethoxy)-6-(trifluoromethyl)nicotinamide Ethyl 4-methyl-2-(2,2,2-trifluoroethoxy)-6-(trifluoromethyl)nicotinate A suspension of sodium hydride (1150 mg of 60% in mineral oil, 3.7 mmol) was formed in THF (10 mL) and cooled in an ice bath. 2,2,2-Trifluoroethanol (0.34 mL, 4.7 mmol) was added dropwise, then the mixture was stirred at 0° C. for 5 mins. A solution of ethyl 2-chloro-4-methyl-6-(trifluoromethyl)nicotinate (500 mg, 1.9 mmol) in THF (10 mL) was added and the mixture heated at reflux for 18 hours then cooled to room temperature. The mixture was partitioned between ethyl acetate (100 mL) and water (100 mL). The organic phase was dried over magnesium sulphate, filtered and evaporated to give an oil. Purification by flash column chromatography on silica gel using 40% hexane:60% DCM as eluent gave ethyl 4-methyl-2-(2,2,2-trifluoroethoxy)-6-(trifluoromethyl)nicotinate as a colourless oil (350 mg): 1H NMR (500 MHz, CDCl3): δ 7.24 (1H, s), 4.83-4.77 (2H, q, J 8.3), 4.43 (2H, q, J 7.1), 2.43 (3H, s), 1.38 (3H, t, J 7.1).

N-({cis-1-(Cyclopropylmethyl)-4-[(cyclopropylmethyl)sulfonyl]cyclohexyl}methyl)-4-methyl-2-(2,2,2-trifluoroethoxy)-6-(trifluoromethyl)nicotinamide Ethyl 4-methyl-2-(2,2,2-trifluoroethoxy)-6-(trifluoromethyl)nicotinate was hydrolysed and coupled to ({cis-1-(cyclopropylmethyl)-4-[(cyclopropylmethyl)sulfonyl]cyclohexyl)}methyl)amine using the method in example 11 to give N-({cis-1-(cyclopropylmethyl)-4-[(cyclopropylmethyl)sulfonyl]cyclohexyl)}methyl)-4-methyl-2-(2,2,2-trifluoroethoxy)-6-(trifluoromethyl)nicotinamide as a white solid: 1H NMR (500 MHz, CDCl3): δ 7.28 (1H, s), 5.94 (1H, br s), 4.82 (2H, q, J 8.4), 3.63 (2H, d, J 6.3), 2.95-2.88 (3H, m), 2.47 (3H, s), 2.06-2.03 (2H, m), 1.98-1.88 (4H, m), 1.41-1.35 (2H, m), 1.23-1.15 (3H, m), 0.76 (2H, q, J 6.3), 0.69-0.65 (1H, m), 0.49 (2H, d, J 7.4), 0.42 (2H, q, J 5.2), 0.02 (2H, d, J 4.7); m/z=571 (M+H+).

EXAMPLE 24

6-Cyano-N-({1-(cyclopropylmethyl)-4-[(cyclopropylmethyl)sulfonyl]cyclohexyl}methyl)-2-(trifluoromethyl)nicotinamide A mixture of 6-chloro-N-({1-(cyclopropylmethyl)-4-[(cyclopropylmethyl)sulfonyl]cyclohexyl}methyl)-2-(trifluoromethyl)nicotinamide (37 mg, 0.076 m-mol), zinc cyanide (44 mg, 0.38 mmol) and tetrakis triphenylphosphine palladium (0) (8.7 mg, 0.008 mmol) in N,N-dimethylformamide (1.5 mL) was heated at 150° C. for 600 s under microwave irradiation. The mixture was allowed to cool to ambient temperature, the supernatant layer removed and evaporated. The residue was partitioned between dichloromethane (5 ml) and water (5 ml) and stirred vigorously for 5 min. The mixture separated using a 5 micron PTFE frit and the filtrate was evaporated. The yellow oil was purified by preparative plate chromatography eluting with 10% ethyl acetate in dichloromethane. Collecting the appropriate band followed by trituration with ethyl acetate, filtration of the solid and evaporation of the filtrate gave a white solid. The solid was recrystallised from ethyl acetate/isohexane which gave 6-cyano-N-({1-(cyclopropylmethyl)-4-[(cyclopropylmethyl)sulfonyl]cyclohexyl}methyl)-2-(trifluoromethyl)-nicotinamide a white solid (21 mg, 57%): 1H NMR (400 MHz, CDCl3) δ 8.11 (1H, d, J=7.9 Hz), 7.95 (1H, d, J=7.9 Hz), 5.98 (1H, s), 3.61 (2H, d, J=6.3 Hz), 2.98-2.88 (3H, m), 2.04-2.01 (2H, m), 1.96-1.84 (4H, m), 1.43-1.37 (2H, m), 1.24 (2H, d, J=6.7 Hz), 1.18-1.12 (1H, m), 0.76 (2H, q, J=6.4 Hz), 0.68-0.64 (1H, m), 0.53-0.49 (2H, m), 0.41 (2H, q, J=5.3 Hz), 0.06-0.05 (2H, m); m/z=484 (M+H+).

EXAMPLE 25

N-(1-{cis-1-(Cyclopropylmethyl)-4-[(cyclopropylmethyl)sulfonyl]cyclohexyl}cyclopropyl)-2-methyl-6-(trifluoromethyl)nicotinamide 1-{cis-1-(Cyclopropylmethyl)-4-[(cyclopropylmethyl)thio]cyclohexyl}cyclopropanamine A solution of cis-1-(cyclopropylmethyl)-4-[(cyclopropylmethyl)thio]cyclohexanecarbonitrile (500 mg, 2 mmol) was formed in dry diethyl ether (10 mL). Titanium(IV) isopropoxide (0.66 mL, 2.2 mmol) was added followed by the dropwise addition of ethyl magnesium bromide (1.3 mL of 3M in diethyl ether, 4 mmol). This mixture was stirred for 1 hour at room temperature then boron trifluoride diethyl etherate (0.5 mL) was added dropwise with vigorous stirring. After a further 2 hours at room temperature the reaction was quenched by the dropwise addition of sodium hydroxide solution (5 mL, 2 M aq). A further 5 mL of the sodium hydroxide solution (2 M, aq) was then added followed by diethyl ether (20 mL). The solution was decanted away from the solid residues and extracted with diethyl ether (2×20 mL). The combined organics were dried over sodium sulphate, filtered and evaporated to give an oil. Purification by flash column chromatography on silica gel using a gradient of 20% ethyl acetate in hexanes—100% ethyl acetate gave 1-{cis-1-(cyclopropylmethyl)-4-[(cyclopropylmethyl)thio]cyclohexyl}cyclopropanamine as a pale yellow oil (90 mg): 1H NMR δ (ppm) (CDCl3): 3.12-3.08 (1H, m), 2.42 (2H, d, J=7.0 Hz), 1.82-1.74 (4H, m), 1.70-1.61 (2H, m), 1.53-1.35 (4H, m), 1.00-0.72 (4H, m), 0.57-0.53 (2H, m), 0.48-0.42 (4H, m), 0.20 (2H, q, J=5.1 Hz), 0.05 (2H, q, J=4.9 Hz).

N-(1-{cis-1-(Cyclopropylmethyl)-4-[(cyclopropylmethyl)sulfonyl]cyclohexyl}cyclopropyl)-2-methyl-6-(trifluoromethyl)nicotinamide 1-{cis-1-(Cyclopropylmethyl)-4-[(cyclopropylmethyl)thio]cyclohexyl}cyclopropanamine (45 mg, 0.16 mmol) was reacted with 2-methyl-6-(trifluoromethyl)nicotinoyl chloride (54 mg, 0.24 mmol) using the method in example 3 then oxidized with oxone using the method in example 1 to give N-(1-{cis-1-(cyclopropylmethyl)-4-[(cyclopropylmethyl)sulfonyl]cyclohexyl}cyclopropyl)-2-methyl-6-(trifluoromethyl)nicotinamide as a white solid (30 mg): 1H NMR (500 MHz, CDCl3): δ 7.73 (1H, d, J 7.8), 7.53 (1H, d, J 7.8), 6.10 (1H, s), 3.07-3.01 (1H, m), 2.91 (2H, d, J 7.1), 2.69 (3H, s), 2.21-2.14 (2H, m), 1.97-1.91 (2H, m), 1.89-1.83 (2H, m), 1.50-1.41 (4H, m), 1.21-1.13 (3H, m), 0.99 (2H, t, J 6.4), 0.89-0.83 (2H, m), 0.75 (2H, q, J 6.4), 0.52 (2H, q, J 5.9), 0.41 (2H, q, J 5.3), 0.09 (2H, q, J 4.9); m/z=499 (M+H+).

EXAMPLE 26

N-(1-{cis-1-(Cyclopropylmethyl)-4-[(cyclopropylmethyl)sulfonyl]cyclohexyl}cyclopropyl)-2-methoxy-4-methyl-6-(trifluoromethyl)nicotinamide 2-Methoxy-4-methyl-6-(trifluoromethyl)nicotinic acid was coupled to 1-{cis-1-(cyclopropylmethyl)-4-[(cyclopropylmethyl)thio]cyclohexyl}cyclopropanamine using the method in example 11 then oxidized with oxone using the method in example 1 to give N-(1-{cis-1-(cyclopropylmethyl)-4-[(cyclopropylmethyl)sulfonyl]cyclohexyl}cyclopropyl)-2-methoxy-4-methyl-6-(trifluoromethyl)nicotinamide as a white solid: 1H NMR (500 MHz, CDCl3): δ 7.13 (1H, s), 6.22 (1H, s), 3.98 (3H, s), 3.04-2.98 (1H, m), 2.91 (2H, d, J 7.1), 2.38 (3H, s), 2.20-2.14 (2H, m), 1.98-1.88 (4H, m), 1.48-1.41 (4H, m), 1.20-1.13 (3H, m), 0.97 (2H, t, J 6.4), 0.74 (2H, q, J 6.4), 0.51-0.49 (2H, m), 0.41 (2H, q, J 5.3), 0.08 (2H, q, J 4.9); m/z=529 (M+H+).

EXAMPLE 27

N-(1-{cis-1-(Cyclopropylmethyl)-4-[(cyclopropylmethyl)sulfonyl]cyclohexyl}-2-hydroxyethyl)-2-methyl-6-(trifluoromethyl)nicotinamide cis-1-(Cyclopropylmethyl)-4-[(cyclopropylmethyl)thio]cyclohexanecarbaldehyde A solution of cis-1-(cyclopropylmethyl)-4-[(cyclopropylmethyl)thio]cyclohexanecarbonitrile (2.0 g, 8 mmol) was formed in dry toluene (40 mL) and cooled to −78° C. A solution of diisobutylaluminum hydride (9.6 mL of 1 M in toluene, 9.6 mmol) was added dropwise and the mixture stirred at −78° C. for 2 hours. The reaction was quenched by the addition of an aqueous solution of Rochelle salt (5 mL, sat.) added dropwise then allowed to warm to room temperature. The mixture was partitioned between ethyl acetate (100 mL) and brine (50 mL). The aqueous was extracted with ethyl acetate (100 mL) and the combined organics were dried over magnesium sulphate, filtered and evaporated to give an oil. Purification by flash column chromatography on silica gel using 2% ethyl acetate in hexanes as eluent gave cis-1-(cyclopropylmethyl)-4-[(cyclopropylmethyl)thio]cyclohexanecarbaldehyde as a pale yellow oil (1.9 g).

N-(1-{cis-1-(Cyclopropylmethyl)-4-[(cyclopropylmethyl)thio]cyclohexyl}methylene)-2-methylpropane-2-sulfinamide A solution of cis-1-(cyclopropylmethyl)-4-[(cyclopropylmethyl)thio]cyclohexanecarbaldehyde (1.9 g, 7.5 mmol) was formed in THF (15 mL). 2-Methyl-2-propanesulfinamide (1.18 g, 9.8 mmol) was added followed by titanium(IV) ethoxide (4.7 mL). This mixture was heated at 60° C. for 6 hours. The mixture was cooled to room temperature and diluted with ethyl acetate (50 mL) and brine (30 mL). The resulting white suspension was stirred at room temperature for 10 mins then filtered through a pad of Hyflo, washing with ethyl acetate. The aqueous was extracted with ethyl acetate (2×50 mL) and the combined organics were dried over magnesium sulphate, filtered and evaporated to give an oil. Purification by flash column chromatography on silica gel using 15% ethyl acetate in hexanes as eluent gave N-(1-{cis-1-(cyclopropylmethyl)-4-[(cyclopropylmethyl)thio]cyclohexyl}methylene)-2-methylpropane-2-sulfinamide as a pale yellow oil (2.0 g): 1H NMR (400 MHz, CDCl3): δ 7.89 (1H, s), 2.69-2.57 (1H, m), 2.46 (2H, d, J 7.0), 2.34-2.28 (1H, m), 2.19-2.12 (1H, m), 1.94-1.88 (2H, m), 1.51-1.29 (6H, m), 1.24 (9H, s), 0.99-0.89 (1H, m), 0.64-0.53 (3H, m), 0.48-0.40 (2H, m), 0.22-0.17 (2H, m), 0.03-(−0.08) (2H, m).

N-(1-{cis-1-(Cyclopropylmethyl)-4-[(cyclopropylmethyl)thio]cyclohexyl}prop-2-en-1-yl)-2-methylpropane-2-sulfinamide A solution of N-(1-{cis-1-(cyclopropylmethyl)-4-[(cyclopropylmethyl)thio]cyclohexyl}methylene)-2-methylpropane-2-sulfinamide (800 mg, 2.2 mmol) was formed in THF (20 mL). A solution of vinyl magnesium bromide (6.7 mL of 1 M in THF, 6.7 mmol) was added dropwise and the mixture stirred at room temperature for 2 hours. The reaction was quenched by dropwise addition of aqueous ammonium chloride (10 mL) then the mixture partitioned between ethyl acetate (100 mL) and water (20 mL). The aqueous was extracted with ethyl acetate (50 mL) and the combined organics were dried over magnesium sulphate, filtered and evaporated to give an oil. Purification by flash column chromatography on silica gel using 50% ethyl acetate:50% hexanes as eluent gave N-(1-{cis-1-(cyclopropylmethyl)-4-[(cyclopropylmethyl)thio]cyclohexyl}prop-2-en-1-yl)-2-methylpropane-2-sulfinamide as a pale yellow oil (600 mg): 1H NMR (500 MHz, CDCl3): δ 5.95-5.88 (1H, m), 5.34 (1H, d, J 17.0), 5.25 (1H, d, J 10.3), 4.02 (1H, t, J 9.0), 3.45 (1H, d, J 10.2), 2.81-2.75 (1H, m), 2.48 (2H, d, J 6.4), 2.06-1.98 (1H, m), 1.89-1.79 (2H, m), 1.71-1.64 (1H, m), 1.56-1.48 (2H, m), 1.39-1.33 (2H, m), 1.28-1.19 (10H, m), 1.18-1.10 (1H, m), 1.01-0.93 (1H, m), 0.72-0.64 (1H, m), 0.58-0.48 (4H, m), 0.21 (2H, q, J 5.0), 0.10-0.04 (2H, m).

(1-{cis-1-(Cyclopropylmethyl)-4-[(cyclopropylmethyl)thio]cyclohexyl}prop-2-en-1-amine N-(1-{cis-1-(Cyclopropylmethyl)-4-[(cyclopropylmethyl)thio]cyclohexyl}prop-2-en-1-yl)-2-methylpropane-2-sulfinamide (600 mg, 1.9 mmol) was dissolved in methanol (5 mL). Hydrogen chloride (2 mL of 4 N in dioxane) was added and the mixture stirred at room temperature for 1 hour. The mixture was neutralize with aqueous sodium hydrogen carbonate and extracted with ethyl acetate. The combined organics were dried over magnesium sulphate, filtered and evaporated to give an oil. The material was loaded onto an SCX cartridge and washed with methanol then eluted with 1 N ammonia in methanol to give (1-{cis-1-(cyclopropylmethyl)-4-[(cyclopropylmethyl)thio]cyclohexyl}prop-2-en-1-amine as a yellow oil (430 mg): 1H NMR (500 MHz, CDCl3): δ 5.93-5.86 (1H, m), 5.14 (1H, d, J 17.0), 5.09 (1H, d, J 10.3), 3.64 (1H, d, J 7.6), 2.82-2.70 (1H, m), 2.48 (2H, d, J 5.8), 1.92-1.82 (3H, m), 1.70-1.40 (5H, m), 1.29-1.13 (2H, m), 1.01-0.93 (1H, m), 0.70-0.62 (1H, m), 0.56 (2H, q, J 6.1), 0.44 (2H, d, J 8.2), 0.21 (2H, q, J 5.0), 0.04-0.00 (2H, m).

N-(1-{cis-1-(Cyclopropylmethyl)-4-[(cyclopropylmethyl)thio]cyclohexyl}prop-2-en-1-yl)-2-methyl-6-(trifluoromethyl)nicotinamide (1-{cis-1-(Cyclopropylmethyl)-4-[(cyclopropylmethyl)thio]cyclohexyl}prop-2-en-1-amine (300 mg, 1.1 mmol) was reacted with 2-methyl-6-(trifluoromethyl)nicotinoyl chloride (360 mg, 1.6 mmol) using the method in example 3 to give N-(1-{cis-1-(cyclopropylmethyl)-4-[(cyclopropylmethyl)thio]cyclohexyl}prop-2-en-1-yl)-2-methyl-6-(trifluoromethyl)nicotinamide as a white solid (300 mg): 1H NMR (500 MHz, CDCl3): δ 7.84 (1H, d, J 7.8), 7.55 (1H, d, J 7.8), 6.24 (1H, d, J 9.6), 5.94-5.87 (1H, m), 5.32 (1H, d, J 17.0), 5.27 (1H, d, J 10.4), 5.08 (1H, t, J 8.2), 2.90-2.83 (1H, m), 2.73 (3H, s), 2.49 (2H, d, J 6.9), 1.90-1.78 (4H, m), 1.71-1.67 (1H, m), 1.49-1.39 (3H, m), 1.18 (2H, dd, J 7.6, 14.5), 1.01-0.93 (1H, m), 0.75-0.68 (1H, m), 0.58-0.52 (3H, m), 0.45-0.38 (1H, m), 0.21 (2H, q, J 4.9), 0.12-0.05 (2H, m).

N-(1-{cis-1-(Cyclopropylmethyl)-4-[(cyclopropylmethyl)sulfonyl]cyclohexyl}-2-hydroxyethyl)-2-methyl-6-(trifluoromethyl)nicotinamide N-(1-{cis-1-(Cyclopropylmethyl)-4-[(cyclopropylmethyl)thio]cyclohexyl}prop-2-en-1-yl)-2-methyl-6-(trifluoromethyl)nicotinamide (150 mg, 0.32 mmol) was dissolved in methanol (10 mL) with DCM (2 mL) in a 3-neck flask. Nitrogen was bubbled through the solution as it was cooled to −78° C. then the gas was swapped for ozone which was bubbled through the solution at −78° C. until saturated (5-10 mins). The ozone generator was switched off allowing oxygen to bubble through the solution to remover the excess ozone. The gas was then swapped for nitrogen and sodium borohydride (30 mg, 0.8 mmol) was added and the mixture allowed to warm to room temperature then stirred for a further 1 hour. The reaction was quenched with the addition of aqueous ammonium chloride then poured into water (30 mL) and extracted with ethyl acetate (2×50 mL). The combined organics were dried over sodium sulphate, filtered and evaporated to give N-(1-{cis-1-(cyclopropylmethyl)-4-[(cyclopropylmethyl)sulfinyl]cyclohexyl}-2-hydroxyethyl)-2-methyl-6-(trifluoromethyl)nicotinamide as a white foam. This was re-dissolved in acetone (5 mL), then water (2.5 mL) and Oxone (295 mg, 0.48 mmol) were added and the mixture heated at reflux for 1 hour. The mixture was cooled to room temperature and neutralized with aqueous sodium hydrogen carbonate, poured into water (30 mL) and extracted with ethyl acetate (2×30 mL). The combined organics were dried over magnesium sulphate, filtered and evaporated to give an oil. Purification by flash column chromatography on silica gel using 70% ethyl acetate:30% hexanes as eluent gave N-(1-{cis-1-(cyclopropylmethyl)-4-[(cyclopropylmethyl)sulfonyl]cyclohexyl}-2-hydroxyethyl)-2-methyl-6-(trifluoromethyl)nicotinamide as a white foam (70 mg): 1H NMR (500 MHz, CDCl3): δ 7.87 (1H, d, J 7.8), 7.52 (1H, d, J 7.8), 6.36 (1H, d, J 9.6), 4.67-4.63 (1H, m), 4.00-3.94 (1H, m), 3.71-3.65 (1H, m), 3.05-2.98 (1H, m), 2.94-2.86 (2H, m), 2.72 (3H, s), 2.23-2.17 (1H, m), 2.11-2.03 (1H, m), 2.02-1.93 (4H, m), 1.63-1.57 (1H, m), 1.48-1.42 (1H, m), 1.39-1.25 (2H, m), 1.18-1.14 (1H, m), 0.75 (2H, d, J 8.0), 0.70-0.63 (1H, m), 0.57-0.51 (1H, m), 0.50-0.38 (3H, m), 0.12-0.06 (2H, m); m/z=503 (M+H$^+$).

EXAMPLE 28

N-[{cis-1-(Cyclopropylmethyl)-4-[(cyclopropylmethyl)sulfonyl]cyclohexyl}(oxiran-2-yl)methyl]-2-methyl-6-(trifluoromethyl)nicotinamide A solution of N-(1-{cis-1-(Cyclopropylmethyl)-4-[(cyclopropylmethyl)thio]cyclohexyl}prop-2-en-1-yl)-2-methyl-6-(trifluoromethyl)nicotinamide (100 mg, 0.21 mmol) was dissolved in DCM (5 mL). m-Chloroperoxybenzoic acid (216 mg of 77%, 0.96 mmol) was added and the mixture stirred for 24 hours at room temperature. The mixture was then poured into aqueous sodium carbonate (20 mL) and extracted with ethyl acetate (2×20 mL). Combined organics were dried over magnesium sulphate, filtered and evaporated to give an oil. Purification by flash column chromatography on silica gel using 20% ethyl acetate:80% DCM as eluent gave N-[{cis-1-(cyclopropylmethyl)-4-[(cyclopropylmethyl)sulfonyl]cyclohexyl}(oxiran-2-yl)methyl]-2-methyl-6-(trifluoromethyl)nicotinamide as a white solid (56 mg): 1H NMR (500 MHz, CDCl3): δ 7.84 (1H, d, J 7.8), 7.56 (1H, d, J 7.8), 6.02 (1H, d, J 9.9), 4.88 (1H, d, J 9.9), 3.26 (1H, s), 3.06-3.02 (1H, m), 2.97-2.89 (2H, m), 2.80 (1H, t, J 4.2), 2.73 (3H, s), 2.55-2.52 (1H, m), 2.30-2.22 (1H, m), 2.17-2.10 (2H, m), 2.04-1.96 (3H, m), 1.77-1.71 (1H, m), 1.56-1.46 (2H, m), 1.37 (1H, dd, J 7.3, 14.6), 1.23-1.15 (1H, m), 0.79-0.72 (3H, m), 0.61-0.55 (1H, m), 0.50-0.39 (3H, m), 0.21-0.15 (1H, m), 0.14-0.07 (1H, m); m/z=515 (M+H⁺).

EXAMPLE 29

N-(1-{cis-1-(Cyclopropylmethyl)-4-[(cyclopropylmethyl)sulfonyl]cyclohexyl}-2-hydroxypropyl)-2-methyl-6-(trifluoromethyl)nicotinamide A solution of N—[{cis-1-(cyclopropylmethyl)-4-[(cyclopropylmethyl)sulfonyl]cyclohexyl}(oxiran-2-yl)methyl]-2-methyl-6-(trifluoromethyl)nicotinamide (45 mg, 0.09 mmol) was formed in diethyl ether (5 mL). Methanol (5 µL, 0.13 mmol) and lithium borohydride (3 mg, 0.13 mmol) were added and the mixture stirred for 2 hours at room temperature. The mixture was poured into water (10 mL), acidified with hydrochloric acid (1 M, aq) then extracted with ethyl acetate (2×20 mL). The combined organics were dried over magnesium sulphate, filtered and evaporated to give an oil. Purification by flash column chromatography on silica gel using 40% ethyl acetate:60% DCM as eluent gave N-(1-{cis-1-(cyclopropylmethyl)-4-[(cyclopropylmethyl)sulfonyl]cyclohexyl}-2-hydroxypropyl)-2-methyl-6-(trifluoromethyl)nicotinamide as a white solid (21 mg): 1H NMR (500 MHz, CDCl3): δ 7.96 (1H, d, J 7.8), 7.57 (1H, d, J 7.8), 6.45 (1H, d, J 9.7), 4.40-4.32 (2H, m), 3.07-3.01 (1H, m), 2.96-2.88 (2H, m), 2.76 (3H, s), 2.34-2.26 (1H, m), 2.06 (2H, d, J 11.2), 2.01-1.86 (3H, m), 1.74-1.68 (1H, m), 1.51-1.43 (3H, m), 1.30 (3H, d, J 6.2), 1.19-1.13 (1H, m), 0.78-0.73 (2H, m), 0.71-0.64 (1H, m), 0.56-0.52 (1H, m), 0.48-0.38 (3H, m), 0.11-0.03 (2H, m); m/z=517 (M+H⁺).

EXAMPLE 30

N-(1-{cis-1-(Cyclopropylmethyl)-4-[(cyclopropylmethyl)sulfonyl]cyclohexyl}-2,2,2-trifluoroethyl)-2-methyl-6-(trifluoromethyl)nicotinamide N-(1-{cis-1-(Cyclopropylmethyl)-4-[(cyclopropylmethyl)thio]cyclohexyl}-2,2,2-trifluoroethyl)-2-methylpropane-2-sulfinamide A solution of N-(1-{cis-1-(cyclopropylmethyl)-4-[(cyclopropylmethyl)thio]cyclohexyl}methylene)-2-methylpropane-2-sulfinamide (1.0 g, 2.8 mmol) was formed in THF (70 mL). Tetramethylammonium fluoride (288 mg, 3.1 mmol) was added and the resulting suspension was cooled to −20° C. A solution of trifluoromethyl trimethylsilane (0.54 mL, 3.7 mmol) in THF (10 mL) was added dropwise. The mixture was stirred at −20° C. for 30 mins then allowed to warm to room temperature. The reaction was quenched with aqueous ammonium chloride (50 mL) and extracted with ethyl acetate (100 mL×2). The combined organics were dried over magnesium sulphate, filtered and evaporated to give an oil. Purification by flash column chromatography on silica gel using 20% ethyl acetate:80% hexanes as eluent gave N-(1-{cis-1-(cyclopropylmethyl)-4-[(cyclopropylmethyl)thio]cyclohexyl}-2,2,2-trifluoroethyl)-2-methylpropane-2-sulfinamide as a colourless oil (1.1 g): 1H NMR (500 MHz, CDCl3): δ 4.15-4.09 (1H, m), 4.07-4.00 (1H, m), 2.88-2.80 (1H, m), 2.48 (2H, d, J 6.6), 2.31-2.25 (1H, m), 2.00-1.86 (3H, m), 1.43-1.37 (6H, m), 1.25 (9H, s), 1.00-0.92 (1H, m), 0.79-0.73 (1H, m), 0.59-0.51 (4H, m), 0.22-0.12 (4H, m).

(1-{cis-1-(Cyclopropylmethyl)-4-[(cyclopropylmethyl)thio]cyclohexyl}-2,2,2-trifluoroethanamine N-(1-{cis-1-(Cyclopropylmethyl)-4-[(cyclopropylmethyl)thio]cyclohexyl}-2,2,2-trifluoroethyl)-2-methylpropane-2-sulfinamide was hydrolysed using the method in example LL to give (1-{cis-1-(cyclopropylmethyl)-4-[(cyclopropylmethyl)thio]cyclohexyl}-2,2,2-trifluoroethanamine as a colourless oil: 1H NMR (500 MHz, CDCl3): δ 3.50 (1H, q, J 8.9), 2.83-2.79 (1H, m), 2.48 (2H, d, J 7.0), 2.14-2.08 (1H, m), 1.97-1.88 (3H, m), 1.65-1.33 (6H, m), 1.01-0.91 (1H, m), 0.70-0.63 (1H, m), 0.57 (2H, q, J 6.1), 0.51-0.44 (2H, m), 0.21 (2H, q, J 5.0), 0.10-0.04 (2H, m).

N-(1-{cis-1-(Cyclopropylmethyl)-4-[(cyclopropylmethyl)thio]cyclohexyl}-2,2,2-trifluoroethyl)-2-methyl-6-(trifluoromethyl)nicotinamide (1-{cis-1-(Cyclopropylmethyl)-4-[(cyclopropylmethyl)thio]cyclohexyl}-2,2,2-trifluoroethanamine (170 mg, 0.53 mmol) was reacted with 2-methyl-6-(trifluoromethyl)nicotinoyl chloride (360 mg, 1.6 mmol) using the method in example 3 to give N-(1-{cis-1-(cyclopropylmethyl)-4-[(cyclopropylmethyl)thio]cyclohexyl}-2,2,2-trifluoroethyl)-2-methyl-6-(trifluoromethyl)nicotinamide as a colourless oil (220 mg): 1H NMR (500 MHz, CDCl3): δ 7.87 (1H, d, J 7.8), 7.57 (1H, d, J 7.8), 6.54 (1H, d, J 10.3), 5.25-5.18 (1H, m), 2.92 (1H, br s), 2.74 (3H, s), 2.49 (2H, d, J 6.9), 2.02-1.88 (4H, m), 1.79-1.67 (2H, m), 1.64-1.56 (2H, m), 1.51-1.37 (2H, m), 1.01-0.93 (1H, m), 0.75-0.69 (1H, m), 0.62-0.56 (3H, m), 0.46-0.40 (1H, m), 0.24-0.20 (2H, m), 0.18-0.14 (2H, m).

N-(1-{cis-1-(Cyclopropylmethyl)-4-[(cyclopropylmethyl)sulfonyl]cyclohexyl}-2,2,2-trifluoroethyl)-2-methyl-6-(trifluoromethyl)nicotinamide N-(1-{cis-1-(cyclopropylmethyl)-4-[(cyclopropylmethyl)thio]cyclohexyl}-2,2,2-trifluoroethyl)-2-methyl-6-(trifluoromethyl)nicotinamide (220 mg, 0.43 mmol) was reacted with Oxone (793 mmol, 1.29 mmol) using the method in example 2 to give N-(1-{cis-1-(cyclopropylmethyl)-4-[(cyclopropylmethyl)sulfonyl]cyclohexyl}-2,2,2-trifluoroethyl)-2-methyl-6-(trifluoromethyl)nicotinamide as a white solid (220 mg): 1H NMR (500 MHz, CDCl3): δ 7.88 (1H, d, J 7.8), 7.58 (1H, d, J 7.8), 6.54 (1H, d, J 10.3), 5.30-5.22 (1H, m), 3.06-3.02 (1H, m), 2.97-2.89 (2H, m), 2.72 (3H, s), 2.20-1.98 (6H, m), 1.71-1.63 (1H, m), 1.58-1.42 (3H, m), 1.22-1.14 (1H, m), 0.80-0.72 (3H, m), 0.65-0.59 (1H, m), 0.48-0.40 (3H, m), 0.21-0.13 (2H, m); m/z=541 (M+H⁺).

EXAMPLE 31

N-({cis-1-(Cyclopropylmethyl)-4-[(cyclopropylmethyl)sulfonyl]cyclohexyl}methyl)-4-isopropyl-2-methoxy-6-(trifluoromethyl)nicotinamide Ethyl 4-isopropyl-2-oxo-6-(trifluoromethyl)-1,2-dihydropyridine-3-carboxylate A solution of 1,1,1-trifluoro-4-methoxy-5-methylhex-3-en-2-one (5 g, 25.5 mmol) and ethyl malonate monoamide (3.3 g, 25.5 mmol) was formed in ethanol (30 mL). A solution on sodium ethoxide (9 g of 21% in ethanol, 28 mmol) was added and the mixture heated at 85° C. for 18 hours then cooled to room temperature. Hydrochloric acid (10 mL of 5 N aq) was added followed by water (10 mL). This was then extracted with chloroform (2×100 mL). The combined organics were washed with brine (50 mL), dried over magnesium sulphate, filtered and evaporated to give a black oil. Purification by flash column chromatography on silica gel using 10% ethyl acetate:90% DCM as eluent gave both ethyl 4-isopropyl-2-oxo-6-(trifluoromethyl)-1,2-dihydropyridine-3-carboxylate as a white solid (3 g)—less polar: 1H NMR (500 MHz, CDCl3): δ 6.98 (1H, s), 4.46 (2H, q, J 7.1), 3.32-3.26 (1H, m), 1.41 (3H, t, J 7.1), 1.24 (6H, d, 6.8).

and ethyl 6-isopropyl-2-oxo-4-(trifluoromethyl)-1,2-dihydropyridine-3-carboxylate as a white solid (650 mg)—more polar: 1H NMR (500 MHz, CDCl3): δ 6.24 (1H, s), 4.40 (2H, q, J 7.1), 2.96-2.88 (1H, m), 1.36 (3H, t, J 7.1), 1.31 (6H, d, J 7.0).

N-({cis-1-(Cyclopropylmethyl)-4-[(cyclopropylmethyl)sulfonyl]cyclohexyl}methyl)-4-isopropyl-2-methoxy-6-(trifluoromethyl)nicotinamide Ethyl 4-isopropyl-2-oxo-6-(trifluoromethyl)-1,2-dihydropyridine-3-carboxylate was subjected to the reactions in example 11 to give N-({cis-1-(cyclopropylmethyl)-4-[(cyclopropylmethyl)sulfonyl]cyclohexyl}methyl)-4-isopropyl-2-methoxy-6-(trifluoromethyl)nicotinamide as a white solid: 1H NMR (500 MHz, CDCl3): δ 7.24 (1H, s), 5.79 (1H, br s), 3.98 (3H, s), 3.62 (2H, d, J 6.3), 3.23-3.17 (1H, m), 2.95-2.89 (3H, m), 2.09-2.01 (2H, m), 1.98-1.88 (4H, m), 1.42-1.35 (2H, m), 1.28-1.16 (9H, m), 0.76 (2H, d, J 7.6), 0.73-0.67 (1H, m), 0.51 (2H, d, J 7.5), 0.42 (2H, d, J 5.0), 0.04 (2H, d, J 4.6); m/z=531 (M+H+).

EXAMPLE 32

N-({cis-1-(Cyclopropylmethyl)-4-[(cyclopropylmethyl)sulfonyl]cyclohexyl}methyl)-6-isopropyl-2-methoxy-4-(trifluoromethyl)nicotinamide Ethyl 6-isopropyl-2-oxo-4-(trifluoromethyl)-1,2-dihydropyridine-3-carboxylate (from example PP) was subjected to the reactions in example 11 to give N-({cis-1-(cyclopropylmethyl)-4-[(cyclopropylmethyl)sulfonyl]cyclohexyl}methyl)-6-isopropyl-2-methoxy-4-(trifluoromethyl)nicotinamide as a white solid: 1H NMR (500 MHz, CDCl3): δ 6.98 (1H, s), 5.77 (1H, t, J 5.6), 3.98 (3H, s), 3.61 (2H, d, J 6.4), 3.04-2.98 (1H, m), 2.93-2.85 (3H, m), 2.10-2.03 (2H, m), 1.96-1.88 (4H, m), 1.42-1.34 (2H, m), 1.29 (6H, d, J 6.8), 1.23-1.15 (3H, m), 0.75 (2H, q, J 6.4), 0.70-0.64 (1H, m), 0.49 (2H, q, J 5.9), 0.43 (2H, q, J 5.3), 0.03 (2H, q, J 4.9); m/z=531 (M+H+).

EXAMPLE 33

2-Amino-N-({cis-1-(cyclopropylmethyl)-4-[(cyclopropylmethyl)sulfonyl]cyclohexyl}methyl)-4,6-bis(trifluoromethyl)nicotinamide Ethyl 2-amino-4,6-bis(trifluoromethyl)nicotinate was hydrolysed and coupled to ({cis-1-(cyclopropylmethyl)-4-[(cyclopropylmethyl)sulfonyl]cyclohexyl}methyl)amine using the method in example 11 to give 2-amino-N-({cis-1-(cyclopropylmethyl)-4-[(cyclopropylmethyl)sulfonyl]cyclohexyl}methyl)-4,6-bis(trifluoromethyl)nicotinamide as a white solid: 1H NMR (400 MHz, CDCl3): δ 7.20 (1H, s), 6.00 (1H, br s), 5.53 (2H, s), 3.63 (2H, d, J 6.3), 2.97-2.89 (3H, m), 2.09-2.00 (2H, m), 1.97-1.83 (4H, m), 1.42-1.34 (2H, m), 1.28-1.14 (3H, m), 0.76 (2H, q, J 6.4), 0.71-0.60 (1H, m), 0.52-0.48 (2H, m), 0.41 (2H, q, J 5.3), 0.03 (2H, q, J 5.0); m/z=542 (M+H+).

EXAMPLE 34

N-({cis-1-(Cyclopropylmethyl)-4-[(cyclopropylmethyl)sulfonyl]cyclohexyl}methyl)-1,4-dimethyl-2-oxo-6-(trifluoromethyl)-1,2-dihydropyridine-3-carboxamide Ethyl 1,4-dimethyl-2-oxo-6-(trifluoromethyl)-1,2-dihydropyridine-3-carboxylate was hydrolysed and coupled to ({cis-1-(cyclopropylmethyl)-4-[(cyclopropylmethyl)sulfonyl]cyclohexyl}methyl)amine using the method in example 11 to give N-({cis-1-(cyclopropylmethyl)-4-[(cyclopropylmethyl)sulfonyl]cyclohexyl}methyl)-1,4-dimethyl-2-oxo-6-(trifluoromethyl)-1,2-dihydropyridine-3-carboxamide as a white solid: 1H NMR (500 MHz, CDCl3): δ 9.01 (1H, s), 6.64 (1H, s), 3.63 (3H, s), 3.57 (2H, d, J 5.8), 2.95-2.87 (3H, m), 2.65 (3H, s), 2.07-2.00 (2H, m), 1.91 (4H, q, J 11.9), 1.39-1.33 (2H, m), 1.27 (2H, d, J 6.7), 1.20-1.14 (1H, m), 0.76-0.67 (3H, m), 0.48 (2H, q, J 5.8), 0.41 (2H, q, J 5.2), 0.07 (2H, d, J 4.7); m/z=503 (M+H+).

EXAMPLE 35

N-(1-{cis-1-(Cyclopropylmethyl)-4-[(cyclopropylmethyl)sulfonyl]cyclohexyl}-2-hydroxyethyl)-2-methoxy-4-methyl-6-(trifluoromethyl)nicotinamide N-(1-{cis-1-(Cyclopropylmethyl)-4-[(cyclopropylmethyl)thio]cyclohexyl}prop-2-en-1-yl)-2-methoxy-4-methyl-6-(trifluoromethyl)nicotinamide (1-{cis-1-(Cyclopropylmethyl)-4-[(cyclopropylmethyl)thio]cyclohexyl}prop-2-en-1-amine (270 mg, 0.97 mmol) was reacted with 2-methoxy-4-methyl-6-(trifluoromethyl)nicotinic acid (341 mg, 1.4 mmol) using the method in example 11 to give N-(1-{cis-1-(cyclopropylmethyl)-4-[(cyclopropylmethyl)thio]cyclohexyl}prop-2-en-1-yl)-2-methoxy-4-methyl-6-(trifluoromethyl)nicotinamide as a white solid (360 mg): 1H NMR (500 MHz, CDCl3): δ 7.16 (1H, s), 6.35 (1H, d, J 9.6), 5.96-5.89 (1H, m), 5.38 (1H, d, J 17.0), 5.25 (1H, d, J 10.5), 5.13 (1H, t, J 7.6), 3.99 (3H, s), 2.83-2.76 (1H, m), 2.49 (2H, d, J 6.9), 2.44 (3H, s), 1.96-1.78 (5H, m), 1.71-1.64 (1H, m), 1.48-1.38 (2H, m), 1.32 (1H, dd, J 5.5, 14.3), 1.14 (1H, dd, J 7.6, 14.4), 1.01-0.93 (1H, m), 0.74-0.66 (1H, m), 0.56 (2H, q, J 6.0), 0.53-0.47 (1H, m), 0.44-0.38 (1H, m), 0.21 (2H, q, J 4.9), 0.09-0.03 (2H, m).

N-(1-{cis-1-(Cyclopropylmethyl)-4-[(cyclopropylmethyl)sulfonyl]cyclohexyl}-2-hydroxyethyl)-2-methoxy-4-methyl-6-(trifluoromethyl)nicotinamide N-(1-{cis-1-(Cyclopropylmethyl)-4-[(cyclopropylmethyl)thio]cyclohexyl}prop-2-en-1-yl)-2-methoxy-4-methyl-6-(trifluoromethyl)nicotinamide was subjected to the reactions in example 26 to give N-(1-{cis-1-(cyclopropylmethyl)-4-[(cyclopropylmethyl)sulfonyl]cyclohexyl}-2-hydroxyethyl)-2-methoxy-4-methyl-6-(trifluoromethyl)nicotinamide as a white solid: 1H NMR (500 MHz, CDCl3): δ 7.17 (1H, s), 6.29 (1H, d, J 9.6), 4.73-4.67 (1H, m), 4.00 (3H, s), 3.94 (1H, d, J 8.8), 3.66 (1H, t, J 9.8), 3.00-2.86 (3H, m), 2.45 (3H, s), 2.21-1.90 (6H, m), 1.62-1.56 (1H, m), 1.47-1.40 (1H, m), 1.34-1.14 (3H, m), 0.78-0.72 (2H, m), 0.71-0.63 (1H, m), 0.57-0.53 (1H, m), 0.48-0.39 (3H, m), 0.11-0.03 (2H, m); m/z=533 (M+H+).

EXAMPLE 36

2-cyano-2,6-dimethyl-pyrimidine-5-carboxylic acid (4-cyclopropylmethanesulfonyl-1-cyclopropylmethyl-cyclohexylmethyl)-amide 2-methanesulfonyl-4,6-dimethyl-pyrimidine-5-carboxylic acid (4-cyclopropylmethanesulfonyl-1-cyclopropylmethyl-cyclohexylmethyl)-amide To a stirred solution of 4,6-dimethyl-2-methylsulfanyl-pyrimidine-5-carboxylic acid (4-cyclopropylmethanesulfonyl-1-cyclopropylmethyl-cyclohexylmethyl)-amide (141 mg; 0.303 mmol) in acetone (3 ml) was added a slurry of oxone (558 mg; 0.908 mmol) in water (1.5 ml). The mixture was heated at reflux for 90 minutes then left to cool on standing for 18 hours. Water (8 ml) was added and the pH was adjusted to 7 with 2 M sodium carbonate solution. The mixture was extracted with DCM (2×25 ml). The combined organics were washed with brine (20 ml), dried (MgSO$_4$) and evaporated in vacuo. The resulting oil was triturated with EtOAc/hexane to give a white, sticky solid which was dried in vacuo to give the product as a white solid foam (94 mg). 1H NMR (400 MHz, CDCl3): δ 6.64 (1H, t, J 6.1), 3.64 (2H, d, J 6.3), 3.23 (3H, s), 2.97-2.85 (3H, m), 2.63 (6H, s), 2.05-1.99 (2H, m), 1.92-1.82 (4H, m), 1.48-1.36 (2H, m), 1.28-1.24 (2H, m), 1.17-1.13 (1H, m), 0.78-0.70 (3H, m), 0.54-0.50 (2H, m), 0.45-0.36 (2H, m), 0.09-0.02 (2H, m). m/z=498 (M+H+).

2-cyano-2,6-dimethyl-pyrimidine-5-carboxylic acid (4-cyclopropylmethanesulfonyl-1-cyclopropylmethyl-cyclohexylmethyl)-amide To a stirred solution of 2-methanesulfonyl-4,6-dimethyl-pyrimidine-5-carboxylic acid (4-cyclopropylmethanesulfonyl-1-cyclopropylmethyl-cyclohexylmethyl)-amide (82 mg; 0.165 mmol) in DMF (2 ml) was added sodium cyanide (12 mg; 0.247 mmol) and the mixture was stirred at room temperature for 90 minutes. The mixture was evaporated in vacuo, coevaporating with toluene, to give an orange oil. The oil was partitioned between EtOAc (20 ml) and water (20 ml). The organic phase was separated, washed with water (20 ml) and brine (20 ml), dried (MgSO$_4$) and evaporated in vacuo to give a yellow oil. The crude product was purified by prep. TLC eluted with 50% EtOAc in hexane to give the product as a white foam (43 mg). 1H NMR (400 MHz, CDCl3): δ 5.96 (1H, t, J 6.2), 3.64 (2H, d, J 6.4), 2.99-2.93 (1H, m), 2.87 (2H, d, J 7.1), 2.57 (6H, s), 2.04-1.84 (6H, m), 1.47-1.39 (2H, m), 1.27-1.23 (2H, m), 1.16-1.08 (1H, m), 0.79-0.67 (3H, m), 0.55-0.51 (2H, m), 0.42-0.38 (2H, m), 0.05-0.03 (2H, m). m/z=445 (M+H+).

EXAMPLE 37

2,4-dichloro-N-[1-(cyclopropyl-hydroxyl-methyl)-4-cyclopropylmethanesulfonyl-cyclohexylmethyl]-benzamide 1-(cyclopropyl-hydroxy-methyl)-4-cyclopropylmethylsulfanyl-cyclohexanecarbonitrile To a stirred solution of diisopropylamine (1.59 ml; 11.3 mmol) in THF (10 ml) at 0° C. was added dropwise butyl lithium (2.5 M in hexanes; 4.51 ml; 11.3 mmol). The mixture was stirred at 0° C. for 15 minutes then cooled to −78° C. A solution of 4-cyclopropylmethylsulfanyl-cyclohexanecarbonitrile (2 g; 10.2 mmol) in THF (10 ml) was added dropwise. On complete addition, the mixture was stirred at −78° C. for 30 minutes. Cyclopropanecarboxaldehyde (0.91 ml; 12.2 mmol) was added dropwise and the mixture was allowed to warm slowly to room temperature and stir for 64 hours. The mixture was quenched with brine (50 ml) and extracted with EtOAc (2×75 ml). The combined organics were washed with saturated sodium hydrogen carbonate solution (50 ml) and brine (50 ml), dried (MgSO$_4$) and evaporated in vacuo to give an orange oil. The crude product was chromatographed on silica eluted with 25-30% EtOAc in hexane to give the product as an orange oil (1.9339 g). 1H NMR (400 MHz, DMSO): δ 5.29 (1H, d, J 4.9), 2.76 (1H, dd, J 4.9, 7.8), 2.68-2.58 (1H, m), 2.15-2.11 (1H, m), 2.04-1.98 (4H, m), 1.56-1.38 (4H, m), 0.98-0.88 (2H, m), 0.52-0.48 (3H, m), 0.45-0.37 (1H, m), 0.34-0.28 (2H, m), 0.19-0.17 (2H, m). m/z=266 (M+H+).

1-(cyclopropyl-hydroxy-methyl)-4-cyclopropyl-methanesulfonyl-cyclohexanecarbonitrile To a stirred solution of 1-(cyclopropyl-hydroxy-methyl)-4-cyclopropylmethylsulfanyl-cyclohexanecarbonitrile (1.93 g; 7.27 mmol) in acetone (15 ml) was added a slurry of oxone (13.4 g; 21.8 mmol) in water (10 ml). The mixture was heated at 60° C. for 1 hour then allowed to cool to room temperature. Water (50 ml) was added and the pH was adjusted to 7 with 2 M sodium carbonate solution. The mixture was extracted with EtOAc (80 ml) and DCM 950 ml). The combined organics were dried (MgSO$_4$) and evaporated in vacuo to give the product as a white solid (1.9015 g). 1H NMR (400 MHz, DMSO): δ 5.36 (1H, d, J 5.0), 3.11-3.05 (3H, m), 2.78 (1H, dd, J 4.8, 7.8), 2.26-2.20 (1H, m), 2.14-2.08 (3H, m), 1.67-1.43 (4H, m), 1.08-0.84 (2H, m), 0.62-0.58 (2H, m), 0.53-0.49 (1H, m), 0.46-0.30 (5H, m). m/z=320 (M+Na+).

(1-amino methyl-4-cyclopropylmethanesulfonyl-cyclohexyl)-cyclopropyl-methanol

To 1-(cyclopropyl-hydroxy-methyl)-4-cyclopropyl-methanesulfonyl-cyclohexanecarbonitrile (1.90 g; 6.39 mmol) in 2 M ammonia in methanol solution (20 ml) (nitrile did not dissolve) under a nitrogen atmosphere was added Raney Nickel (approx. 1 ml of 50% aqueous slurry). The resulting mixture was agitated under an atmosphere of hydrogen (50 psi) on a Parr apparatus for 40 hours. MS indicated that very little reduction of the nitrile had taken place. The mixture was filtered through a catalyst filter and the catalyst washed extensively with MeOH (300 ml, added in portions). The filtrate was evaporated in vacuo to give a greeny-white solid, which was transferred to the Parr flask as a suspension in EtOH (20 ml). Aqueous ammonia solution (1.5 ml) was added followed by Raney Nickel (approx. 1 ml of 50% aqueous slurry). The resulting mixture was agitated under an atmosphere of hydrogen (50 psi) on a Parr apparatus for 24 hours. MS indicated the presence of starting material (m/z=320, [M+Na]+), a small amount of product (m/z=302) and product with water eliminated (m/z=284). The mixture was filtered and the catalyst washed as before. The filtrate was evaporated in vacuo to give a greeny-white solid, which was triturated with MeOH and collected by filtration as a white solid (775 mg). NMR indicated that this was recovered starting material. The trituration filtrate was evaporated in vacuo and the residue was loaded in MeOH on to a SCX cartridge. The cartridge was washed with several column lengths of MeOH followed by 2M ammonia in methanol solution to elute the amine. The desired product was obtained as a green oil upon evaporation of the appropriate fractions (229 mg). m/z=302 (M+H$^+$).

2,4-dichloro-N-[1-(cyclopropyl-hydroxyl-methyl)-4-cyclopropylmethanesulfonyl-cyclohexylmethyl]-benzamide To a solution of (1-aminomethyl-4-cyclopropylmethanesulfonyl-cyclohexyl)-cyclopropyl-methanol (229 mg; 0.760 mmol) and N,N-diisopropylethylamine (0.16 ml; 0.912 mmol) in DCM (5 ml) was added 2,4-dichlorobenzoylchloride (0.12 ml; 0.836 mmol). The mixture was stirred at room temperature for 18 hours. MS indicated the absence of starting material to give new peaks at m/z=475 ([M+H]+), 496 ([M+Na]+) and 456 ([M–H$_2$O]) Water (5 ml) and DCM (3 ml) was added and the mixture was stirred vigorously for 5 minutes then passed through a PTFE separation frit. The organic phase was collected and evaporated and evaporated in vacuo to give a brown oil The oil was chromatographed on silica eluted with 30% EtOAc in DCM. The resulting white foam was impure by NMR and was purified by prep. TLC eluted with 2% MeOH in DCM. A white foam (86 mg) was obtained. NMR and HPLC indicated an impurity (approximately 20%), thought to be compound where water has eliminated to give a double bond. The material was purified on the Agilent, with a loss of the majority of the product due to technical difficulties. 1H NMR δ (ppm) (CDCl3): 7.60 (1H, d, J=8.3 Hz), 7.42 (1H, d, J=1.9 Hz), 7.31 (5H, dd, J=1.9, 8.3 Hz), 7.22-7.18 (1H, m), 3.70 (2H, ABq, J=6.3, 14.3, 64.5 Hz), 2.93-2.87 (3H, m), 2.68 (1H, d, J=9.0 Hz), 2.14-2.08 (2H, m), 2.04-1.97 (2H, m), 1.93-1.79 (3H, m), 1.44-1.40 (2H, m), 1.23-1.15 (1H, m), 1.06-0.99 (1H, m), 0.77-0.67 (3H, m), 0.59-0.53 (1H, m), 0.44-0.42 (2H, m), 0.37-0.31 (1H, m), 0.29-0.23 (1H, m). m/z=474 (M+H$^+$).

EXAMPLE 38

N-(4-cyclopropylmethanesulfonyl-1-pyrrolidin-1-ylmethyl-cyclohexylmethyl)-2-methoxy-4-methyl-6-trifluoromethyl-nicotinamide 4-cyclopropylmethanesulfanyl-1-(pyrrolidine-1-carbonyl)-cyclohexanecarbonitrile To a stirred solution of 4-cyclopropylmethylsulfanyl-cyclohexanecarbonitrile (504 mg; 2.58 mmol) in THF (6 ml) at −78° C. was added KHMDS (0.5 M solution in toluene; 5.16 ml; 2.58 mmol) and the solution was stirred at −78° C. for 1 hour. Pyrrolidine carbonyl chloride (0.29 ml; 2.58 mmol) was added and the solution was stirred at −78° C. for 1 hour then allowed to warm to room temperature and stir for 18 hours. The reaction was quenched with water (20 ml) and extracted with EtOAc (30 ml). The organic phase was dried over MgSO$_4$, filtered and evaporated to give a pale yellow oil. The crude product was chromatographed on silica eluted with 30-46% EtOAc in hexane to give the product as a white solid (581 mg). 1H NMR (400 MHz, CDCl3): δ 3.78 (2H, t, J 6.6), 3.52 (2H, t, J 7.0), 2.71-2.63 (1H, m), 2.51 (2H, d, J 7.0), 2.19-2.11 (4H, m), 2.04-1.71 (8H, m), 1.01-0.91 (1H, m), 0.59-0.55 (2H, m), 0.23-0.19 (2H, m). m/z=331 (M+K$^+$).

4-cyclopropylmethanesulfonyl-1-(pyrrolidine-1-carbonyl)-cyclohexanecarbonitrile

To a stirred solution of 4-cyclopropylmethanesulfanyl-1-(pyrrolidine-1-carbonyl)-cyclohexanecarbonitrile (262 mg; 0.896 mmol) in acetone (6 ml) was added a slurry of oxone (1.65 g; 2.69 mmol) in water (3 ml). The mixture was heated at reflux for 2 hours then allowed to cool to room temperature. The mixture was diluted with water (10 ml) and the pH was adjusted to 7 with 2 M sodium carbonate solution. The mixture was extracted with EtOAc (20 ml). The organic phase was dried (MgSO$_4$) and evaporated in vacuo to give the product as a white solid (246 mg). 1H NMR (500 MHz, CDCl3): δ 3.79 (2H, t, J 6.6), 3.54 (2H, t, J 7.0), 3.01-2.95 (1H, m), 2.92 (2H, d, J 7.1), 2.33-2.27 (4H, m), 2.10-1.96 (6H, m), 1.92-1.86 (2H, m), 1.22-1.14 (1H, m), 0.79-0.75 (2H, m), 0.43-0.41 (2H, m). m/z=325 (M+H$^+$).

C-(4-cyclopropylmethanesulfonyl-1-pyrrolidin-1-ylmethyl-cyclohexyl)-methylamine 4-cyclopropylmethanesulfonyl-1-(pyrrolidine-1-carbonyl)-cyclohexanecarbonitrile (246 mg; 0.0758 mmol) and borane-THF complex (1.0 M solution in THF; 10 ml; 10 mmol) were stirred at room temperature overnight. LC-MS indicated that the reaction had not gone to completion. The mixture was heated at reflux for 2 hours then allowed to cool to room temperature. The mixture was cooled in an icebath and quenched with MeOH (3 ml) then evaporated to dryness in vacuo. The residue was dissolved in MeOH (7 ml) and acidified with concentrated HCl. The mixture was stirred at room temperature for 18 hours. The mixture was poured on to a SCX cartridge. The cartridge was washed with several column lengths of MeOH followed by 2M ammonia in methanol solution to elute the amine. The desired product was obtained as a colourless oil upon evaporation of the appropriate fractions (44 mg). m/z=315 (M+H$^+$).

N-(4-cyclopropylmethanesulfonyl-1-pyrrolidin-1-ylmethyl-cyclohexylmethyl)-2-methoxy-4-methyl-6-trifluoromethyl-nicotinamide To a stirred solution of C-(4-cyclopropylmethanesulfonyl-1-pyrrolidin-1-ylmethyl-cyclohexyl)-methylamine (44 mg; 0.140 mmol) in DCM (1.5 ml) were added WSCDI (62 mg; 0.210 mmol), HOBT (2.8 mg; 0.0210 mmol) and acid (49 mg; 0.210 mmol). The resulting mixture was stirred at room temperature for 18 hours. Water (5 ml) and DCM (5 ml) were added and the mixture was stirred vigorously for 5 minutes then passed through a PTFE separation frit. The organic layer was collected and evaporated in vacuo to give a white foam. The foam was dissolved in MeOH and loaded on to a SCX cartridge. The cartridge was washed with several column lengths of MeOH followed by 2M ammonia in methanol solution to elute the product. The desired product was obtained as a white foam upon evaporation of the appropriate fractions (46 mg). 1H NMR (500 MHz, CDCl3): δ 8.33 (1H, bs), 7.14 (1H, s), 3.97 (3H, s), 3.59 (2H, d, J 5.1), 2.90-2.84 (3H, m), 2.56 (4H, bs), 2.47 (2H, bs), 2.40 (3H, s), 2.10-2.08 (2H, m), 1.97-1.83 (4H, m), 1.62 (4H, bs), 1.21-1.15 (3H, m), 0.77-0.75 (2H, m), 0.44-0.42 (2H, m). m/z=532 (M+H$^+$).

The following compounds can be prepared by the method of example 38 using the appropriate carbonyl chloride and carboxylic acid:

| Name | MS data |
|---|---|
| 2,4-dichloro-N-(4-cyclopropylmethanesulfonyl-1-morpholin-4-ylmethyl-cyclohexylmethyl)-benzamide | 504 |
| N-(4-cyclopropylmethanesulfonyl-1-morpholin-4-ylmethyl-cyclohexylmethyl)-2-methoxy-4-methyl-6-trifluoromethyl-nicotinamide | 548 |
| N-(4-cyclopropylmethanesulfonyl-1-morpholin-4-ylmethyl-cyclohexylmethyl)-2-methyl-6-trifluoromethyl-nicotinamide | 519 |

EXAMPLE 39

N-[4-cyclopropylmethanesulfonyl-1-(pyrrolidine-1-carbonyl)-cyclohexylmethyl]-2-methoxy-4-methyl-6-trifluoromethyl-nicotinamide (1-aminomethyl-4-cyclopropylmethanesulfonyl-cyclohexyl)-pyrrolidin-1-yl-methanone To 4-cyclopropylmethanesulfonyl-1-(pyrrolidine-1-carbonyl)-cyclohexanecarbonitrile (231 mg; 0.712 mmol) in 2 M ammonia in methanol solution (15 ml) under a nitrogen atmosphere was added Raney Nickel (approx. 1 ml of 50% aqueous slurry). The resulting mixture was agitated under an atmosphere of hydrogen (50 psi) on a Parr apparatus for 18 hours. The mixture was filtered through a catalyst filter and the catalyst washed extensively with MeOH (200 ml, added in portions). The filtrate was evaporated in vacuo to give the product as a pale green oil (241 mg). m/z=329 (M+H$^+$).

N-[4-cyclopropylmethanesulfonyl-1-(pyrrolidine-1-carbonyl)-cyclohexylmethyl]-2-methoxy-4-methyl-6-trifluoromethyl-nicotinamide To a stirred solution of (1-aminomethyl-4-cyclopropylmethanesulfonyl-cyclohexyl)-pyrrolidin-1-yl-methanone (50 mg; 0.152 mmol) in DCM (2 ml) were added WSCDI (68 mg; 0.228 mmol), HOBT (3 mg; 0.0228 mmol) and acid (54 mg; 0.228 mmol). The resulting mixture was stirred at room temperature for 64 hours. Water (5 ml) and DCM (5 ml) were added and the mixture was stirred vigorously for 5 minutes then passed through a PTFE separation frit. The organic layer was collected and evaporated in vacuo. The crude product was purified by prep. TLC eluted with 5% MeOH in DCM to give a foam, which was crystallized from EtOAc/hexane to give the product as a white solid (36 mg). 1H NMR δ (ppm) (CDCl3): 7.12 (1H, s), 6.65 (1H, t, J=6.0 Hz), 3.95 (3H, s), 3.83 (2H, d, J=6.2 Hz), 3.59 (4H, bs), 3.00-2.92 (3H, m), 2.40 (3H, s), 2.20-2.16 (2H, m), 2.11-1.87 (10H, m), 1.23-1.17 (1H, m), 0.78-0.74 (2H, m), 0.45-0.43 (2H, m). m/z=546 (M+H$^+$).

The invention claimed is:
1. A compound of formula I:

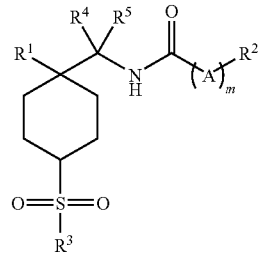

wherein:
R$^1$ is —(CH$_2$)$_n$—R$^{1a}$, wherein n is independently 0-6, and R$^{1a}$ is selected from the group consisting of:
  (1) C$_{1-6}$alkyl, which is unsubstituted or substituted with 1-6 halogen, hydroxy,
  (2) phenyl substituted with R$^{2a}$, R$^{2b}$ and R$^{2c}$,
  (3) heterocycle substituted with R$^{2a}$, R$^{2b}$ and R$^{2c}$,
  (4) C$_{3-6}$cycloalkyl, which is unsubstituted or substituted with C$_{1-6}$alkyl, 1-6 halogen, hydroxy or —NR$^{10}$R$^{11}$,
  (5) —O—C$_{1-6}$alkyl, which is unsubstituted or substituted with 1-6 halogen, hydroxy or —NR$^{10}$R$^{11}$,
  (6) —CO$_2$R$^9$,
    wherein R$^9$ is independently selected from:
    (a) hydrogen,
    (b) —C$_{1-6}$alkyl, which is unsubstituted or substituted with 1-6 fluoro,
    (c) benzyl, and
    (d) phenyl,
  (7) —NR$^{10}$R$^{11}$,
    wherein R$^{10}$ and R$^{11}$ are independently selected from:
    (a) hydrogen,
    (b) —C$_{1-6}$alkyl which is unsubstituted or substituted with hydroxy, 1-6 fluoro or —NR$^{12}$R$^{13}$, where R$^{12}$ and R$^{13}$ are independently selected from hydrogen and —C$_{1-6}$alkyl,
    (c) —C$_{3-6}$cycloalkyl, which is unsubstituted or substituted with hydroxy, 1-6 fluoro or —NR$^{12}$R$^{13}$,
    (d) benzyl,
    (e) phenyl, and
  (8) —CONR$^{10}$R$^{11}$;
R$^2$ is selected from the group consisting of:
  (1) phenyl, which is substituted with R$^{2a}$, R$^{2b}$ and R$^{2c}$,
  (2) heterocycle, which is substituted with R$^{2a}$, R$^{2b}$ and R$^{2c}$,
  (3) C$_{1-8}$alkyl, which is unsubstituted or substituted with 1-6 halogen, hydroxy, —NR$^{10}$R$^{11}$, phenyl or heterocycle, where the phenyl or heterocycle is substituted with R$^{2a}$, R$^{2b}$ and R$^{2c}$,
  (4) C$_{3-6}$cycloalkyl, which is unsubstituted or substituted with 1-6 halogen, hydroxy or —NR$^{10}$R$^{11}$, and
  (5) —C$_{1-6}$alkyl-(C$_{3-6}$cycloalkyl), which is unsubstituted or substituted with 1-6 halogen, hydroxy or —NR$^{10}$R$^{11}$;
R$^{2a}$, R$^{2b}$ and R$^{2c}$ are independently selected from the group consisting of:
  (1) hydrogen,
  (2) halogen,
  (3) —C$_{1-6}$alkyl, which is unsubstituted or substituted with:
    (a) 1-6 halogen,
    (b) phenyl,
    (c) C$_{3-6}$cycloalkyl, or
    (d) —NR$^{10}$R$^{11}$, (4) —O—$C_{1-6}$alkyl, which is unsubstituted or substituted with 1-6 halogen,
(5) hydroxy,
(6) —$SCF_3$,
(7) —$SCHF_2$,
(8) —$SCH_3$,
(9) —$CO_2R^9$,
(10) —CN,
(11) —$SO_2R^9$,
(12) —$SO_2$—$NR^{10}R^{11}$,
(13) —$NR^{10}R^{11}$,
(14) —$CONR^{10}R^{11}$, and
(15) —$NO_2$,
or two of $R^{2a}$, $R^{2b}$ and $R^{2c}$ are linked to form a

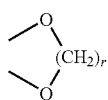

group wherein r is 1 to 3;
$R^3$ is selected from the group consisting of:
(1) $C_{1-6}$alkyl, which is substituted with heterocycle, which is substituted with $R^{2a}$, $R^{2b}$ and $R^{2c}$, and
(2) heterocycle, which is substituted with $R^{2a}$, $R^{2b}$ and $R^{2c}$;
$R^4$ and $R^5$ are independently selected from the group consisting of:
(1) hydrogen, and
(2) $C_{1-6}$alkyl, which is unsubstituted or substituted with halogen or hydroxyl, or $R^4$ and $R^5$ taken together form a $C_{3-6}$cycloalkyl ring;
A is selected from the group consisting of:
(1) —O—, and
(2) —$NR^{10}$—;
m is zero or one, whereby when m is zero $R^2$ is attached directly to the carbonyl;
and pharmaceutically acceptable salts thereof and individual enantiomers and diastereomers thereof.

2. A compound according to claim 1 of formula Id:

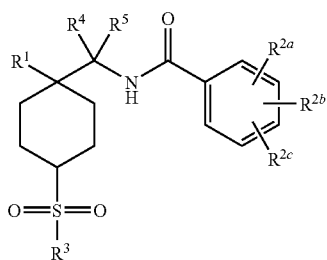

wherein $R^1$, $R^3$, $R^4$ are as defined in claim 1 and $R^{2a}$, $R^{2b}$ and $R^{2c}$ are selected from hydrogen, fluoro, chloro, bromo, $OCH_3$ $CF_3$, $OCF_3$ and $NH_2$.

3. A compound according to claim 1 of formula Ie:

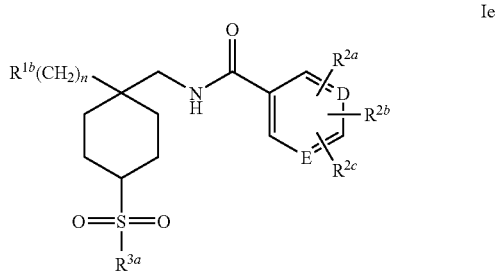

wherein n, $R^{2a}$, $R^{2b}$ and $R^{2c}$ are as defined in claim 1;
$R^{1b}$ is a $C_{3-6}$cycloalkyl, which is unsubstituted or substituted with $C_{1-6}$alkyl, 1-6 halogen, hydroxy or —$NR^{10}R^{11}$;
D and E are each independently CH or N, and
$R^{3a}$ is an unsaturated heterocycle optionally substituted by a halogen or a $C_{1-6}$alkyl or $C_{1-6}$haloalkyl group.

4. A compound according to claim 1 wherein $R^1$ is $C_{3-6}$cycloalkyl.

5. A compound according to claim 1 wherein $R^2$ is phenyl substituted by $R^{2a}$, $R^{2b}$ and $R^{2c}$ which are independently selected from hydrogen, fluoro, chloro, bromo, $OCH_3$, $CF_3$, $OCF_3$ and $NH_2$.

6. A compound according to claim 1 wherein $R^4$ and $R^5$ are hydrogen.

7. A compound according to claim 1 wherein n is zero or one.

8. A compound according to claim 1 which is:
2,4-dichloro-N-({1-cyclopropylmethyl-4-[(1-methyl-1H-1,2,3-triazol-4-yl)sulfonyl]cyclohexyl}methyl)benzamide;
2-chloro-N-({1-(cyclopropylmethyl)-4-[(1-methyl-1H-pyrazol-4-yl)sulfonyl]cyclohexyl}methyl)-4-(trifluoromethyl)benzamide;
2,4-dichloro-N-({1-(1-hydroxy-1-methylethyl)-4-[(1-methyl-1H-1,2,3-triazol-4-yl)sulfonyl] cyclohexyl}methyl)benzamide;
2,4-dichloro-N-({1-(cyclopropylmethyl)-4-[(5-methyl-1,3,4-thiadiazol-2-yl)sulfonyl]cyclohexyl}methyl)benzamide;
or a pharmaceutically acceptable salt thereof, or an enantiomer or disasteromer thereof.

9. A pharmaceutical composition comprising a therapeutically effective amount of a compound of claim 1, or a pharmaceutically acceptable salt thereof, or an enantiomer or diastereomer thereof, and a pharmaceutically acceptable carrier.

* * * * *